United States Patent [19]

Haviv et al.

[11] Patent Number: 5,140,009

[45] Date of Patent: Aug. 18, 1992

[54] OCTAPEPTIDE LHRH ANTAGONISTS

[75] Inventors: Fortuna Haviv, Deerfield; Jonathan Greer, Chicago, both of Ill.; Christopher A. Palabrica, River Hills, Wis.; Timothy D. Fitzpatrick, Libertyville, Ill.

[73] Assignee: Tap Pharmaceuticals, Inc., Deerfield, Ill.

[21] Appl. No.: 548,511

[22] Filed: Jul. 10, 1990

Related U.S. Application Data

[63] Continuation-in-part of Ser. No. 390,269, Aug. 7, 1989, abandoned, which is a continuation-in-part of PCT/US89/00531, Feb. 9, 1989, which is a continuation-in-part of Ser. No. 154,682, Feb. 10, 1988, abandoned.

[51] Int. Cl.$^5$ .......................... C07K 7/06; C07K 7/20; A61K 37/38
[52] U.S. Cl. .......................... 514/16; 514/15; 530/313; 530/328; 530/329
[58] Field of Search .......................... 530/313, 329, 328; 514/17, 16, 15

[56] References Cited

U.S. PATENT DOCUMENTS

| | | |
|---|---|---|
| 4,493,934 | 1/1985 | Verber et al. |
| 4,690,916 | 9/1987 | Nestor et al. |
| 4,760,053 | 7/1988 | Labrie .......................... 514/15 |

OTHER PUBLICATIONS

Stewart, et al., *Solid Phase Peptide Synthesis*, Pierce Chem. Co., 1984.
Koch, et al., *Chem. Abs.*, 107:33505z, p. 109, 1987.
Shidgel, R., et al., Proc. Natl. Acad. Sci., 82:1025–1029, 1985.
Wojciechowski, et al., *Drug. Intell. and Clinical Pharmacy*, 20:746–751, 1986.
Furr, et al., *J. Endocrinol. Invest.*, 11:535–557, 1988.
Burov, et al., Chem. Abstracts 108:16411 (1988).
Sandow, et al., J. Endocrinol. 81 175 (1979).
Cyril Y. Bowers, "LH and FSH Release," in Biol. Act. Princ. Nat. Prod. Wolfgang Voelker, Daves, Doyle & G. Thieme, Stuttgart, Germany, 1984, pp. 126–137.

*Primary Examiner*—Merrell C. Cashion, Jr.
*Assistant Examiner*—Susan M. Perkins
*Attorney, Agent, or Firm*—Jerry F. Janssen; Steven R. Crowley

[57] ABSTRACT

The present invention relates to novel LHRH analogs. The LHRH analogs include "pseudo" hexapeptide, heptapeptide, octapeptide and nonapeptide analogs of LHRH, wherein all or some of the amino acids, 1, 2 and 3 have been eliminated and the remaining (2-9), (2-10), (3-9), (3-10), (4-9) or (4-10) peptide is linked to various carboxylic acids which take the place of amino acids 1, 2 or 3 in LHRH.

8 Claims, 2 Drawing Sheets

OCTAPEPTIDE LHRH ANTAGONISTS

CROSS-REFERENCE TO RELATED APPLICATIONS

This application is a continuation-in-part of copending application Ser. No. 390,269 filed Aug. 7, 1989, now abandoned, which is a continuation-in-part of application PCT/US89/00531, which in turn is a continuation-in-part of application Ser. No. 154,682 filed Feb. 10, 1988, now abandoned.

TECHNICAL FIELD

The present invention relates to novel LHRH analogs. The LHRH analogs include "pseudo" hexapeptide, heptapeptide, octapeptide and nonapeptide analogs of LHRH, wherein all or some of the amino acids 1, 2 and 3 have been eliminated and the remaining (2-9), (2-10), (3-9), (3-10), (4-9) or (4-10) peptide is linked to various carboxylic acids which mimic amino acids 1, 2 or 3 in LHRH. The invention also relates to processes for preparing such compounds, to pharmaceutical compositions containing such compounds and to the use of such compounds for modulating levels of sex hormones in male or female mammals.

BACKGROUND ART

Luteinizing hormone releasing hormone, known as LHRH or GnRH, is a decapeptide with the following formula:

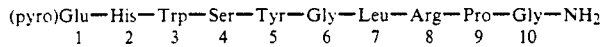

(pyro)Glu—His—Trp—Ser—Tyr—Gly—Leu—Arg—Pro—Gly—NH$_2$
   1     2    3    4    5    6    7    8    9   10

LHRH is released from the hypothalamus and binds to a receptor on the pituitary gland, causing the release of LH (Luteinizing Hormone) and FSH (Follicle - Stimulating Hormone). Subsequently, LH and FSH act on the gonads to stimulate the synthesis of steroid sex hormones. The pulsatile release of LHRH, and thereby the release of LH and FSH, controls the reproductive cycle in domestic animals and humans. Acute doses of LHRH agonists increase the levels of LH and steroid sex hormones in both animals and humans. Paradoxically, chronic doses of these agonists suppress the levels of LH and steroid hormones. Consequently, the effect of multiple doses of LHRH agonists is to suppress estrogen in the female and testosterone in the male. The same effect is observed in both animals and humans after administration of acute or chronic doses of LHRH antagonists. LHRH agonists are currently used or under clinical investigation for the treatment of several hormone dependent diseases such as prostate cancer, benign prostatic hypertrophy, endometriosis, uterine fibroids, precocious puberty and breast cancer. They have also been used as contraceptives. For a review of LHRH analogs see J. Sandow, et al. in "Hypothalamic Hormones. Chemistry, Physiology, and Clinical Applications", edited by D. Gupta and W. Voeters, p. 307 (1978).

Biologically active LHRH analogs have been studied in animals and humans. LHRH analogs have been found to be effective by either intravenous, subcutaneous, or depot administration. Intranasal and intravaginal administrations are effective only at very high doses. All of the reported LHRH analogs show 0.1% to 1% potency following oral administration when compared to intraveneous doses. Two major reasons for the low bioavailability are: 1) these peptides are degraded in the stomach by various proteolytic enzymes before reaching the blood system; and 2) peptides containing more than three or four amino acids are not absorbed well. It would be desirable to prepare analogs of LHRH that are stable against proteolytic enzymes, are smaller in size, and are active after oral administration in animals and humans.

SUMMARY OF THE INVENTION

The present invention relates to novel LHRH analogs. These LHRH analogs include "pseudo" hexapeptide, heptapeptide, octapeptide and nonapeptide analogs of LHRH, wherein all or some of the amino acids 1, 2 and 3 have been eliminated and the remaining (2-9), (2-10), (3-9), (3-10), (4-9) or (4-10) peptide is linked to various carboxylic acids which mimic amino acids 1, 2 or 3 in LHRH.

DISCLOSURE OF THE INVENTION

Figure 1:
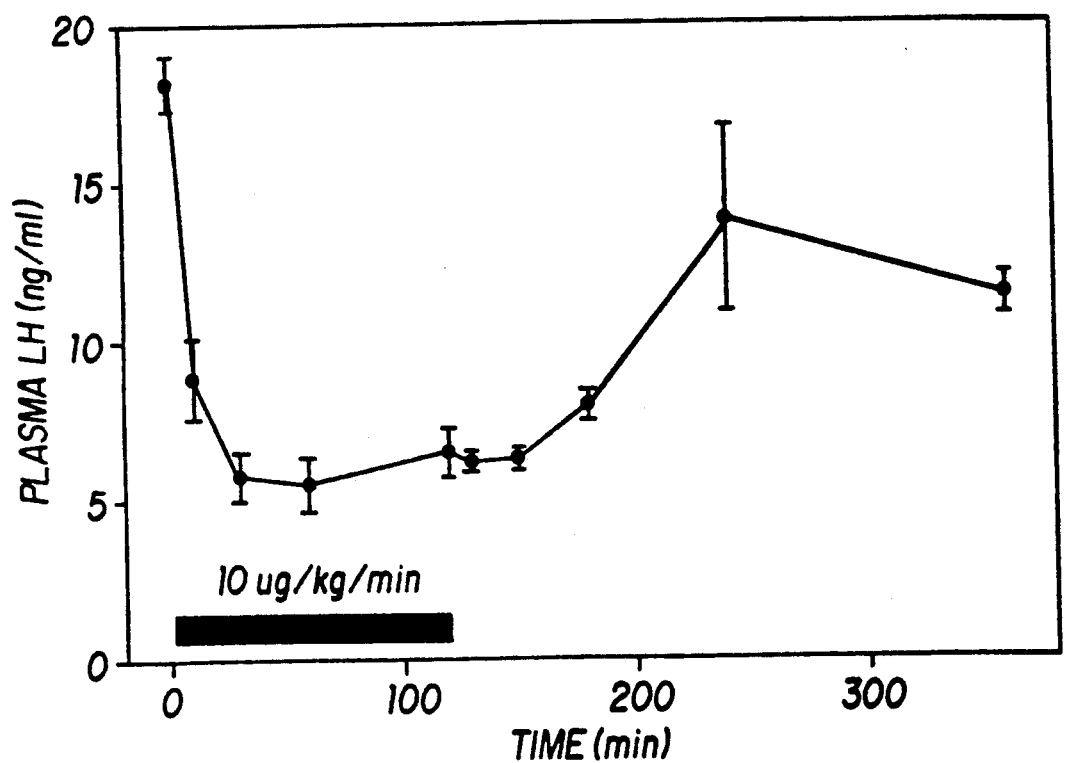
FIG. 1 is a plot of the level of LH in mature castrate male rats during and after i.v. infusion (beginning at time 0) of 10 ug/kg/min of LHRH antagonist compound 20. The infusion lasted 120 minutes.

The compounds of the present invention are of the formula:

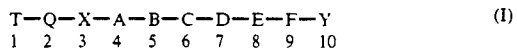

T—Q—X—A—B—C—D—E—F—Y     (I)
1  2  3  4  5  6  7  8  9  10 or a pharmaceutically acceptable salt thereof; wherein
T is absent or T is D- or L-N-delta Et-glutamyl or T is an acyl residue of the formula:

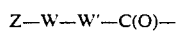

Z—W—W'—C(O)— wherein Z is hydrogen, loweralkyl, cycloalkyl, 1-adamantyl, naphthyl, 5,6-dihydro-5,5-dimethyl-2-oxo-3-phenyl-1-(2H)-pyrazinyl, phenyl, substituted phenyl or heterocyclic; W is absent or W is an alkylene or alkenylene group; and W' is absent, O, S or NH;

Q is absent or Q is a D or L-amino acyl residue which is substituted on the alpha-amino nitrogen atom with hydrogen or $C_1$ to $C_3$ alkyl and which is selected from phenylalanyl, homophenylalanyl, histidyl, 3-(1-naphthyl)-alanyl, 3-(2-naphthyl)-alanyl, 3-pyridylalanyl, 3-quinolylalanyl, 3-(2-naphthyl)-alanyl, O-methyl-tyrosyl, tryptyl, tryptyl(N-indole-formyl), 3-(5-thiazolyl)alanyl, 3-(2-thienyl)alanyl, 3-(3-benzthienyl)alanyl, 3-(3-pyrazolyl)-alanyl or (substituted-phenyl)alanyl;

or Q is an alpha-aza amino acid residue which is substituted on the alpha-amino nitrogen atom with hydrogen or $C_1$ to $C_3$ alkyl and which is selected from alpha-aza-phenylalanyl, alpha-aza-(4-chlorophenyl)alanyl, alpha-aza-(2-naphthyl)alanyl, alpha-aza-(4-fluorophenyl)alanyl, alpha-aza-histidyl, alpha-aza-tryptyl and alpha-aza-3-(3-benzthienyl)alanyl;

or, when T is absent, Q is an acyl residue of the formula:

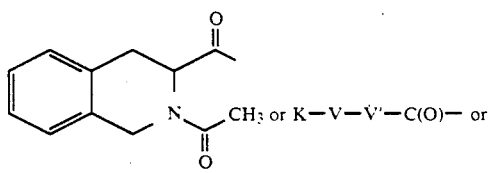

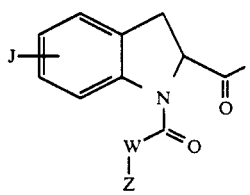

wherein K is hydrogen, loweralkyl, cycloalkyl, 1-adamantyl, naphthyl, 1,2,3,4-tetrahydronaphthyl, phenyl or substituted phenyl, or K is 5,6-dihydro-5,5-dimethyl-2-oxo-3-phenyl-1-(2H)-pyrazinyl or heterocyclic; V is absent or V is an alkylene or alkenylene group; V' is absent, O, S or NH; and J is hydrogen, halogen, methoxy or trifluoromethyl and W and Z are independently defined as above;

or Q is

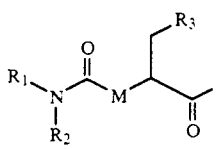

wherein M is NH or $CH_2$: $R_1$ is loweralkyl, cycloalkyl or $R_{16}(CH_2)_q$— wherein q is 1-5 and $R_{16}$ is naphthyl, 1,2,3,4-tetrahydronaphthyl, indolyl, substituted indolyl wherein the indole is substituted with loweralkyl, halogen, trifluoromethyl or methoxy, phenyl or substituted phenyl; $R_2$ is hydrogen, loweralkyl, cycloalkyl or $R_{17}(CH_2)_s$— wherein s is 1-5 and $R_{17}$ is naphthyl, 1,2,3,4-tetrahydronaphthyl, phenyl or substituted phenyl; or $R_1$ and $R_2$ taken together form a heterocyclic ring selected from morpholine, piperidine, pyrrolidine thiomorpholine, N-acetylpiperazine and N-($C_1$-$C_3$alkyl)piperazine; and $R_3$ is 1-naphthyl, 2-naphthyl, 1-adamantyl, heterocyclic, phenyl or substituted phenyl;

X is absent or X is a D- or L-amino acyl residue which is substituted on the alpha-amino nitrogen atome with hydrogen or $C_1$-$C_3$ alkyl and which is selected from tryptyl, tryptyl substituted with halogen, methoxy or loweralkyl, tryptyl(N-indole-formyl), 3-(1-naphthyl)alanyl, 3-(2-naphthyl)alanyl, 3-quinolylalanyl, 3-(3-benzthienyl)alanyl, 3-(3-benzoxazolyl)alanyl, 3-(3-pyridyl)alanyl, 3-(3-pyridyl-N'-oxide)alanyl, tryptyl(N-indole-methyl), prolyl, substituted prolyl wherein the proline is substituted in the 3 position with loweralkyl or phenyl, 3-(5-thiazolyl)alanyl, 3-(2-thienyl)alanyl, cyclohexylalanyl, 3-(3-pyrazolyl)alanyl, 3-(3-indazolyl)alanyl, 3-(pentamethylphenyl)alanyl, 3-(3,4,5-trimethylphenyl)alanyl, homophenylalanyl, phenylalanyl, (substituted phenyl)alanyl, tyrosyl, tyrosyl(O-methyl), 1,2-dihydro-3-carbonyl-indolyl and 1,2,3,4-tetrahydro-3-carbonyl isoquinolyl;

or X is an alpha aza amino acid residue which is substituted on the alpha-amino nitrogen atom with hydrogen or $C_1$-$C_3$ alkyl and which is selected from alpha-aza-3-(1-naphthyl)alanyl, alpha-aza-tryptyl, alpha-aza-phenylalanyl, alpha-aza-(substituted-phenyl)alanyl, alpha-aza-3-(3-benzthienyl)alanyl, alpha-aza-3-(2-thienyl)alanyl, alpha-aza-3-(4-methylphenyl)alanyl, alpha-aza-3-(pentamethylphenyl)alanyl, alpha-aza-3-(3-pyridyl)alanyl, alpha-aza-3-(3-quinolyl)alanyl, alpha-aza-tryptyl(N-indole-methyl) and alpha-aza-3-(5-thiazolyl)alanyl;

or, when T and Q are absent, X is an acyl residue of the formula:

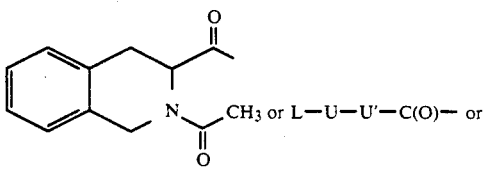

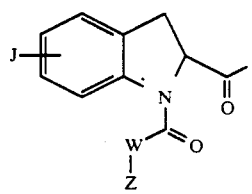

wherein W, Z and J are independently defined as above; L is hydrogen, loweralkyl, cycloalkyl, 1-adamantyl, naphthyl, 1,2,3,4-tetrahydronaphthyl, 1-naphthyloxy, phenoxy, phenyl, substituted phenyl or heterocyclic; U is absent or U is an alkylene or alkenylene group; and U' is absent, O, S or NH;

or X is

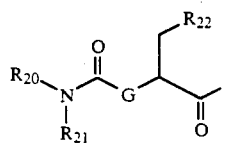

wherein G is NH or $CH_2$; $R_{20}$ is loweralkyl, cycloalkyl or $R_{18}(CH_2)_t$— wherein t is 1-5 and $R_{18}$ is naphthyl, 1,2,3,4-tetrahydronaphthyl, heterocyclic, phenyl or substituted phenyl; $R_{21}$ is hydrogen, loweralkyl, cycloalkyl or $R_{19}(CH_2)_v$— wherein v is 1-5 and $R_{19}$ is naphthyl, 1,2,3,4-tetrahydronaphthyl, phenyl or substituted phenyl; or $R_{20}$ and $R_{21}$ taken together form a heterocyclic ring selected from morpholine, piperidine, pyrrolidine, thiomorpholine, N-acetylpiperazine and N-($C_1$-$C_3$alkyl)piperazine; and $R_{22}$ is loweralkyl or —$(CH_2)_yR_{30}$ wherein y is 0 to 5 and $R_{30}$ is amino, alkylamino, guanidino, hydroxy, alkoxy or thioalkoxy, or $R_{22}$ is 1-naphthyl, 2-naphthyl, 1-adamantyl, heterocyclic, phenyl or substituted phenyl;

A is an amino acyl residue which is substituted on the alpha-amino nitrogen atom with hydrogen or $C_1$ to $C_3$ alkyl and which is selected from L-seryl, L-seryl(O-benzyl), alanyl, glutaminlyl, prolyl, 3-hydroxyprolyl, prolyl substituted at the 3 position with loweralkyl or phenyl, threonyl, seryl, seryl(O—$PO_3H_2$), seryl-(O—$PO_3Me_2$), threonyl(O—$PO_3H_2$), threonyl-(O—$PO_3Me_2$), 2-amino-3-guanidino propionyl, 2,3-diaminopropionyl and substituted derivatives thereof wherein the 3-amino group is substituted with loweralkyl or —C(O)-heterocyclic;

or A is an apha-aza amino acid residue which is substituted on the alpha-amino nitrogen atom with hydrogen or $C_1$-$C_3$ alkyl and which is selected from alpha-aza-glycyl, alpha-aza-seryl, alpha-aza-alanyl and alpha-aza-threonyl;

or A is a glycosyl derivative or serine or threonine;

B is an amino acyl residue which is substituted at the alpha-amino nitrogen with hydrogen or $C_1$ to $C_3$ alkyl and which is selected from L-tyrosyl, L-tyrosyl-(O—$PO_3H_2$), L-tyrosyl(O—$PO_3Me_2$), L-tryptyl, L-3-(1-naphthyl)alanyl, L-3-(2-thienyl)alanyl, L-histidyl, L-3-(3-benzthienyl)alanyl, L-tryptyl(N-indole-methyl), L-3-(4-chlorophenyl)alanyl, L-3-(4-fluorophenyl)alanyl, L-3-(4-acetylaminophenyl)alanyl, L-3-(1-naphthyl)alanyl, L-3-(4-aminophenyl)alanyl, L-3-(cyclohexyl)alanyl, L-homophenylalanyl, L-phenylalanyl, L-tyrosyl(O-methyl), seryl, threonyl, L-tyrosyl(O-ethyl), and

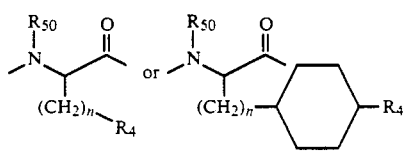

wherein n is 1 to 4; $R_{50}$ is hydrogen, methyl, ethyl, propyl or isopropyl; and $R_4$ is amino, alkylamino, cycloalkylamino or alkanoylamino; or $R_4$ is —N($R_6$)-C(O)($CH_2$)$_{aa}R_{100}$ or —NHC(NH($R_6$))=$NR_7$ wherein $R_6$ is hydrogen, loweralkyl or cycloalkyl; $R_7$ is hydrogen, loweralkyl, cycloalkyl, amino or cyano; aa is 0 to 6; and $R_{100}$ is loweralkyl, dialkylamino, heterocyclic, phenyl, substituted phenyl, cycloalkyl or —$NHR_{101}$ wherein $R_{101}$ is hydrogen, loweralkyl, cycloalkyl, amino, alkanoylamino, heterocyclic, phenyl or substituted phenyl;

C is a D-amino acyl residue which is substituted at the alpha-amino nitrogen with hydrogen or $C_1$ to $C_3$ alkyl and which is derived from any of the naturally occuring alpha-amino acids or from synthetic, non-natural alpha amino acids, including, but not limited to a D-amino acyl residue of the formula:

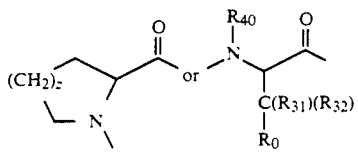

or protected derivatives thereof, including D-tryptyl(N-indole-formyl) wherein z is 1 or 2; $R_{31}$ and $R_{32}$ are independently selected from hydrogen and loweralkyl; $R_{40}$ is hydrogen, methyl, ethyl, propyl or isopropyl; $R_0$ is $C_1$ to $C_6$ straight or branched chain alkyl, $C_3$ to $C_6$ cycloalkyl, hydroxy, alkoxy, thioalkoxy, phenyl, substituted phenyl, benzyl, substituted benzyl or heterocyclic; or $R_0$ is —$(CH_2)_mR_8$ or

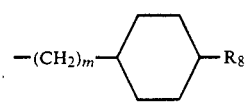

wherein m is 0 to 4 and $R_8$ is amino, alkylamino, cycloalkylamino, alkanoylamino, benzoyl or benzoyl substituted with halo, alkoxy, loweralkyl, cyano or nitro;

or $R_8$ is —N(R')C(O)$(CH_2)_{hh}R_{116}$ or —NHC(NH(R'))=NR" wherein R' is hydrogen, loweralkyl or cycloalkyl; R" is hydrogen, loweralkyl, cycloalkyl, amino or cyano; hh is 0 to 6; and $R_{116}$ is loweralkyl, dialkylamino, heterocyclic, phenyl, substituted phenyl, cycloalkyl or —$NHR_{117}$ wherein $R_{117}$ is hydrogen, loweralkyl, cycloalkyl, heterocyclic, phenyl, substituted phenyl, amino or alkanoylamino;

or C is seryl(O—$PO_3H_2$), seryl(O—$PO_3Me_2$), threonyl(O—$PO_3H_2$) or threonyl (O—$PO_3Me_2$);

or C is a glycosyl derivative of serine or threonine;

D is an amino acyl residue which is substituted on the alpha-amino nitrogen with hydrogen or $C_1$ to $C_3$ alkyl and which is selected from L-leucyl, L-isoleucyl, L-norleucyl, L-valyl, phenylalanyl, seryl, threonyl, threonyl-(O—$PO_3H_2$), threonyl(O—$PO_3Me_2$), seryl-(O—$PO_3H_2$), seryl (O—$PO_3Me_2$), tryptyl, tyrosyl, tyrosyl(OMe), prolyl, pipecolyl, norvalyl, 2-aminobutyryl, alloisoleucyl and 3-(cyclohexyl)-alanyl;

or D is a glycosyl derivative of serine or threonine;

or C and D taken together are a residue of the formula:

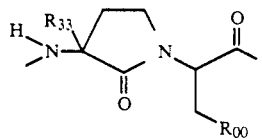

wherein $R_{00}$ is loweralkyl, phenyl or indolyl and $R_{33}$ is hydrogen, loweralkyl, 3-indolylmethyl, 2-naphthylmethyl, 2-benzimidazolyl, 2-thienyl, 3-benzthienyl or substituted benzyl;

E is an L-amino acyl residue of the formula:

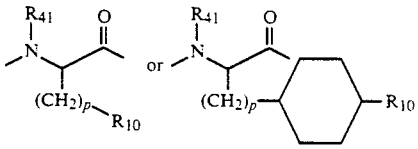

wherein p is 1 to 4; $R_{41}$ is hydrogen, methyl, ethyl, propyl or isopropyl; and $R_{10}$ is amino, alkylamino, cycloalkylamino or alkanoylamino; or $R_{10}$ is —N($R_{12}$)-C(O)$(CH_2)_{ii}R_{102}$ or —NHC(NH($R_{12}$))=$NR_{13}$ wherein $R_{12}$ is hydrogen, loweralkyl or cycloalkyl, $R_{13}$ is hydrogen, loweralkyl, cycloalkyl, amino or cyano; ii is 0 to 6; and $R_{102}$ is loweralkyl, dialkylamino, heterocyclic, phenyl, substituted phenyl, cycloalkyl or —$NHR_{103}$ wherein $R_{103}$ is hydrogen, loweralkyl, cycloalkyl, phenyl, substituted phenyl, heterocyclic, amino or alkanoylamino;

F is an imino acyl or aliphatic amino acyl residue selected from L-prolyl, L-pipecolyl, trans-beta-aminocyclopentanecarbonyl, cis-beta-aminocyclopentanecarbonyl, N-($C_1$-$C_3$alkyl)-L-alanyl, 3-(loweralkyl)-prolyl, 3-phenylprolyl, N-($C_1$-$C_3$alkyl)-L-norvalyl, alpha-aza-prolyl, 1-dihydroisoindole-2-L-carbonyl and thiazolidine-5-L-carbonyl; and Y is L-alanylamide, D-alanylamide, sarcosylamide, glycylamide, N-($C_1$-$C_3$alkyl)-L-alanylamide, N-($C_1$-$C_3$alkyl)-D-alanylamide, L-2-aminobutyrylamide, D-2-aminobutyrylamide, alpha-aza-alanylamide, L-norvalinylamide, D-norvalinylamide, L-serylamide, D-serylamide, 1-pyrrolidinyl, 1-piperidinyl, 4-morpholinyl, —NHR$_{14}$ or —NHCH$_2$C(O)NHR$_{14}$, wherein R$_{14}$ is hydrogen, loweralkyl, cycloalkyl, hydroxy substituted loweralkyl or fluoro substituted loweralkyl; or Y is —N(R$_{150}$)N(R$_{151}$)C(O)NHR$_{15}$ wherein R$_{15}$ is hydrogen, loweralkyl, cycloalkyl, hydroxy substituted loweralkyl or fluoro substituted loweralkyl and R$_{150}$ and R$_{151}$ are independently selected from hydrogen and loweralkyl.

These compounds exhibit LHRH agonist or antagonist properties.

As set forth above, and for convenience in describing this invention, the conventional abbreviations for the various common amino acids are used as generally accepted in the peptide art as recommended by the IUPAC-IUB Commission on biochemical Nomenclature, *Biochemistry II*, 1726 (1972). These represent L-amino acids, with the exception of the achiral amino acid glycine, and with the further exception of any unnatural or natural amino acids which are achiral, or are otherwise designated as D-. All peptide sequences mentioned herein are written according to the generally accepted convention whereby the N-terminal amino acid is on the left and the C-terminal amino acid is on the right.

Other abbreviations which are useful in describing the invention are the following:

| Amino acids, protecting groups, reagents | Abbreviation |
|---|---|
| L-N-(epsilon)-isopropyllysyl | Lys (isp) |
| Arginine | Arg |
| t-Butoxycarbonyl | Boc |
| Benzyl | Bzl |
| Benzyloxycarbonyl | Cbz |
| N,N'-Dicyclohexylcarbodiimide | DCC |
| N,N'-di-isopropylcarbodiimide | DIC |
| Glycine | Gly |
| Histidine | His |
| 1-Hydroxybenzotriazole | HOBt |
| Isoleucine | Ileu |
| Leucine | Leu |
| N-epsilon-nicotinyllysyl | Lys(Nic) |
| Norleucine | Nleu |
| Norvaline | Nval |
| Methionine | Met |
| Methyl ester | OMe |
| Benzyl ester | OBzl |
| Phenylalanine | Phe |
| Proline | Pro |
| Pyroglutamic acid | (pyro)Glu |
| Serine | Ser |
| Tosyl | Tos |
| Tryptophan | Trp |
| Tyrosine | Tyr |
| 3-(pyridyl)-L-alanyl | 3-Pal |
| (3R) or (3S)-1, 2, 3, 4-tetrahydro-isoquinoline-3-carbonyl | 3-Tic |
| L-O-methyltyrosyl | O-Me-Tyr |
| L-cyclohexylalanyl | Cha |
| 3-(2-naphthyl)-D-alanyl | D-2-Nal |
| 3-(1-naphthyl)-L-alanyl | 1-NaL |
| 3-(2-thienyl)-D-alanyl | D-Thia |
| 3-(pyrazolyl)-L-alanyl | 3-Pyral |
| D-3-(3-benzthienyl)alanyl | D-Bal |
| 4-dimethylaminopyridine | DMAP |
| 3-(3, 4, 5-trimethylphenyl)alanyl | Tmp |
| D-3-(5-thiazolyl)alanyl | D-Thiaz |
| homo-citrulline | Hcit |
| D-Ser-(O-alpha-L-Rhamnosyl) | D-Ser(O-alpha L-Rha) |
| D-Lys(N-epsilon-4-methoxybenzoyl) | D-Lys(Anis) |
| Lys(N-epsilon-carbonyl-N'-hydrazine) | Lys(CO-Hyr) |
| D-Lys(N-epsilon-2-pyrazinecarbonyl) | D-Lys(Pyrz) |
| Lys(N-epsilon-carbonyl-N'-hydrazine-N-acetyl) | Lys(CO-Hyr-Ac) |
| D-Lys(N-epsilon-carbonyl-N'-morpholine) | D-Lys(CO-Morph) |
| D-Lys(N-epsilon-carbonyl-N'-piperazinyl-N'-methyl) | D-Lys(CO-NMePip)Hom |
| (3-(2-phenethyl)alanine) | hhPhe |
| Arg(N,N'-guanidino-diethyl) | Arg(N$^G$-diethyl) |
| Arg(N-guanidino-amino) | Arg(N$^G$-amino) |
| Homocitrulline(N-ureido-amine) | Hcit(N$^u$-amino) |
| Arg(N-quanidino-methyl-N'-guanidino-cyano) | Arg(N$^G$-methyl-N'$^G$-cyano) |

The sequence of LHRH has been shown to be

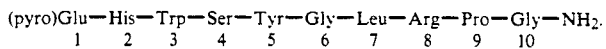

(pyro)Glu—His—Trp—Ser—Tyr—Gly—Leu—Arg—Pro—Gly—NH$_2$.
   1    2   3   4   5   6   7   8   9  10

Nona- and decapeptides in which the amino acid residues at particular places in the sequence have been replaced by other amino acid residues or other moieties are abbreviated by showing the nature of the substitution, superscribed by the location, followed by LHRH as the parent. For example, the sequence

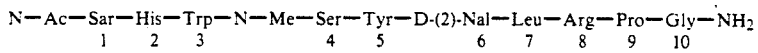

N—Ac—Sar—His—Trp—N—Me—Ser—Tyr—D-(2)-Nal—Leu—Arg—Pro—Gly—NH$_2$
       1    2   3         4     5       6    7   8   9  10 is represented [N-Ac-Sar$^1$, N-Me-Ser$^4$, D-(2)-Nal$^6$]LHRH; the sequence (pyro)Glu-His-Trp-N-Me-Ser-Try-D-Trp$^6$-Leu-Arg-Pro-NHEt is represented [N-Me-Ser$^4$-D-Trp$^6$-Pro$^9$-NHEt]LHRH; and the sequence N-(3-(3-indole)propionyl)-Ser-Tyr-D-Trp-Leu-Arg-Pro-NHEt is represented (4-9)[N-(3-(3-Indole)propionyl)-Ser$^4$-D-Trp$^6$-Pro$^9$-NHEt]LHRH.

As used herein, the term "pharmaceutically acceptable salts" refers to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, methanesulfonic acid, p-toluenesulfonic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or with an organic cation formed from N,N'-dibenzylethylene diamine or ethylenediamine; or (c) combinations, of (a) and (b), e.g., a zinc tannate salt and the like.

The term "loweralkyl" refers to a straight or branched chain saturated hydrocarbon group having from 1 to 6 carbon atoms such as, for example, methyl, ethyl, n-propyl, isopropyl, n-butyl, isobutyl, sec-butyl, tert-butyl, n-pentyl and n-hexyl.

The term "alkyl of 1 to 12 carbon atoms" refers to a straight or branched chain radical of 1 to 12 carbon atoms.

The term "cycloalkyl" refers to a cyclic saturated hydrocarbon group having from 3 to 7 carbon atoms, for example, cyclopropyl, cyclobutyl, cyclopentyl, cyclohexyl and cycloheptyl.

The term "alkylene" refers to $C_1$ to $C_5$ straight or branched chain radicals including, but not limited to, $-CH_2-$, $-CH(CH_3)-$, $-C(CH_3)_2-$, $-CH(C_2H_5)-$, $-CH_2CH_2-$, $-CH_2CH(CH_3)-$, $-C(CH_3)_2CH(CH_3)-$, $-CH_2CH_2CH_2-$, $-CH_2(CH_2)_2CH_2-$, $-CH_2(CH_2)_3CH_2-$ and the like.

The term "alkenylene" refers to $C_2$ to $C_5$ straight or branched chain radicals wherein the unsaturation comprises a carbon-carbon double bond including, but not limited to, $-CH=CH-$, $-CH=CHCH_2-$, $-CH=CHCH(CH_3)-$, $-C(CH_3)=CHCH_2-$, $-CH_2CH=CHCH_2-$, $-CH_2CH=CHCH_2CH_2-$ and the like.

The term "halogen" refers to a F, Cl, Br or I radical.

The term "dialkylamino" refers to $-NR_{25}R_{26}$ wherein $R_{25}$ and $R_{26}$ are independently selected from loweralkyl.

The term "alkylamino" refers to $-NHR_{35}$ wherein $R_{35}$ is loweralkyl.

The term "cycloalkylamino" as used herein refers to $-NHR_{121}$ wherein $R_{121}$ is a cycloalkyl group.

The term "alkoxy" refers to $-OR_{36}$ wherein $R_{36}$ is loweralkyl including, but not limited to, methoxy, ethoxy, t-butyloxy and the like.

The term "thioalkoxy" refers to $-SR_{37}$ wherein $R_{37}$ is loweralkyl including, but not limited to, $-SCH_3$, $-SCH_2CH_3$ and the like.

The term "halogen" or "halo" as used herein refers to I, Br, Cl or F.

The term "alkanoylamino" as used herein refers to $R_{104}C(O)NH-$ wherein $R_{104}$ is loweralkyl.

The term "alkoxycarbonyl" as used herein refers to $R_{105}OC(O)-$ wherein $R_{105}$ is loweralkyl.

The term "alkanoyl" as used herein refers to $-C(O)R_{120}$ wherein $R_{120}$ is loweralkyl.

The term "substituted phenyl" as used herein refers to a phenyl group substituted with one, two or three substituents independently selected from halogen, loweralkyl, hydroxy, alkoxy, thioalkoxy, nitro, amino, alkylamino, dialkylamino, alkanoylamino, trihalomethyl and alkoxycarbonyl. Substituted phenyl groups include pentafluorophenyl and pentamethylphenyl.

The term "substituted benzyl" as used herein refers to a benzyl group in which the phenyl ring is substituted with one, two or three substituents independently selected from halogen, loweralkyl, hydroxy, alkoxy, thioalkoxy, nitro, amino, alkylamino, dialkylamino, alkanoylamino, trihalomethyl and alkoxycarbonyl.

The term "aryl" as used herein refers to a monocyclic or bicyclic carbocyclic ring system comprising an aromatic carbocyclic ring. Aryl groups include, but are not limited to, phenyl, naphthyl, indanyl, indenyl, tetrahydronaphthyl and the like. Aryl groups can be unsubstituted or substituted with one, two or three substituents independently selected from halogen, loweralkyl, hydroxy, alkoxy, thioalkoxy, nitro, amino, alkylamino, dialkylamino, alkanoylamino, trihalomethyl and alkoxycarbonyl. Substituted aryl groups include pentafluorophenyl and pentamethylphenyl. Where a specific aryl group is mentioned as a substituent in a compound of this invention, it is to be understood that this invention is intended to encompass compounds comprising any aryl group in place of the specific aryl groups mentioned. In particular, where a specifically substituted phenyl group is mentioned as a substituent in a compound of this invention, it is to be understood that this invention is intended to encompass phenyl groups with other substituents selected from the list given above in place of the specific substituent(s) mentioned.

The term "arylalkyl" as used herein refers to an aryl group appended to a loweralkyl radical including, but limited to, benzyl, naphthylmethyl, 4-methoxybenzyl and the like.

The term "heterocyclic" or "heterocyclic group" as used herein refers to any 3-, 4-, 5- or 6-membered ring containing a heteroatom selected from oxygen, sulfur and nitrogen, or a 5- or 6-membered ring containing one, two or three nitrogen atoms; one nitrogen and one sulfur atom; or one nitrogen and one oxygen atom; wherein the nitrogen and sulfur heteroatoms can optionally be oxidized; wherein the nitrogen heteroatoms can optionally be quaternized; and wherein the 5-membered ring has 0-2 double bonds and the 6-membered ring has 0-3 double bonds. Heterocyclics also include any bicyclic group in which any of the above heterocyclic rings is fused to a benzene ring or another 5- or 6-membered heterocyclic ring independently defined as above. Heterocyclics include, but are not limited to, quinolyl, indolyl, benzofuryl, benzthienyl, imidazolyl, thiazolyl, benzoxazolyl, furyl, thienyl, pyridyl, pyrimidinyl, morpholinyl, piperazinyl, pyrrolidinyl, piperidinyl, pyrazinyl, pyrazolyl, thiomorpholinyl, isoquinolyl, indazolyl and the like. Where a specific heterocyclic group is mentioned as a substituent in a compound of this invention, it is to be understood that this invention is intended to encompass compounds comprising any heterocyclic group as defined above in place of the specific heterocyclic group mentioned.

Heterocyclics can be unsubstituted or substituted with one or two substituents independently selected from hydroxy, halo, amino, alkylamino, dialkylamino, alkoxy, thioalkoxy, formyl, alkanoyl, alkanoylamino, benzyl, loweralkyl, cycloalkyl and trihalomethyl.

The term "(heterocyclic)alkyl" as used herein refers to a heterocyclic group appended to a loweralkyl radical.

The term "glycosyl derivative of serine or threonine" as used herein refers to a serine or threonine residue which is bonded through its hydroxyl group (either alpha- or beta-glycosidically) to a glycosyl radical. Glycosyl radical are derived from a glycopyranose, glycofuranose or an oligosaccharide (all of which can be optionally protected). These glycosyl radicals are derived from D- or L-monosaccharides such as ribose, arabinose, xylose, lyxose, allose, altrose, glucose, mannose, gulose, idose, galactose, talose, erythrose, threose, psicose, fructose, sorbose, tagatose, xylulose, fucose, rhamnose, olivose, oliose, mycarose, rhodosamine, N-acetylglucosamine, N-acetylgalactosamine, N-acetylmannosamine; or disaccharides such as maltose, lactose, cellobiose, gentibiose, N-acetyllactosamine, chitobiose, beta-galactopyranosyl-(1,3)-N-acetylgalactosamine and beta-galactopyranosyl-(1,3)- or (1,4)-N-acetylglucosamine, as well as their synthetic derivatives, such as 2-deoxy, 2-amino, 2-acetamideo- or 2-halogeno derivatives.

Protecting groups for glycosyl radicals include those commonly used in carbohydrate chemistry including, but not limited to, $C_1$ to $C_{10}$ acyl groups (such as acetyl, benzoyl, trichloroacetyl and the like) and various ethers and acetals such as methyl ethers, methoxmethyl ethers, benzyl ethers, tetrahydropyranyl ethers, benzylidene acetals, isopropylidene acetals and trityl ethers.

Compounds of the invention include:

(4-9)[N-(1-Naphthylacetyl)-Ser$^4$ D Leu$^6$ Pro$^9$NHEt]LHRH;

(4-9)[N-(1-Naphthylacetyl)-Ser$^4$(OBzl) D-Leu$^6$-Pro$^9$NHEt]LHRH;

(4-9)[N-(1 Naphthylacetyl) Ser$^4$-D-Trp$^6$ Pro$^9$NHEt]LHRH;

(4-9)[N-(1 Naphthylpropionyl)-Ser$^4$-D Trp$^6$ Pro$^9$NHEt]LHRH;

(4-9)[N-(1-Naphthylpropionyl)-Ser$^4$(OBzl)-D Trp$^6$-Pro$^9$NHEt]LHRH;

(4-9)[N-(1 Naphthylpropionyl)-Ser$^4$-D-Arg$^6$ Pro$^9$NHEt]LHRH;

(4-9)[N-(2-Naphthylacetyl)-Ser$^4$-D-Arg$^6$ Pro$^9$NHEt]LHRH;

(4-9)[N-(1-Naphthylpropionyl)-Ser$^4$ D 2 Nal$^6$-Pro$^9$NHEt]LHRH;

(4-9)[N-(Phenylacetyl) Ser$^4$-D-Arg$^6$-Pro$^9$NHEt]LHRH;

(4-9)[N-(1-Naphthylacetyl)-Ser$^4$(OBzl) D 2-Nal$^6$-Pro$^9$NHEt]LHRH;

(4-9)[N-(3-Indolepropionyl)-Ser$^4$-D-Trp$^6$-Pro$^9$NHEt]LHRH;

(4-9)[N-(3 Indolepropionyl)-Ser$^4$-D-Arg$^6$-Pro$^9$NHEt]LHRH;

(4-9)[N-(1 Naphthylacetyl)-Ser$^4$-D-N-isp-Lys6-Pro$^9$NHEt]LHRH; (4-9)[N (3-Indolepropionyl) Ser$^4$ (2-(S 3-amino 2-oxo-pyrrolidin 1 yl) -S-2-isopropylmethylacetyl)$^{6,7}$ -Pro$^9$NHEt]LHRH;

(4-9)[N (1-Naphthylacetyl) Ser$^4$ (2 (S-3-aminno-2-oxo-pyrrolidin- 1-yl) -S-2-isopropylmethylacetyl)$^{6,7}$ -Pro$^9$NHEt]LHRH;

(4-9)[N-(1-Adamantylacetyl) Ser$^4$-N-Me-Tyr$^5$-D Trp$^6$ProNHEt]LHRH;

(4-10)[N-(1-Naphthylpropionyl)-Ser$^4$-D-2-Nal$^6$]LHRH;

(4-10)[N-(1 Naphthylpropionyl)-Ser$^4$-D-2 Nal$^6$-D-Ala$^{10}$]LHRH;

(4-10)[N-(1-Adamantylacetyl)-Ser$^4$-D-Trp$^6$-D-Ala$^{10}$]LHRH;

(3-9)[N-(N-alpha-morpholinecarbonyl)-1-Nal$^3$-D-Trp$^6$-Pro$^9$NHEt]LHRH;

(3-9)[N-(N-alpha-morpholinecarbonyl)-D-Trp$^3$-D-Tyr$^6$-Pro$^9$NHEt]LHRH;

(4-9)[N-[2-(1-Naphthylmethyl)-4-(morpholineamido)-succinyl]-Ser$^4$-D-Trp$^6$-Pro$^9$NHEt]LHRH;

(4-9)[N-[2-(1-(p-methoxybenzyl)) 4-(diethylamido)succinyl]-Ser$^4$-D-Trp$^6$-Pro$^9$NHEt]LHRH;

(4-9)[N-(3-Indolepropionyl-Ser$^4$-D-Tyr$^6$-Pro$^3$NHEt]LHRH;

(4-10)[N-(3-Indolepropionyl)-Ser$^4$-N-Me-Tyr$^5$-D-Trp$^6$-D-Ala$^{10}$]LHRH;

(4-9)[N-(3-(1-Naphthyl)propionyl)-Ser$^4$-N-Me-Tyr$^5$-D-2-Nal$^6$-Pro$^9$NHEt]LHRH;

(4-9)[N-(3-Indolepropionyl)-Ser$^4$ N Me-Tyr$^5$ D-Trp$^6$-Pro$^9$NHEt]LHRH;

(2-9)[N-(N-alpha-Morpholinocarbonyl)-Phe$^2$-D-Trp$^6$-Pro$^9$-NHEt]LHRH;

(2-10)[N-(N-alpha-Morpholinocarbonyl)-D-Phe$^2$-D-Trp$^3$-D-Arg$^6$-Pro$^9$-D-Ala$^{10}$]LHRH;

(2-10)[N-(N-alpha-Morpholinocarbonyl)-4-Cl-Phe$^2$-D-2 Nal$^6$-D-Ala$^{10}$]LHRH;

(2-10)[N-(N-alpha-Morpholinocarbonyl)-4-Cl-Phe$^2$-D-Trp$^3$-D-2-Nal$^6$-D-Ala$^{10}$]LHRH;

(2-9)[N-(N-alpha-Morpholinocarbonyl)-D-2-Nal$^2$-D-Trp$^6$-Pro$^9$NHEt]LHRH;

(2-10)[N-(N-alpha-Morpholinocarbonyl)-D-2 Nal$^2$-D-Tyr$^6$-D-Ala$^{10}$]LHRH;

(2-9)[N-(N-alpha-Morpholinocarbonyl)-2-Nal$^2$-1-Nal$^3$-D-Arg$^6$-Pro$^9$NHEt]LHRH;

(2-9)[N-(N-alpha-Morpholinocarbonyl)-4-F-Phe$^2$-D-3-Pal$^3$-D-Trp$^6$-Pro$^9$NHEt]LHRH;

(2-9)[N-(N-alpha-Morpholinocarbonyl)-1-Nal$^2$-D-Trp$^6$-Pro$^9$NHEt]LHRH;

2-9)[N-(N-alpha-Morpholinocarbonyl)-Phe$^2$-Nal$^3$-D-Trp$^6$-Pro$^9$NHEt]LHRH;

(2-9)[N-(N-alpha -Morpholinocarbonyl)-4-F-Phe$^2$-D-Trp$^{3,6}$-Pro$^9$NHEt]LHRH;

(2-9)[N-(N-alpha-Morpholinocarbonyl)-1-Nal$^2$-D-Trp$^{3,6}$-Pro$^9$NHEt]LHRH;

(2-10)[N-(N-alpha-Morpholinocarbonyl)-1-Nal$^2$-D-Trp$^{3,6}$-D-Ala$^{10}$]LHRH;

(2-10)[N-(N-alpha-Morpholinocarbonyl)-1-Nal$^2$ D Thia3-N-Me-Ser$^4$-N-Me-Tyr$^5$-D-Trp$^6$-D-Ala $^{10}$]LHRH;

(2-9)[N-(N-alpha-Piperidinocarbonyl)-D-Phe$^2$-D-Trp$^6$-Pro$^9$NHEt]LHRH;

(2-10)[N-(N-alpha piperidinocarbonyl)-Phe$^2$-D-Tyr$^6$-D-Ala$^{10}$]LHRH;

(2-9)[N-(N-alpha-Diethylaminocarbonyl)-Phe$^2$-D-Trp$^6$-Pro$^9$NHEt]LHRH;

(2 10)[N-(N-alpha-Diethylaminocarbonyl)-4-F-Phe$^2$-D-Tyr$^6$-D-Ala$^{10}$]LHRH;

(2-9)[N-(N-alpha-Cyclohexylaminocarbonyl)-Phe$^2$-D-Trp$^6$-Pro$^9$NHEt]LHRH;

(2-10)[N-(N-alpha-Morpholinocarbonyl)-1-Nal$^2$-D-Thia3-D-Trp$^6$-D-Ala$^{10}$]LHRH;

(2-10)[N-(N-alpha-Morpholinocarbonyl)-4-Cl-Phe$^2$-D Thia3-D-Trp$^6$-D-Ala$^{10}$]LHRH;

(2-10)[N-(N-alpha-Morpholinocarbonyl)-4-Cl-Phe$^2$-D Thia3-D-Lys6-D-Ala$^{10}$]LHRH;

(2-10)[N-(N-alpha-Morpholinocarbonyl)-1-Nal$^2$-D-Trp$^{3,6}$-N-Me-Tyr$^5$-D-Ala$^{10}$]LHRH;

(2-10)[N-(N-alpha-Cyclohexylaminocarbonyl)-D-4-Cl-Phe$^2$-D-Trp$^6$-D-Ala$^{10}$]LHRH;

(2-9)[N-(N-alpha-Morpholinocarbonyl)-Phe$^2$-N-Me-Tyr$^5$-D-Trp$^6$-Pro$^9$NHEt]LHRH;

(2-9)[N-(N-alpha-Morpholinocarbonyl)-4-Cl-Phe$^2$-N-Me-Ser$^4$-D-Trp$^6$-Pro$^9$NHEt]LHRH;

(2-9)[N-(N-alpha-Morpholinocarbonyl)-4-F-Phe$^2$-N-Me-Ser$^4$-D-Trp$^6$-N-Me-Leu7-Pro$^9$NHEt]LHRH;

(2-10)[N-(N-alpha-Cyclohexylaminocarbonyl)-D-4-Cl-Phe$^2$-N-Me-Tyr$^5$-D-Trp$^6$-DAla$^6$]LHRH;

(2-9)[N-(N-alpha-Morpholinocarbonyl)-Phe$^2$-N-Me-Trp$^3$-D-Tyr$^6$-Pro$^9$NHEt]LHRH;

(2-10)[N-(N-alpha-Morpholinocarbonyl)-Phe$^2$-D-Tyr$^6$-N-Me-Arg$^8$-D-Ala$^{10}$]LHRH;

(2-9)[N-(N-alpha-Cyclohexylaminocarbonyl)-Phe$^2$-N-Me Tyr$^5$-D-Trp$^6$-N-Leu$^7$-Pro$^9$NHEt]LHRH;

(3-9)[N-(3-(4-Imidazolyl)propionyl)-Trp$^3$-D-Trp$^6$-Pro$^9$-NHEt]LHRH;

(3-9)[N-(3-Phenylpropionyl)-Trp$^3$-D-Trp$^6$-Pro$^9$NHEt]LHRH;

(3-9)[N-(3 Phenylpropionyl)-D-Trp$^3$-D-Tyr$^6$-Pro$^9$NHEt]LHRH;

(3-9)[N-(Phenylacetyl)-Trp$^3$-D-Trp$^6$-Pro$^9$NHEt]LHRH;

(3-9)[N-(3-(4-Fluorophenyl)propionyl)-Trp$^3$-D-Trp$^6$-Pro$^9$NHEt]LHRH;

(3-9)[N-(3-(4-Chlorophenyl)propionyl)-Trp$^3$-D-Trp$^6$-Pro$^9$NHEt]LHRH;

(3-10)[3-(4-Chlorophenyl)propionyl)-D-Trp$^{3,6}$-D-Ala$^{10}$]LHRH;
(3-10)[N-(3-(4-Fluorophenyl)propionyl)-D-Trp$^{3,6}$-D-Ala]LHRH;
(3-10)[N-(3-(4-Chlorophenyl)propionyl)-D-Trp$^3$-D-Tyr$^6$-D-Ala$^{10}$]LHRH;
(3-10)[N-(3-(4 Fluorophenyl)propionyl)-Trp$^3$-D-Lys6-(N-epsilon-nicotinyl) -D-Ala$^{10}$]LHRH;
(3-9)[N-3-(2,4-difluorophenyl)propionyl)-D Thia3-N-Me-Tyr$^5$-D-Trp$^6$Pro$^9$NHEt]LHRH;
(3-9)[N-3-(4-Fluorophenyl)propionyl)-D-Trp$^{3,6}$ N-Me-Tyr$^5$-Cha$^7$-Pro$^9$NHEt]LHRH;
(3-10) [N-(4-Fluorophenylacetyl)-D-Trp$^3$-D-Trp$^6$-D-Ala$^{10}$]LHRH;
(3-9) [N-(4-Chlorophenylacetyl)-Trp$^3$-D-Trp$^6$-ProNHEt]LHRH;
(2-9)[N-(3-(4-Imidazolyl)propionyl)-Phe$^2$-D-Trp$^6$-Pro$^9$-NHEt]LHRH;
(2-9)[N-(Cyclopentylcarbonyl)-Phe$^2$-D-Arg$^6$-Pro$^9$-NHEt]LHRH;
(2-9)[N-Acetyl-Phe$^2$-D-Trp$^6$-Pro$^9$NHEt]LHRH;
(2-9)[N-5,6-Dihydro-4,5 -dimethyl-2-oxo-3-phenyl-1-(2H)-pyrazineacetyl]-His$^2$-D-Trp$^6$-Pro$^9$NHEt]LHRH;
(2-10)[N-(Cyclopentylcarbonyl)Phe$^2$-Lys$^5$(N-epsilon-nicotinyl)-D-Tyr$^6$-D-Ala$^{10}$]LHRH;
(2-9)[N-(Cyclohexylcarbonyl)-D-Phe$^2$-D-Trp$^3$-D-Tyr$^6$-Pro$^9$NHEt]LHRH;
(2-9)[N-Acetyl-(4-chloro)-Phe$^2$-D-Trp$^6$Pro$^9$NHEt]LHRH;
(2-9)[N-Isopropionyl-D-(4-fluoro)-Phe$^2$-D-Tyr$^6$ProNHEt]LHRH;
(3-9)[N-3-(4-fluorophenyl)propionyl D-Trp$^{3,6}$-Pro$^9$NHEt]LHRH;
(3-9)[N-3-(4-fluorophenyl)propionyl-D-Trp$^3$-D-Lys(-Nic)6-Pro$^9$NHEt]LHRH;
(3-9)[N-3-(4-fluorophenyl)propionyl)-D-Trp$^3$-D-2-Nal$^6$-Pro$^9$NHEt]LHRH;
(3-9)[N-3A-(4-chlorophenyl)propionyl-Trp$^3$-D-Trp$^6$-Pro$^9$NHE t]LHRH;
(3-9)[N-3-(4 fluorophenyl)propionyl-D-Trp$^{3,6}$ N-Me-Ser$^4$-Pro$^9$NHEt]LHRH;
(3-9)[N-3-(3-indole)propionyl-D-Trp$^{3,6}$-Pro$^9$NHEt]LHRH;
(3-9)[N-3-(4-fluorophenyl)propionyl-D-Trp$^{3,6}$-N-Me-Tyr$^5$-Pro$^9$NHEt]LHRH;
(3-9)[N 3-(4-fluorophenyl)propionyl-D-Trp$^3$-N-Me-Tyr$^5$-D-Lys(Nic)$^6$-Pro$^9$NHEt]LHRH;
(3-9)[N-3-(4-fluorophenyl)propionyl-D-Trp$^{3,6}$(N-indoleformyl)-D-Ala$^{10}$]LHRH;
(3-10)[N 3-(4-fluorophenyl)propionyl-D-Trp$^{3,6}$-N-Me-Tyr$^5$-D-Ala$^{10}$]LHRH;
(2-10)[N-3-(2-naphthyl)propionyl-D-4-Cl-Phe$^2$-D-Thia$^3$-D-Lys$^6$-D-Ala$^{10}$]LHRH;
N-(5-Fluoro-2-indolecarbonyl)-D-Trp-Ser-Tyr-D-Trp-Leu-Arg-ProNHEt;
(3-9) [N-(3-(4-Fluorophenyl)propionyl)-D-4-Cl-Phe$^3$-D-Trp$^6$-Pro$^9$NHEt]LHRH;
(3-9)[N-(3-(4-Fluorophenyl)propionyl)-D-Tyr$^3$-D-Trp$^6$-Pro$^9$NHEt]LHRH;
(3-9)[N-(3-(4-Fluorophenyl)propionyl))-5-F-Trp$^3$-D-Trp$^6$-Pro$^9$NHEt]LHRH;
(3-9)[N-(3-(4-Fluorophenyl)propionyl)-D-5-F-Trp$^3$-D-Trp$^6$-Pro$^9$NHEt]LHRH;
(3-9)[N-(3-(4-Fluorophenyl)propionyl)-1-Nal$^3$-D-Trp$^6$-Pro$^9$NHEt]LHRH;
(3-9)[N-(3-(4-Fluorophenyl)propionyl)-D-1-Nal$^3$-D-Trp$^6$-Pro$^9$NHEt]LHRH;
(3-9)[N-(3-(4-Fluorophenyl)propionyl)-D-Trp$^{3,6}$-6-OH-Pro$^4$-Pro$^9$-Pro$^9$NHEt]LHRH:
(3-9)[N-(3-(4-Fluorophenyl)propionyl)-D-Pro$^3$-D-Trp$^6$-Pro$^9$NHEt]LHRH;
(3-9)[N-(3-(4-Fluorophenyl)propionyl)-Pro$^3$-D-Trp$^6$-Pro$^9$NHEt]LHRH;
(3-9)[N-(3-(4-Fluorophenyl)propionyl)-D-Trp$^3$-D-4-Cl-Phe$^6$-Pro$^9$NHEt]LHRH;
(3-9)[N-(3-(4-Fluorophenyl)propionyl)-D-Trp$^3$-D-Tyr$^6$-Pro$^9$NHEt]LHRH;
(3-9)[N-(3-(3,4-diFluorophenyl)propionyl)-D-Trp$^{3,6}$-Pro$^9$NHEt]LHRH;
(3-9)[N-(3-(2,4-diFluorophenyl)propionyl)-D-Trp$^3$-NMeTyr$^5$-D-Lys$^6$(N-epsilon-nicotinyl)-Pro$^9$NHEt]LHRH;
(3-9)[N-(3-(3-Fluorophenyl)propionyl)-D-Trp$^3$-NMeTyr$^5$-D-Lys$^6$ (N-epsilon-nicotinyl)-Pro$^9$NHEt]LHRH;
(3-9)[N-(3-(4-Chlorophenyl)propionyl)-D-Trp$^3$-NMeTyr$^5$-D-Lys$^6$(N-epsilon-nicotinyl)-Pro$^9$NHEt]LHRH;
(3-9)[N-(3-(2,4-diFluorophenyl)propionyl)-D-Trp$^{3,6}$-NMeTyr$^5$-Pro$^9$NHEt]LHRH;
(3-9)[N-(3-(4-Chlorophenyl)propionyl)-D-Trp$^{3,6}$-NMeTyr$^5$-Pro$^9$NHEt]LHRH;
(3-9)[N-(3-(4-Fluorophenyl)propionyl)-D-1-Nal$^3$-NMeTyr$^5$-D-Trp$^6$-Pro$^9$NHEt]LHRH;
(3-9)[N-(3-(4-Fluorophenyl)propionyl)-1-Nal$^3$-NMeTyr$^5$-D-Trp$^6$-Pro$^9$NHEt]LHRH;
(3-9)[N-(3-(4-Bromophenyl)propionyl)-D-1-Nal$^3$-NMeTyr$^5$-D-Trp$^6$-Pro$^9$NHEt]LHRH;
(3-9)[N-(3-(4-Bromophenyl)propionyl)-1-Nal$^3$-NMeTyr$^5$-D-Trp$^6$-Pro$^9$NHEt]LHRH;
N-[3-(4-Fluorophenyl)propionyl]-D-Thia-Ser-NMeTyr-D-Lys (N-epsilon-nicotinyl)-Leu-Arg-Pro-D-AlaNH$_2$;
(3-10)[N-(3-(4-Fluorophenyl)propionyl)-D-Trp$^{3,6}$-D-Ala$^{10}$]LHRH;
(3-10) ]N-(3-(4-Fluorophenyl)propionyl)-D-Trp$^3$-NMeTyr$^5$-D-Lys$^6$(N-epsilon-nicotinyl)-D-Ala$^{10}$]LHRH;
(3-10)[N-(3-(4-Fluorophenyl)propionyl)-D-Thia$^3$-NMeTyr$^5$-D-Lys$^6$-D-Ala$^{10}$]LHRH;
(3-10)[N-(3-(4-Chlorophenyl)propionyl)-D-Thia$^3$-Ser-(O-Bzl)$^4$-D-Lys$^6$-D-Ala$^{10}$]LHRH;
(3-10)[N-(3-(4-Chlorophenyl)propionyl)-D-Thia$^3$-Ser-(O-Bzl)$^4$-NMeTyr$^5$-D-Lys$^6$-D-Ala$^{10}$ ]LHRH;
(3-10)[N-(3-(4-Fluorophenyl)propionyl)-D-1-Nal$^3$-NMeTyr$^5$-D-Lys$^6$-D-Ala$^{10}$]LHRH;
(3-10)[N-(3-(4-Fluorophenyl)propionyl)-D-3-Pa1$^3$-NMeTyr$^5$-D-Lys$^6$-D-Ala$^{10}$]LHRH;
(3-10)[N-(3-(4-Fluorophenyl)propionyl)-D-3-Pa1$^3$-NMeTyr$^5$-D-Lys$^6$(N-epsilon-nicotinyl)-D-Ala$^{10}$]LHRH;
(3-10)[N-(3-(4-Chlorophenyl)propionyl)-D-3-Pa1$^3$-Lys$^5$(N-epsilon-nicotinyl)-D-Lys$^6$(N-epsilon-nicotinyl)-D-Ala$^{10}$]LHRH;
(3-10) [N-(3-(4-Fluorophenyl)propionyl)-D-1-Nal$^3$-NMeTyr$^5$-D-Lys$^6$(N-epsilon-nicotinyl)-D-Ala$^{10}$]LHRH;
(3-10)[N-(3-(4-Fluorophenyl)propionyl)-D-4-Cl-Phe$^3$-NMeTyr$^5$-D-Lys$^6$-D-Ala$^{10}$]LHRH;
(3-10)[N-(3-(4-Fluorophenyl)propionyl)-D-1-Nal$^3$-hhPhe$^4$-NMeTyr$^5$-D-Lys$^6$-D-Ala $^{10}$]LHRH;
(3-10)[N-(3-(4-Fluorophenyl)propionyl)-D-3-Bal$^3$-NMeTyr$^5$-D-Lys$^6$-D-Ala$^{10}$]LHRH;
(3-10)[N-(3-(4-Fluorophenyl)propionyl)-D-1-Nal$^3$-NMeTyr$^5$-D-Hcit6-D-Ala$^{10}$]LHRH;

(3-10)[N-(3-(4-Fluorophenyl)propionyl)-D-1-Nal$^3$-NMeTyr$^5$-D-Lys$^6$-D-Ala$^{10}$]LHRH;

(3-10)[N-(3-(4-Fluorophenyl)propionyl)-1-Nal$^3$-NMeTyr$^5$-D-Ser$^6$-D-Ala$^{10}$]LHRH;

(3-10)[N-(3-(4-Fluorophenyl)propionyl)-D-1-Nal$^3$-NMeTyr$^5$-D-Ser6-D-Ala$^{10}$]LHRH;

(3-10)[N-(3-(4-Fluorophenyl)propionyl)-D-Trp$^3$-NMeTyr$^5$-D-Lys$^6$-D-Ala$^{10}$]LHRH;

(3-10)[N-(3-(4-Fluorophenyl)propionyl)-D-Thiaz3-NMeTyr$^5$-D-Lys$^6$-D-Ala$^{10}$]LHRH;

(3-10)[N-(3-(4-Fluorophenyl)propionyl)-D-3-Pal3-NMeTyr$^5$-D-Lys$^6$-D-Ala$^{10}$]LHRH;

(3-10)[N-(3-(4-Fluorophenyl)propionyl)-D-1-Nal$^3$-NMeTyr$^5$-D-Lys$^6$-Cha7-D-Ala$^{10}$]LHRH;

(3-10)[N-(3-(4-Fluorophenyl)propionyl)-D-2-Nal$^3$-NMeTyr$^5$-D-Ser6(O-PO$_3$Me$_2$)-D-Ala$^{10}$]LHRH;

(3-10) [N-(3-(4-(Fluorophenyl)propionyl)-D-2-Nal$^3$-NMeTyr$^5$-D-Lys$^6$ (N-epsilon-nicotinyl)-D-Ala$^{10}$]LHRH;

(3-10)[N-(3-(4-Fluorophenyl)propionyl)-D-1-Nal$^3$Tyr$^5$-(OMe) -D-Lys$^6$-D-Ala$^{10}$]LHRH;

(3-10)[N-(3-(4-Fluorophenyl)propionyl)-D-2-Nal$^3$-NMePhe$^5$-D-Lys$^6$-D-Ala$^{10}$]LHRH;

(3-10)[N-(3-(4-Fluorophenyl)propionyl)-D-1-Nal$^3$-NMeTyr$^5$-D-Lys$^6$-NMeLeu$^7$-D-Ala $^{10}$]LHRH;

(3-10)[N-(3-(4-Fluorophenyl)propionyl)-D-1-Nal$^3$-Lys$^5$(N-epsilon-nicotinyl)-D-Lys$^6$(N-epsilon-nicotinyl)-D-Ala$^{10}$]LHRH;

(3-10)[N-(3-(4-Fluorophenyl)propionyl)-D-1-Nal$^3$-NMeTyr$^5$-D-Orn$^6$-D-Ala$^{10}$]LHRH;

(3-10)[N-(3-(4-Fluorophenyl)propionyl)-D-3-Pal$^3$-Lys$^5$(N-epsilon-nicotinyl)-D-Lys$^6$(N-epsilon-nicotinyl)-Lys$^8$(N-epsilon-isopropyl)-D-Ala$^{10}$]LHRH;

(3-10)[N-(3-(4-Chlorophenyl)propionyl)-D-3-Pal$^3$-NMeTyr$^5$-D-Lys$^6$(N-epsilon-nicotinyl)-Lys$^8$(N-epsilon-isopropyl)-D-Ala$^{10}$]LHRH;

(3-10)[N-(3-(4-Fluorophenyl)propionyl)-D-Trp$^3$-NMeTyr$^5$-D-Lys$^6$(N-epsilon-nicotinyl)-Lys$^8$(N-epsilon-isopropyl)-D-Ala$^{10}$]LHRH;

(3-10)[N-(3-(4-Fluorophenyl)propionyl)-D-Trp$^3$-NMeTyr$^5$-D-Tyr$^6$-Lys$^8$(N-epsilon-isopropyl)-D-Ala$^{10}$]LHRH;

(3-10)[N-(3-(4-Fluorophenyl)propionyl)-D-1-Nal$^3$-NMeTyr$^5$-D-Lys$^6$(N-epsilon-nicotinyl)-Lys$^8$(N-epsilon-isopropyl)-D-Ala$^{10}$]LHRH;

(3-10)[N-(3-(4-Fluorophenyl)propionyl)-D-3-Bal$^3$-NMeTyr$^5$-D-Lys$^6$(N-epsilon-isopropyl)-D-Ala$^{10}$]LHRH;

(3-10)[N-(3-(4-Fluorophenyl)propionyl)-D-1-Nal$^3$-NMeTyr$^5$-D-Lys$^6$-Lys$^8$(N-epsilon-isopropyl)-D-Ala$^{10}$]LHRH;

(3-10)[N-(3-(4-Fluorophenyl)propionyl)-D-1-Nal$^3$-Tyr$^5$(OMe)-D-Lys$^6$(N-epsilon-nicotinyl)-Lys$^8$(N-epsilon-isopropyl)-D-Ala$^{10}$]LHRH;

(3-10)[N-(3-(4-Fluorophenyl)propionyl)-D-1-Nal$^3$-D-3-Pal$^6$-Lys$^8$(N-epsilon-isopropyl)-D-Ala$^{10}$]LHRH;

(3-10)[N-(3-(4-Fluorophenyl)propionyl)-D-1-Nal$^3$-Ser$^4$-(O-Bzl)-D-3-Pal$^6$-Lys$^8$(N-epsilon-isopropyl)-D-Ala$^{10}$]LHRH;

(3-10)[N-(3-(4-Fluorophenyl)propionyl)-D-1-Nal$^3$-Tyr$^5$(OMe)-D-Lys$^6$(N-epsilon-2-pyrazinylcarbonyl)-Lys$^8$(N-epsilon-isopropyl)-D-Ala$^{10}$]LHRH;

(3-10)[N-(3-(4-Fluorophenyl)propionyl)-D-1-Nal$^3$-NMeTyr$^5$-D-Thiaz6-Lys$^8$(N-epsilon-isopropyl)-D-Ala$^{10}$]LHRH;

(3-10)[N-(3-(4-Fluorophenyl)propionyl)-D-1-Nal$^3$-NMePhe$^5$-D-Lys$^6$(N-epsilon-nicotinyl)-D-Ala$^{10}$]LHRH;

(3-10)[N-(3-(4-Fluorophenyl)propionyl)-D-1-Nal$^3$-D-Lys$^6$ (N-epsilon-4-methoxybenzoyl)-Lys$^8$(N-epsilon-isopropyl)-D-Ala$^{10}$]LHRH;

(3-10)[N-(3-(4-Fluorophenyl)propionyl)-D-1-Nal$^3$-NMeTyr$^5$-D-Lys$^6$(N-epsilon-2-pyrazinylcarbonyl)-Lys$^8$(N-epsilon-isopropyl)-D-Ala$^{10}$]LHRH;

(3-10)[N-(3-(4-Fluorophenyl)propionyl)-D-1-Nal$^3$-NMeTyr$^5$-D-3-Pal$^6$-Lys$^8$(N-epsilon-isopropyl)-D-Ala$^{10}$]LHRH;

N-(3-(4-Fluorophenyl)propionyl)-D-1-Nal-Ser-NMeTyr-D-Lys (N-epsilon-morpholinecarbonyl)-Leu-Arg-Pro-D-AlaNH$_2$;

N-(3-(4-Fluorophenyl)propionyl)-D-1-Nal-Ser-NMeTyr-D-Lys (N-epsilon-N'-N''-methylpiperazinecarbonyl)-Leu-Arg-Pro-D-AlaNH$_2$;

N-(3-(4-Fluorophenyl)propionyl)-D-1-Nal-Ser-Lys(N-epsilon-hydrazinecarbonyl) -D-Lys(N-epsilon-nicotinyl)-Leu-Arg-Pro-D-AlaNH$_2$;

N-(3-(4-Fluorophenyl)propionyl)-D-1-Nal-Ser-NMeTyr-D-Lys (N-epsilon-morpholinecarbonyl)-Leu-Lys(N-epsilon-isopropyl)-Pro-D-AlaNH$_2$;

N-(3-Chloro-4-Fluorobenzoyl)-Lys(N-epsilon-acetyl)-D-1-Nal-Ser-NMeTyr-D-Lys-Leu-Arg-Pro-D-AlaNH$_2$;

N-(4-Fluorobenzoyl)-Orn(N-delta-acetyl)-D-1-Nal-Ser-NMeTyr-D-Thiaz-Leu-Lys (N-epsilon-isopropyl)-Pro-D-AlaNH$_2$;

N-(4-Fluorobenzoyl)-Orn(N-delta-acetyl)-D-1-Nal-Ser-Tyr-D-Lys-Leu-Arg-Pro-D-AlaNH$_2$;

N-(4-Fluorobenzoyl)-Orn(N-delta-acetyl)-D-1-Nal-Ser-Tyr-D-Lys (N-epsilon-nicotinyl)-Leu-Arg-Pro-D-AlaNH$_2$;

N-(4-Fluorobenzoyl)-Orn(N-delta-acetyl)-D-1-Nal-Ser-NMeTyr-D-Lys (N-epsilon-nicotinyl)-Leu-Lys(N-epsilon-isopropyl)-Pro-D-AlaNH$_2$;

(2-10)[N-(alpha-Morpholinocarbonyl)-D-1-Nal$^2$-D-Trp$^{3,6}$-NMeTyr$^5$-D-Ala$^{10}$]LHRH;

N-(3-(4-Fluorophenyl)propionyl)-D-1-Nal-Ser(O-alpha-L-Rha)-NMeTyr-D-Lys (N-epsilon-nicotinyl)-Leu-Lys(N-epsilon-isopropyl)-Pro-D-AlaNH$_2$;

N-(3-(4-Fluorophenyl)propionyl)-D-1-Nal-Ser(O-PO$_3$H$_2$)-NMeTyr-D-Lys (N-epsilon-nicotinyl)-Leu-Lys(N-epsilon-isopropyl)-Pro-D-AlaNH$_2$;

N-(3-(4-Fluorophenyl)propionyl)-D-1-Nal-Ser-NMeTyr(O-PO$_3$H$_2$)-D-Lys (N-epsilon-nicotinyl)-Leu-Lys(N-epsilon-isopropyl)-Pro-D-AlaNH$_2$;

(2-10)[N-(alpha-Morpholinocarbonyl)-Phe$^2$-D-Trp$^3$-NMeTyr$^5$-D-Tyr$^6$-D-Ala$^{10}$]LHRH;

(2-10)[N-(alpha-Morpholinocarbonyl)-1-Nal$^2$-D-Trp$^6$-D-Ala$^{10}$]LHRH;

(2-10)[N-(alpha-Morpholinocarbonyl)-Phe$^2$-D-Thia$^3$-D-Lys$^6$-D-Ala$^{10}$]LHRH;

(2-10)[N-(alpha-Morpholinocarbonyl)-Phe$^2$-D-Thia$^3$-D-Lys$^6$(N-epsilon-niCotinyl)-D-Ala$^{10}$]LHRH;

(2-10)[N-(alpha-Morpholinocarbonyl)-Phe$^2$-D-Thia$^3$-NMeTyr$^5$-D-Lys$^6$-D-Ala$^{10}$]LHRH;

(2-10)[N-(alpha-Morpholinocarbonyl)-Phe$^2$-D-Thia$^3$-NMeTyr$^5$-D-Lys$^6$(N-epsilon-nicotinyl)-D-Ala$^{10}$]LHRH;

(2-10)[N-(alpha-Morpholinocarbonyl)-D-4-Cl-Phe$^2$-D-Thia$^3$-D-Lys$^6$-D-Ala$^{10}$]LHRH;

N-(alpha-phenethylaminocarbonyl)-Phe-D-Trp-Ser-NMeTyr-D-Tyr-Leu-Arg-Pro-D-AlaNH$_2$;

N-(alpha-phenethylaminocarbonyl)-D-Phe-D-Trp-Ser-NMeTyr-D-Trp-Leu-Arg-Pro-D-AlaNH$_2$;

N-(alpha-phenethylaminocarbonyl)-Phe-D-Trp-Ser-NMeTyr-D-Trp-Leu-Arg-Pro-D-AlaNH$_2$;

(2-9) [N-(alpha-Morpholinocarbonyl)-D-Thia$^3$-D-Trp$^6$-Pro$^9$NHEt]LHRH;

(2-9) [N-(alpha-Morpholinocarbonyl)-1-Nal$^3$-D-Trp$^6$-Pro$^9$NHEt]LHRH;

(2-9)[N-(alpha-Ethylaminocarbonyl)-D-1-Nal$^3$-D-Trp$^6$-Pro$^9$NHEt]LHRH;

(2-9)[N-(alpha-Ethylaminocarbonyl)-1-Nal$^3$-D-Trp$^6$-Pro$^9$NHEt]LHRH;

(3-10)[N-(3-(4-Fluorophenyl)propionyl)-D-Nal$^3$-N-MeTyr$^5$-D-Lys$^6$(N-epsilon-nicotinyl)-Ser$^7$(O-alpha-L-Rha)-Lys$^8$(N-epsilon-isopropyl)-D-Ala$^{10}$]LHRH;

(3-10)[N-(3-(4-Fluorophenyl)propionyl)-D-Nal$^3$-NMeTyr$^5$-D-Lys$^6$(N-epsilon-nicotinyl)-Ser$^7$(O-PO$_3$H$_2$)-Lys$^8$(N-epsilon-isopropyl)-D-Ala$^{10}$]LHRH;

(3-10)[N-(3-(4-Fluorophenyl)propionyl)-D-Nal$^3$-NMeTyr$^5$-D-Lys$^6$(N-epsilon-nicotinyl)-Ser$^7$(O-PO$_3$Me$_2$)-Lys$^8$(N-epsilon-isopropyl)-D-Ala$^{10}$]LHRH;

N-(alpha-4-Cl-Phenethylaminocarbonyl)-D-4-Cl-Phe-D-Thia-Ser-Tyr-D-Lys-Leu-Arg-Pro-D-AlaNH$_2$;

N-(alpha-4-Cl-Phenethylaminocarbonyl)-D-4-Cl-Phe-D-Thia-Ser-NMeTyr-D-Lys-Leu-Arg-Pro-D-AlaNH$_2$;

N-(3-(4-Chlorophenyl)propionyl)-D-4-Cl-Phe-D-Thia-Ser-Tyr-D-Lys-Leu-Arg-Pro-D-AlaNH$_2$;

N-(3-(2-Naphthyl)propionyl)-D-4-Cl-Phe-D-3-Pal-Ser-NMeTyr-D-Lys (N-epsilon-nicotinyl)-Leu-Lys(N-epsilon-isopropyl)-Pro-D-AlaNH$_2$;

N-(3-(2-Naphthyl)propionyl)-D-4-Cl-Phe-D-3-Pal-Ser-Lys (N-epsilon-nicotinyl)-D-Lys(N-epsilon-nicotinyl)-Leu-Lys(N-epsilon-isopropyl)-Pro-D-AlaNH$_2$;

N-(3-(4-Chlorophenyl)propionyl)-D-4-Cl-Phe-D-3-Pal-Ser-NMeTyr-D-Lys (N-epsilon-nicotinyl)-Leu-Lys(N-epsilon-isopropyl)-Pro-D-AlaNH$_2$;

N-(3-(4-Fluorophenyl)propionyl)-D-4-Cl-Phe-D-Thia-Ser-NMeTyr-D-Lys-Leu-Arg-Pro-D-AlaNH$_2$;

N-(3-(4-Chlorophenyl)propionyl)-D-4-Cl-Phe-D-1-Nal-Ser-Tyr-D-Lys-Leu-Arg-Pro-D-AlaNH$_2$;

N-(3-(4-Chlorophenyl)propionyl)-D-4-Cl-Phe-NMe-D-1-Nal-Ser-Tyr-D-Lys-Leu-Arg-Pro-D-AlaNH$_2$;

(3-10)[N-(3-(4-Fluorophenyl)propionyl)-D-1-Nal$^3$-Phe$^5$-D-Lys$^6$(N-epsilon-nicotinyl)-Lys$^8$(N-epsilon-isopropyl)-D-Ala$^{10}$]LHRH;

(3-10)[N-(3-(4-Fluorophenyl)propionyl)-D-3-Bal$^3$-NMeTyr$^5$-D-Lys$^6$(N-epsilon-nicotinyl)-Lys$^8$(N-epsilon-isopropyl)-D-Ala$^{10}$]LHRH;

(3-10)[N-(3-(4-Fluorophenyl)propionyl)-D-Cha$^3$-NMeTyr$^5$-D-Lys$^6$(N-epsilon-nicotinyl)-Lys$^8$(N-epsilon-isopropyl)-D-Ala$^{10}$]LHRH;

N-(3-(4-Fluorophenyl)propionyl)-D-1-Nal-Ser-NMeTyr-D-Lys (N-epsilon-nicotinyl)-Leu-Lys(N-epsilon-isopropyl)-Pro-SarNH$_2$;

N-(3-(4-Fluorophenyl)propionyl)-D-1-Nal-Ser-NMeTyr-D-Ser (O-alpha-L-Rha)-Leu-Lys(N-epsilon-isopropyl)-Pro-D-AlaNH$_2$;

N-(3-(4-Fluorophenyl)propionyl)-D-1-Nal-Ser-NMeTyr-D-Lys (N-epsilon-nicotinyl)-Leu-Lys(N-epsilon-isopropyl)-Pro-azaGlyNH$_2$;

N-(3-(4-Fluorophenyl)propionyl)-D-1-Nal-Ser-NMeTyr(OMe)-D-Lys (N-epsilon-nicotinyl)-Leu-Lys(N-epsilon-isopropyl)-Pro-D-AlaNH$_2$;

N-(3-(4-fluorophenyl)propionyl)-D-3-(3-benzthienyl) alanyl-seryl-N-alpha-methyl-tyrosyl(O-methyl)-D-lysyl (N-epsilon-nicotinyl)-leucyl-lysyl(N-epsilon-isopropyl)-prolyl-D-alanylamide;

N-(3-(4-fluorophenyl)propionyl)-D-3-(2-thienyl)alanyl-seryl-N-alpha-methyl-tyrosyl (O-methyl)-D-lysyl(N-epsilon-nicotinyl)-leucyl-lysyl(N-epsilon-isopropyl)-prolyl-D-alanylamide;

N-(3-(4-fluorophenyl)propionyl)-D-tryptyl(N-indoleformyl)-seryl-N-alpha-methyl-tyrosyl (O-methyl)-D-lysyl (N-epsilon-nicotinyl)-leucyl-lysyl(N-epsilon-isopropyl)-prolyl-D-alanylamide;

N-(3-(4-fluorophenyl)propionyl)-D-4-chloro-phenylalanylseryl-N-alpha-methyl-tyrosyl (O-methyl)-D-lysyl(N-epsilon-nicotinyl)-leucyl-lysyl (N-epsilon-isopropyl)-prolyl-D-alanylamide;

N-(3-(4-fluorophenyl)propionyl)-D-3-(2-naphthyl)alanyl-seryl-N-alpha-methyl-tyrosyl (O-methyl)-D-lysyl(N-epsilon-nicotinyl)-leucyl-lysyl (N-epsilon-isopropyl)-prolyl-D-alanylamide;

N-(3-(4-fluorophenyl)propionyl)-D-phenylalanyl-seryl-N-alpha-methyl-tyrosyl (O-methyl)-D-lysyl(N-epsilon-nicotinyl)-leucyl-lysyl (N-epsilon-isopropyl)-Prolyl-D-alanylamide;

N-(3-(4-fluorophenyl)propionyl)-D-tyrosyl(O-methyl)-seryl-N-alpha-methyl-tyrosyl (O-methyl)-D-lysyl(N-epsilon-nicotinyl)-leucyl-lysyl (N-epsilon-isopropyl)-prolyl-D-alanylamide;

N-(3-(4-fluorophenyl)propionyl)-D-(4-methylphenyl) alanyl-seryl-N-alpha-methyl-tyrosyl(O-methyl)-D-lysyl (N-epsilon-nicotinyl)-leucyl-lysyl(N-epsilon-isopropyl)-prolyl-D-alanylamide;

N-(3-(4-fluorophenyl)propionyl)-D-3-(cyclohexyl)alanyl-seryl-N-alpha-methyl-tyrosyl (O-methyl)-D-lysyl(N-epsilon-nicotinyl)-leucyl-lysyl (N-epsilon-isopropyl)-prolyl-D-alanylamide;

N-(3-(4-fluorophenyl)propionyl)-D-3-(3,4,5-trimethylphenyl) alanyl-seryl-N-alpha-methyl-tyrosyl(O-methyl)-D-lysyl (N-epsilon-nicotinyl)-leucyl-lysyl(N-epsilon-isopropyl)-prolyl-D-alanylamide;

N-(3-(4-fluorophenyl)propionyl)-D-3-(pentamethylphenyl) alanyl-seryl-N-alpha-methyl-tyrosyl(O-methyl)-D-lysyl (N-epsilon-nicotinyl)-leucyl-lysyl (N-epsilon-isopropyl)-Prolyl-D-alanylamide;

N-(3-(4-fluorophenyl)propionyl)-D-tryptyl(N-indolemethyl)-seryl-N-alpha-methyl-tyrosyl (O-methyl)-D-lysyl (N-epsilon-nicotinyl)-leucyl-lysyl(N-epsilon-isopropyl)-prolyl-D-alanylamide;

N-(3-(4-fluorophenyl)propionyl)-D-3-(biphenyl)alanyl-seryl-N-alpha-methyl-tyrosyl (O-methyl)-D-lysyl(N-epsilon-nicotinyl)-leucyl-lysyl (N-epsilon-isopropyl)-prolyl-D-alanylamide;

N-(3-(4-fluorophenyl)propionyl)-D-3-(7-methyl)tryptyl-seryl-N-alpha-methyl-tyrosyl (O-methyl)-D-lysyl(N-epsilon-nicotinyl)-leucyl-lysyl(N-epsilon-isopropyl)prolyl-D-alanylamide;

N-(3-(4-fluorophenyl)propionyl)-D-3-(4-methyl)tryptyl-seryl-N-alpha-methyl-tyrosyl (O-methyl)-D-lysyl(N-epsilon-nicotinyl)-leucyl-lysyl (N-epsilon-isopropyl)prolyl-D-alanylamide;

N-(3-(4-fluorophenyl)propionyl)-D-3-(1-adamantyl)alanyl-seryl-N-alpha-methyl-tyrosyl (O-methyl)-D-lysyl(N-epsilon-nicotinyl)-leucyl-lysyl (N-epsilon-isopropyl)prolyl-D-alanylamide;

N-(3-(4-fluorophenyl)propionyl)-D-3-(1-naphthyl)alanyl-threonyl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-3-(1-naphthyl)alanyl-alanyl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-3-(1-naphthyl)alanyl-glutaminyl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-4-chlorophenylalanyl-D-lysyl(N-epsilon-nicotinyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-4-fluorophenylalanyl-D-lysyl(N-epsilon-nicotinyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-3-cyclohexylalanyl-D-lysyl(N-epsilon-nicotinyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl (O-ethyl)-D-lysyl(N-epsilon-nicotinyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-histidinyl-D-lysyl (N-epsilon-nicotinyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-arginyl-D-lysyl (N-epsilon-nicotinyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-arginyl (N,N-guanidine-diethyl)-D-lysyl (N-epsilon-nicotinyl)-leucyl-lysyl(N-epsilon-isopropyl)-prolyl-D-alanylamide;

N-(3-(4-fluorophenyl)propionyl)-D-3-(1-naphthyl)alanyl-seryl-N-alpha-methyl-citrullinyl-D-lysyl (N-epsilon-nicotinyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-(4-aminophenyl) alanyl-D-lysyl(N-epsilon-nicotinyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-(4-nitrophenyl) alanyl-D-lysyl(N-epsilon-nicotinyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-(4-aminoacetylphenyl) alanyl-D-lysyl (N-epsilon-nicotinyl)-leucyl-lysyl(N-epsilon-isopropyl)-prolyl-D-alanylamide;

N-(3-(4-fluorophenyl)propionyl)-D-3-(1-naphthyl)alanyl-seryl-N-alpha-methyl-lysyl (N-epsilon-nicotinyl)-D-lysyl (N-epsilon-nicotinyl)-leucyl-lysyl(N-epsilon-isopropyl)-prolyl-D-alanylamide;

N-(3-(4-fluorophenyl)propionyl)-D-tryptyl(N-indoleformyl)-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-3-(2-thienyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-tryptyl(N-indolemethyl)-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-(2-methyl)tryptyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-(7-methyl)tryptyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-(4-methyl)tryptyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-(5-fluoro)tryptyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-(6-fluoro)tryptyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-3-(4-chlorophenyl) alanyl-seryl-N-alpha-methyl-tyrosyl-D-lysyl (N-epsilon-nicotinyl)-leucyl-lysyl(N-epsilon-isopropyl)-prolyl-D-alanylamide;

N-(3-(4-fluorophenyl)propionyl)-D-3-(2-naphthyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-phenylalanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-tyrosyl(O-methyl)-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-3-(4-methylphenyl) alanyl-seryl-N-alpha-methyl-tyrosyl-D-lysyl (N-epsilon-nicotinyl)-leucyl-lysyl(N-epsilon-isopropyl)-prolyl-D-alanylamide;

N-(3-(4-fluorophenyl)propionyl)-D-3-(3,4,5-trimethylphenyl) alanyl-seryl-N-alpha-methyl-tyrosyl-D-lysyl (N-epsilon-nicotinyl)-leucyl-lysyl(N-epsilon-isopropyl)-prolyl-D-alanylamide;

N-(3-(4-fluorophenyl)propionyl)-D-3-(pentamethylphenyl) alanyl-seryl-N-alpha-methyl-tyrosyl-D-lysyl (N-epsilon-nicotinyl)-leucyl-lysyl(N-epsilon-isopropyl)-prolyl-D-alanylamide;

N-(3-(4-fluorophenyl)propionyl)-D-3-(biphenyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-3-(1-adamantyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-3-indolecarbonyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-2-indolecarbonyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-3-quinolinecarbonyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-lysyl (N-epsilon-2-pyridinecarbonyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-lysyl (N-epsilon-(3-pyridine)acetyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-lysyl (N-epsilon-(4-methoxyphenyl) acetyl)-leucyl-lysyl(N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-lysyl (N-epsilon-3-methoxybenzoyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl-N'-oxide)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-lysyl (N-epsilon-2-methyl-nicotinyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-6-methyl-nicotinyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-ornithyl (N-delta-nicotinyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-ornithyl (N-delta-3-indolecarbonyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-ornithyl (N-delta-2-indolecarbonyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-ornithyl (N-delta-3-quinolinecarbonyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-ornithyl (N-delta-2-pyridinecarbonyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-ornithyl (N-delta-(3-pyridine)acetyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-ornithyl (N-delta-(4-methoxyphenyl)acetyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-ornithyl (N-delta-3-methoxybenzoyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-ornithyl (N-delta-nicotinyl-N'-oxide)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-ornithyl (N-delta-2-methylnicotinyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-ornithyl (N-delta-6-methylnicotinyl)-leucyl-lysyl (N-epsilon-isopropyl)prolyl-D-alanylamide;

N-(3-(4-Fluorophenyl)propionyl)-D-1-Nal-Ser-NMeTyr-D-Lys(N-epsilon-hyrdazinecarbonyl)-Leu-Lys(N-epsilon; isopropyl)-Pro-D-AlaNH$_2$;

N-(3-(4-Fluorophenyl)propionyl)-D-1-Nal-Ser-NMeTyr-D-Lys (N-epsilon-(N'-acetyl-alpha-azaglycyl))-Leu-Lys(N-epsilon-isopropyl)-Pro-D-AlaNH$_2$;

N-(3-(4-Fluorophenyl)propionyl)-D-1-Nal-Ser-NMeTyr-D-Lys (N-epsilon-3-aminopyridinecarbonyl)-Leu-Lys(N-epsilon-isopropyl)-Pro-D-AlaNH$_2$;

N-(3-(4-fluorophenyl)propionyl)-D-3-(1-naphthyl)alanyl-seryl-N-alpha-methyl-tyrosyl-D-lysyl (N-epsilon-N'-acetylpiperazinecarbonyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-pyrrolidinocarbonyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-lysyl (N-epsilon-piperidinocarbonyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-lysyl (N-epsilon-diethylaminocarbonyl)-leucyl-lysyl (N-epsilon-isopropyl)prolyl-D-alanylamide;

N-(3-(4-fluorophenyl)propionyl)-D-3-(1-naphthyl)alanyl-seryl-N-alpha-methyl-tyrosyl-D-lysyl (N-epsilon-(4-methoxyanilinocarbonyl)-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-(3-cyclohexyl) alanyl-lysyl(N-epsilonisopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-seryl-lysyl (N-epsilon-isopropyl)-prolyl-D-alanylamide; N-(3-(4-fluorophenyl)propionyl)-D-3-(1-naphthyl)alanyl-seryl-N-alpha-methyl-tyrosyl-D-lysyl (N-epsilon-nicotinyl)-threonyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-norleucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-phenylalanyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-methionyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-tryptyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-seryl (O-alpha-L-Rha)-lysyl(N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-N-alpha-methyl-leucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilonnicotinyl)-N-alpha-methyl-(3-cyclohexyl) alanyl-lysyl(N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-N-alpha-methyl-norleucyl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-N-alpha-methyl-seryl-lysyl (N-epsilon-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-seryl(O-PO$_3$H$_2$)-lysyl (N-epsilon-isopropyl)nicotiny prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-leucyl-ornithyl (N-delta-isopropyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-leucyl-lysyl (N-epsilon-cyclohexyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-leucyl-lysyl (N-epsilon-propyl)-prolyl-D-alanylamide;

N-(3-(4-fluorophenyl)propionyl)-D-3-(1-naphthyl)alanyl-nicotinyl)-leucyl-lysyl (N-epsilon-diethyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-leucyl-lysyl (N-epsilon-cyclopentyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-leucyl-lysyl (N-epsilon-cycloheptyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-leucyl-lysyl (N-epsilon-methyl)-prolyl-D-alanylamide;

N-(3-(4-fluorophenyl)propionyl)-D-3-(1-naphthyl)alanyl-seryl-N-alpha-methyl-tyrosyl-D-lysyl (N-epsilon-nicotinyl)-leucyl-lysyl (N,N-epsilon-dimethyl)-prolyl-D-alanylamide;

N-(3-(4-Fluorophenyl)propionyl)-D-1-Nal-Ser-NMeTyr-D-Lys (N-epsilon-nicotinyl)-Leu-Hcit-Pro-D-AlaNH$_2$;

N-(3-(4-Fluorophenyl)propionyl)-D-1-Nal-Ser-NMeTyr-D-Lys (N-epsilon-nicotinyl)-Leu-Cit-Pro-D-AlaNH$_2$;

N-(3-(4-Fluorophenyl)propionyl)-D-1-Nal-Ser-NMeTyr-D-Lys (N-epsilon-nicotinyl)-Leu-Arg(Ng-diethyl)-Pro-D-AlaNH$_2$;

N-(3-(4-Fluorophenyl)propionyl)-D-1-Nal-Ser-NMeTyr-D-Arg (N$^g$-diethyl)-Leu-Arg(N9-diethyl)-Pro-D-AlaNH$_2$;

N-(3-(4-Fluorophenyl)propionyl)-D-1-Nal-Ser-NMeTyr-D-Lys (N-epsilon-nicotinyl)-Leu-Arg(N9-amino)-Pro-D-AlaNH$_2$;

N-(3-(4-Fluorophenyl)propionyl)-D-1-Nal-Ser-NMeTyr-D-Lys (N-epsilon-nicotinyl)-Leu-Hcit(Nu-amino)-Pro-D-AlaNH$_2$;

N-(3-(4-Fluorophenyl)propionyl)-D-1-Nal-Ser-NMeTyr-D-Lys (N-epsilon-nicotinyl)-Leu-Harg(Ng-methyl-Ng-cyano)-Pro-D-AlaNH$_2$;

N-(3-(4-Fluorophenyl)propionyl)-D-1-Nal-Ser-NMeTyr-D-Lys (N-epsilon-nicotinyl)-Leu-Lys(N-epsilon-diisopropyl)-Pro-D-AlaNH$_2$;

N-(3-(4-Fluorophenyl)propionyl)-D-1-Nal-Ser-NMeTyr-D-Lys (N-epsilon-nicotinyl)-Leu-Orn(N-delta-diisopropyl)-Pro-D-AlaNH$_2$;

N-(3-(4-Fluorophenyl)propionyl)-D-1-Nal-Ser-NMeTyr-D-piperazinecarbonyl)-Pro-D-AlaNH$_2$;

N-(3-(4-Fluorophenyl)propionyl)-D-1-Nal-Ser-NMeTyr-D-Lys (N-epsilon-nicotinyl)-Leu-Lys(N-epsilon-morpholinecarbonyl)-Pro-D-AlaNH$_2$;

N-(3-(4-Fluorophenyl)propionyl)-D-1-Nal-Ser-NMeArg-D-4-(4-methoxybenzoyl) -Homoala-Leu-Arg-Pro-D-AlaNH$_2$;

N-(3-(4-Fluorophenyl)propionyl)-D-1-Nal-Ser-NMeTyr-D-Lys (N-epsilon-nicotinyl)-Leu-NMeArg-Pro-D-AlaNH$_2$;

N-(3-(4-Fluorophenyl)propionyl)-D-1-Nal-NMeSer-Tyr-D-Lys -Leu-Arg-Pro-D-AlaNH$_2$;

N-(para-Fluorocinnamoyl)-D-1-Nal-Ser-NMeTyr-D-Lys(N-epsilon-nicotinyl)-Leu-Lys (N-epsilon-isopropyl)-Pro-D-AlaNH$_2$;

N-(3-(4-chlorophenyl)propionyl)-D-3-(1-naphthyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(3-fluorophenyl)propionyl)-D-3-(1-naphthyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(2-fluorophenyl)propionyl)-D-3-(1-naphthyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(3,4-difluorophenyl)propionyl)-D-3-(1-naphthyl) alanyl-seryl-N-alpha-methyl-tyrosyl-D-lysyl(N-epsilon-nicotinyl)-leucyl-lysyl (N-epsilon-isopropyl)prolyl-D-alanylamide;

N-(3-(2,4-difluorophenyl)propionyl)-D-3-(1-naphthyl) alanyl-seryl-N-alpha-methyl-tyrosyl-D-lysyl(N-epsilon-nicotinyl)-leucyl-lysyl (N-epsilon-isopropyl)prolyl-D-alanylamide;

N-(3-(2,3-difluorophenyl)propionyl)-D-3-(1-naphthyl) alanyl-seryl-N-alpha-methyl-tyrosyl-D-lysyl(N-epsilon-nicotinyl)-leucyl-lysyl (N-epsilon-isopropyl)prolyl-D-alanylamide;

N-(3-(pentafluorophenyl)propionyl)-D-3-(1-naphthyl) alanyl-seryl-N-alpha-methyl-tyrosyl-D-lysyl(N-epsilon-nicotinyl)-leucyl-lysyl (N-epsilon-isopropyl)prolyl-D-alanylamide;

N-(3-(4-bromophenyl)propionyl)-D-3-(1-naphthyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-trifluoromethylphenyl)propionyl)-D-3-(1-naphthyl) alanyl-seryl-N-alpha-methyl-tyrosyl-D-lysyl(N-epsilon-nicotinyl)-leucyl-lysyl (N-epsilon-isopropyl)prolyl-D-alanylamide;

N-(3-(4-methylphenyl)propionyl)-D-3-(1-naphthyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-nitrophenyl)propionyl)-D-3-(1-naphthyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-cyanophenyl)propionyl)-D-3-(1-naphthyl)alanyl-seryl-N-alpha-methyl-tyrosyl-D-lysyl (N-epsilonnicotinyl)-leucyl-lysyl (N-epsilon-isopropyl)-prolyl-D-alanylamide;

N-(3-(4-methoxyphenyl)propionyl)-D-3-(1-naphthyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-hydroxyphenyl)propionyl)-D-3-(1-naphthyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-aminophenyl)propionyl)-D-3-(1-naphthyl)alanyl-seryl-N-alpha-methyl-tyrosyl-D-lysyl (N-epsilon-nicotinyl)-leucyl-lysyl (N-epsilon-isopropyl)-prolyl-D-alanylamide;

N-(3-(4-(N-acetylamino)phenyl)propionyl)-D-3-(1-naphthyl) alanyl-seryl-N-alpha-methyl-tyrosyl-D-lysyl(N-epsilon-nicotinyl)-leucyl-lysyl (N-epsilon-isopropyl)prolyl-D-alanylamide;

N-(3-(4-Fluorophenyl)propionyl)-D-1-Nal-N-alpha-azaGly-NMeTyr-D-Lys (N-epsilon-nicotinyl)-Leu-Lys(N-epsilon-isopropyl)-Pro-D-AlaNH$_2$;

N-Acetyl-alpha-aza-4-Cl-Phe-D-1-Nal-Ser-NMeTyr-D-Lys(N-epsilon-nicotinyl)-Leu-Lys (N-epsilon-isopropyl)-Pro-DAlaNH$_2$;

N-(3-(4-Fluorophenyl)propionyl)-D-1-Nal-Ser-NMeTyr-D-Lys (N-epsilon-nicotinyl)-Leu-Lys(N-epsilon-isopropyl)-cis-beta-amino-cyclopentanecarbonyl-D-AlaNH$_2$; and N-(3-(4-Fluorophenyl)propionyl)-D-1-Nal-Ser-NMeTyr-D-Lys (N-epsilon-nicotinyl)-Leu-Lys(N-epsilon-isopropyl)-trans-beta-amino-cycloentanecarbonyl-D-AlaNH$_2$.

Effect and Utilities of LHRH Agonists and Antagonists

The LHRH agonist and antagonist compounds of the invention are useful for treatment of precocious puberty, prostate cancer, benign prostatic hypertrophy, endometriosis, uterine fibroids, breast cancer, acne, premenstrual syndrome, polycystic ovary syndrome and diseases which result from excesses or deficiencies in gonadal hormone production in either sex. LHRH agonists and antagonists are also useful for controlling reproduction in females and males. The LHRH agonists, when administered in pulses, are useful as fertility promoters. Compounds of the invention are also useful for suppressing levels of dihydrotestosterone (DHT).

The LHRH agonist compounds of the invention are also useful for growth promotion in female animals and for sspawning promotion in fish.

The compounds of the invention are also useful when administered in combination with a steroidal or nonsteroidal antiandrogenic agent. Examples of suitable antiandrogenic agents include, but are not limited to, 5,5 dimethyl-3 (4 nitro-3-trifluoromethylphenyl) 2,4-imidazolinedione and 2-methyl N (4-nitro 3-trifluoromethylphenyl)-propanamide.

In the practice of the method of this invention an effective amount of a compound of the invention or a pharmaceutical composition containing the same is administered to the subject in need of, or desiring, such treatment. These compounds or compositions may be administered by any of a variety of routes depending upon the specific end use, including orally, parenterally (including subcutaneous, intramuscular and intravenous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of slow release, depot or implant formulations as described more fully herein below.

In general, to modulate levels of sex hormones in male or female mammals for the uses herein above described, it is expedient to administer the active ingredient in amounts between about 0.01 and 10 mg/kg body weight per day, preferably between about 0.1 and 5.0 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being teeated, the type of treatment, the degree of affliction or need and, of course, the judgment of the medical practitioner. In general, parenteral administration reguires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non toxic carrier. As mentioned above, such compositions may be prepared for use for parenteral (subcutaneous, intramuscular or intraveneous) administration, particularly in the form of liquid solutions or suspensions; for use in vaginal or rectal administration, particularly in semisolid forms such as creams and suppositories; for oral or buccal administration, particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in *Remington's Pharmaceutical Sciences,* Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for inhalation administratiom may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non toxic, non-antigenic polymer such as a polylactic acid/polyglycolic acid polymer for example as described in U.S. Pat. No. 3,773,919. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, *Sustained and Controlled Release Drug Delivery Systems,* J. R. Robinson ed., Marcel Dekker, Inc., New York, 1978. Particular reference with respect to LHRH type compounds may be found, for example, in U.S. Pat. No. 4,010,125.

Synthesis of the Peptides

The polypeptides of the present invention may be synthesized by any techniques that are known to those skilled in the art. For solid phase peptide synthesis, a summary of the many techniques may be found in J. M. Stewart and J. D. Young, *Solid Phase Peptide Synthesis,* W. H. Freeman Co., San Francisco, 1963 and J. Meienhofer, *Hormonal Proteins and Peptides,* Vol. 2., p.46, Academic Press (New York), 1973. For classical solution synthesis see G. Schroder and K. Lupke, *The Peptides,* vol. 1, Academic Pres (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis.

In this particularly preferred method the alpha-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, (alpha,alpha)-dimethyl-3,5-dimethoxybenzyloxycarbonyl, o-nitrophenylsulfenyl, 2-cyano-t-butyloxycarbonyl, 9-fluorenylmethyloxycarbonyl and the like. The t-butyloxycarbonyl (Boc) protecting group is preferred.

Particularly preferred side chain protecting groups are, for arginine: nitro, p-toluenesulfonyl, 4-methoxybenzenesulfonyl, Cbz, Boc and adamantyloxycarbonyl; for tyrosine: benzyl, o-bromobenzyloxycarbonyl, 2,6-dichlorobenzyl, isopropyl, cyclohexyl, cyclopentyl and acetyl; for serine: benzyl and tetrahydropyranyl; for tryptophan: formyl.

In the solid phase peptide synthesis method, the C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer, and the like. Chloromethyl-polystyrene-1% divinylbenzene polymer is especially preferred. For the special case where the C-terminus of the compound will be glycinamide, a particularly useful support is the benzhydrylamino-polystyrene-divinylbenzene polymer described by P. Rivaille, et al, *Helv. Chim. Acta.,* 54, 2772 (1971). The coupling to the chloromethyl polystyrene-divinylbenzene type of resin is made by means of the reaction of the alpha-N-protected amino acid, especially the Boc-amino acid, as its cesium, tetramethylammonium, triethylammonium, 1,5-diazabicyclo [5.4.0]undec-5-ene, or similar salt. The coupling reaction is accomplished in a solvent such as ethanol, acetonitrile, N,N-dimethylformamide (DMF), and the like, with the chloromethyl resin at an elevated temperature, for example between about 40° and 60° C., for from about 12 to 48 hours. Preferred reagents and reaction conditions involve the coupling of an alpha N Boc amino acid cesium salt with the resin in DMF at about 50° C. for about 24 hours. The alpha-N Boc amino acid is attached to the benzhydrylamine resin by means of N,N'-dicyclohexylcarbodiimide (DCC) or N,N'-diisopropylcarbodiimide (DIC) with or without 1-hydroxybenzotriazole (HOBT), benzotriazol-1-yloxy-tris(dimethylamino)-phosphoniumhexafluorophosphate (BOP) or bis(2-oxo-3-oxazolidinyl)phosphine chloride (BOPCl), mediated coupling for from about 1 to about 24 hours, preferably about 12 hours at a temperature of between about 10° and 50° C., preferably 25° C. in a solvent such as dichloromethane or DMF, preferably dichloromethane. The coupling of the carboxyl group to the N-methyl-Ser-(OBzl) attached to the peptide resin requires catalysis by 4-dimethylaminopyridine (DMAP), in addition to the carbodiimide reagent.

The coupling of successive protected amino acids can be carried out in an automatic polypeptide synthesizer as is well known in the art. The removal of the alpha-N-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in 0.4M concentration in approximately 3.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-isopropylcarbodiimide (DIC) or other carbodiimide either alone or in the presence of HOBT, N-hydroxysuccinimide, other N-hydroxyimides or oximes. Alternately, protected amino acid active ester (e.g. p-nitrophenyl, pentafluorophenyl and the like) or symmetrical anhydrides may be used.

At the end of the solid phase synthesis the fully protected polypeptide is removed from the resin. When the linkage to the resin support is of the benzyl ester type, cleavage is by means of aminolysis with an alkylamine or fluoroalkylamine for peptides with a proline C-terminus, or by aminolysis with, for example, ammonia/methanol or ammonia/ethanol for peptides with a glycine C-terminus at a temperature between about 10° and 50° C., preferably about 25° C., for between about 12 and 24 hours preferably about 18 hours. Alternatively, the peptide may be removed from the resin by transesterification, e.g., with methanol, followed by aminolysis or by direct transamidation. The protected peptide may be purified at this point by silica gel chromatography or taken to the next step directly. The removal of the side chain protecting groups from the polypeptide is performed by treating the aminolysis product with, for example, anhydrous liquid hydrogen fluoride in the presence of anisole and dimethylphosphite or other carbonium scavenger. The hydrogen fluoride treatment is carried out at a temperature between about −10° and +10° C., preferably about 0° C., for between about 15 minutes and 1 hour. The fully deprotected polypeptide is then purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g., on Sephadex G-25, LH-20, or countercurrent distribution; high performance liquid chromatography (HPLC), especially reverse phase HPLC on octyl- or octadecylsilyl-silica bonded phase column packing.

If a racemic amino acid is used in the 1,2,3,6 or 10 position, the diastereomeric nonapeptide or decapeptide final products are separated, and the desired peptide containing a D-amino acid in the appropriate position is isolated and purified, preferably during the above-described chromatographic process.

The preparation of peptides having C-terminal azaglycine amides is preferably done using classical peptide solution synthesis using known peptide intermediates. This is described in more detail in Example 5.

The following examples will serve to further illustrate the preparation of the novel compounds of the invention.

EXAMPLE 1

N-(1-Naphthylacetyl)-Ser-Tyr-D-Leu-Leu Arg-ProNHEt(1) and N-(1-naphthylacetyl)-Ser(OBzl)-Tyr-D-Leu-Leu-Arg-ProNHEt(2)

In the reaction vessel of a Biosearch 9500 Peptide Synthesizer was placed 1.5 g (1.05 mmol) of BOC Pro-O-Resin (Merrifield resin). Amino acids and 1-naphthylacetic acid were added sequentially to the resin according to the following synthetic cycle:

1. Deblocking, to remove the t-Boc group from the alpha-amino function of the peptide, was carried out using a solution of 45% trifluoroacetic acid (TFA), 2.5% anisole, 2.0% dimethyl phosphite, and 50.5% methylene chloride. The resin was prewashed with the deblocking solution previously described for one minute and then the deblocking reaction was run for 20 minutes.

2. Base wash, to remove and neutralize the TFA used for deprotection, was carried out using a solution of 10% N,N'-diisopropylethylamine in methylene chloride. The resin was washed with base three times for one minute each time after each deblocking step.

3. Coupling reaction was carried out with a 3.5-fold molar excess of 0.4M DMF solution of a t-Boc protected amino acid derivative, which was introduced simultaneously with 3.5-fold molar excess of 0.4M methylene chloride solution of diisopropylcarbodiimide as activator. The activated amino acid was then coupled to the free alpha amino group of the peptide-resin. The reaction time was as described in the following protocol.

4. Wash, each reaction step was followed by three washes of one minute each: one of methylene chloride, one of (1:1) methylene-chloride-DMF, and one of DMF.

Protocol

The amino acids were coupled to the resin in the following order using the conditions indicated:

| Amino Acid | Wash | Coupling | Deprotection |
| --- | --- | --- | --- |
| Boc-Arg(Tos) | basewash | two-1 hr | deblock |
| Boc-Leu | basewash | two-1 hr | deblock |
| Boc-D-Leu | basewash | two-1 hr | deblock |
| Boc-Tyr-(2-Br-Cbz) | basewash | two-1 hr | deblock |
| Boc-Ser(OBzl) | basewash | two-1 hr | deblock |
| Naphthyl-acetic Acid | basewash | two-1 hr | deblock |

Upon the completion of the synthesis the resin was removed from the reaction vessel and dried in vacuo to give the protected polypeptide resin. The protected peptide was removed from the resin upon treatment with anhydrous ethylamine with or without 10% DMF or methanol, for 48 hours at room temperature. The resin beads were filtered and washed with methanol. The filtrate was concentrated in vacuo and the residue was triturated with water togive, after filtration and drying, the protected peptide as a white powder. The protecting groups were finally removed upon treatment at 0° C. for 1 hour with 5 to 10 ml anhydrous liquid HF in the presence of 1 ml of anisole and 0.5 ml of dimethyl phosphite. The HF was evaporated and the residue was dissolved in methanol and then concentrated in vacuo. The residue was washed twice with ether and then dissolved in a solution of (1:1:0.1) water:acetonitrile:acetic acid, filtered, and lyophilized to give 0.6 g of the crude product. The crude peptide was purified by high performance liguid chromatography on a 25 cm×2.5 cm Dynamax C-18 column (25-40 micron) using solvent mixture gradients ranging from 89% H2O/11% CH3CN/0.1% TFA to 49% H2O/51% CH3CN/0.1% TFA over a period of 50 min and afterwards changing to 100% CH3CN/0.1% TFA over a period of 10 min.

The flow rate was 15 ml/min and UV detection was at 260 nM.

N-(1-Naphthylacetyl)Ser-Tyr-D-Leu-Leu-Arg-Pro-NHEt(1) as the trifluoroacetate salt was eluted with $R_T=9$ minutes as a single peak, was collected and lyophilized. Fab (fast atom bombardment) Mass spec. m/e 943 $(M+H)^+$. Amino Acid Anal 1.1 Pro; 0.8 Arg; 1.9 Leu; 1.0 Tyr; 0.8 Ser.

N-(1-Naphthylacetyl)Ser(OBzl)-Tyr-D-Leu-Leu-Arg-Pro-NHEt(2) as the trifluoroacetate salt was obtained from the same HPLC separation as a single peak which was eluted with $R_T=26.28$ minutes, collected and lyophilized. Fab Mass spec. m/e 1032 $(M^++H)$. Amino Acid Anal.: 1.0 Pro; 0.8 Arg; 2.0 Leu; 1.0 Tyr; 0.9 Ser.

EXAMPLE 2

Using a synthesis program identical to that described in Example 1 and substituting the appropriate acids and amino acids using the procedure previously described, the following compounds were prepared, purified by HPLC, and characterized as their trifluoroacetate salts:

(4-9)[N-(3-(1-Naphthyl)propionyl)-$Ser^4$-D-$Leu^6$-$Pro^9$-NHEt] LHRH(3), $R_T=22.5$ min., Fab Mass spec m/e 957$(M+H)^+$; AA Anal.: 1.1 Pro; 0.8 Arg; 2.1 Leu; 1.0 Tyr; 0.9 Ser.

(4-9)[N-(3-(1-Naphthyl)propionyl)-$Ser^4$(OBzl)-D-$Leu^6$-$Pro^9$-NHEt]LHRH(4), $R_T=27.4$ minutes, Fab Mass spec m/e 1047$(M+H)^+$; AA Anal.: 1.0 Pro; 0.9 Arg; 2.0 Leu; 1.0 Tyr; 0.8 Ser.

(4-9)[N-(3-(1-Naphthyl)acryloyl)-$Ser^4$-D-$Leu^6$-$Pro^9$-NHEt]LHRH(5), $R_T=31.9$ minutes, Fab Mass spec m/e 955$(M+H)^+$; AA Anal.: 1.1 Pro; 0.8 Arg; 2.1 Leu; 1.0 Tyr; 0.8 Ser.

(4-9)[N-(1-Naphthoyl)-$Ser^4$-D-$Leu^6$-$Pro^9$-NHEt] LHRH(6), $R_T=18.9$ minutes, Fab Mass spec m/e 929$(M+H)^+$; AA Anal.: 1.1 Pro; 0.8 Arg; 2.1 Leu; 1.0 Tyr; 0.9 Ser.

(4-9)[N-(3-Diphenylpropionyl)-$Ser^4$-D-$Leu^6$-$Pro^9$-NHEt]LHRH(7), $R_T=21.4$ minutes, Fab Mass spec m/e 969$(M+H)^+$; AA Anal.: 0.9 Pro; 0.9 Arg; 2.0 Leu; 0.9 Tyr; 0.8 Ser.

(4-9)[N-(3-(1-Naphthyl)acetyl)-$Ser^4$-D-$Trp^6$-$Pro^9$-NHEt] LHRH(8), $R_T=17.2$ minutes, Fab Mass spec m/e 1016$(M+H)^+$; AA Anal.: 1.1 Pro; 0.9 Arg; 1.0 Leu; 1.0 Trp; 1.0 Tyr; 0.9 Ser.

(4-9)[N-(3-(1-Naphthyl)propionyl)-$Ser^4$-D-$Trp^6$-$Pro^9$-NHEt]LHRH(9), $R_T=36.3$ minutes, Fab Mass spec m/e 1030$(M+H)^+$; AA Anal.: 1.1 Pro; 0.8 Arg; 1.1 Leu; 0.9 Trp; 1.1 Tyr; 0.9 Ser.

(4-9)[N-(3-(1-Naphthylpropionyl)-$Ser^4$(OBzl)-D-$Trp^6$-$Pro^9$-NHEt]LHRH(10), $R_T=40.2$ minutes, Fab Mass spec m/e 1120$(M+H)^+$; AA Anal.: 1.1 Pro; 0.9 Arg; 1.0 Leu; 0.9 Trp; 1.0 Tyr; 0.8 Ser.

(4-9)[N-(2-Naphthylacetyl)-$Ser^4$-D-$Trp^6$-$Pro^9$-NHEt] LHRH(11), $R_T=26.18$ minutes, Fab Mass spec m/e 1016$(M+H)^+$; AA Anal.: 1.0 Pro; 1.0 Arg; 1.0 Leu; 0.9 Trp; 1.0 Tyr; 0.8 Ser.

(4-9)[N-(2-Naphthylacetyl)-$Ser^4$(OBzl)-D-$Trp^6$-$Pro^9$-NHEt]LHRH(12), $R_T=31.48$ minutes, Fab Mass spec m/e 1106$(M+H)^+$; AA Anal.: 1.1 Pro; 1.0 Arg; 1.0 Leu; 0.9 Trp; 1.0 Tyr; 0.8 Ser.

(4-9)[N-(1-Naphthoxyacetyl)-$Ser^4$-D-$Trp^6$-$Pro^9$-NHEt]LHRH(13), $R_T=20.6$ minutes, Fab Mass spec m/e 1032$(M+H)^+$; AA Anal.: 1.0 Pro; 1.0 Arg; 1.0 Leu; 1.0 Trp; 1.0 Tyr; 0.8 Ser.

(4-9)[N-(3-Diphenylpropionyl)-$Ser^4$-D-$Trp^6$-$Pro^9$-NHEt]LHRH(14), $R_T=24.95$ minutes, Fab Mass spec m/e 1056$(M+H)$; AA Anal.: 1.0 Pro; 1.0 Arg; 1.0 Leu; 0.8 Trp; 1.0 Tyr; 0.8 Ser.

(4-9)[N-(cinnamoyl)-$Ser^4$-D-$Trp^6$-$Pro^9$-NHEt] LHRH(15), $R_T=15.0$ minutes, Fab Mass spec m/e 978$(M+H)^+$; AA Anal.: 1.0 Pro; 0.9 Arg; 1.0 Leu; 0.8 Trp; 1.0 Tyr; 0.8 Ser.

(4-9)[N-(ortho-Methoxycinnamoyl)-$Ser^4$-D-$Trp^6$-$Pro^9$-NHEt]LHRH(16), $R_T=16.75$ minutes, Fab Mass spec m/e 1008$(M+H)^+$; AA Anal.: 1.0 Pro; 1.0 Arg; 1.0 Leu; 0.8 Trp; 0.9 Tyr; 0.8 Ser.

(4-9)[N-(Phenylacetyl)-$Ser^4$-D-$Trp^6$-$Pro^9$-NHEt] LHRH(17), $R_T=25.00$ minutes, Fab Mass spec m/e 966$(M+H)^+$; AA Anal.: 1.0 Pro; 1.0 Arg; 1.1 Leu; 0.8 Trp; 0.9 Tyr; 0.8 Ser.

(4-9)[N-(1-Naphthylacetyl)-$Ser^4$-D-2-$Nal^6$-$Pro^9$-NHEt]LHRH(18), $R_T=25.8$ minute, Fab Mass spec m/e 1027$(M+H)^+$; AA Anal.: 1.1 Pro; 0.9 Arg; 1.0 Leu; 1.0 Tyr; 0.9 Ser.

(4-9)[N-(1-Naphthylacetyl)-$Ser^4$(OBzl)-D-2-$Nal^6$-$Pro^9$-NHEt]LHRH(19), $R_T=30.61$ minutes, Fab Mass spec m/e 1117$(M+H)^+$; AA Anal.: 1.0 Pro; 0.9 Arg; 1.0 Leu; 0.9 Tyr; 0.8 Ser.

(4-9)[N-3-(1-Naphthyl)propionyl)-$Ser^4$-D-2-$Nal^6$-$Pro^9$-NHEt]LHRH(20), $R_T=24.2$ minutes, Fab Mass spec m/e 1041$(M+H)^+$; AA Anal.: 1.1 Pro; 0.9 Arg; 1.0 Leu; 1.0 Tyr; 0.8 Ser.

(4-9)[N-(3-Indolecarbonyl)-$Ser^4$-D-$Leu^6$-Pro9-NHEt] LHRH(21), $R_T=15.5$ minutes, Fab Mass spec m/e 918$(M+H)^+$; AA Anal.: 1.0 Pro; 0.9 Arg; 2.0 Leu; 0.9 Tyr; 0.8 Ser.

(4-9)[N-(3-(3-Indole)acetyl)-$Ser^4$-D-$Leu^6$-$Pro^9$-NHEt] LHRH(22), $R_T=13.67$ minutes, Fab Mass spec m/e 932$(M+H)^+$; AA Anal.: 1.0 Pro; 1.0 Arg; 2.0 Leu; 1.0 Tyr; 0.8 Ser.

(4-9)[N-(3-(3-Indole)propionyl)-$Ser^4$-D-$Leu^6$-$Pro^9$-NHEt] LHRH(23), $R=17.6$ minutes, Fab Mass spec m/e 946$(M+H)^+$; AA Anal.: 1.1 Pro; 1.0 Arg; 2.0 Leu; 1.1 Tyr; 0.8 Ser.

(4-9)[N-(3-(3-Indole)propionyl)-$Ser^4$-D-$Trp^6$-$Pro^9$-NHEt] LHRH(24), $R_T=24.8$ minutes, Fab Mass spec m/e 1019$(M+H)^+$; AA Anal.: 1.1 Pro; 0.9 Arg; 2.0 Leu; 1.0 Tyr; 0 8 Ser.

(4-9)[N-(4-(3-Indole)butyryl)-$Ser^4$-D-$Leu^6$-Pro9-NHEt] LHRH(25), $R_T=19.3$ minutes, Fab Mass spec m/e 960$(M+H)^+$; AA Anal.: 1.0 Pro; 1.0 Arg; 2.0 Leu; 1.0 Tyr; 0.8 Ser.

(4-9)[N-(3-(3-Indole)propionyl)-$Ser^4$-D-2-$Nal^6$-$Pro^9$-NHEt]LHRH(26), $R_T=24.4$ minutes, Fab Mass spec m/e 1030$(M+H)^+$; AA Anal.: 1.1 Pro; 1.0 Arg; 1.0 Leu; 1.0 Tyr; 0.8 Ser.

(4-9)[N-(4-(3-Indole)butyryl)-$Ser^4$-D-2-$Nal^6$-$Pro^9$-NHEt]LHRH(27), $R_T=22.4$ minutes, Fab Mass spec m/e 1044$(M+H)^+$; AA Anal.: 1.0 Pro; 1.0 Arg; 1.0 Leu; 1.0 Tyr; 0.8 Ser.

(4-9)[N-(Adamantylacetyl)-$Ser^4$-D-$Trp^6$-$Pro^9$-NHEt] LHRH(28), $R_T=23.6$ minutes, Fab Mass spec m/e 1024$(M+H)^+$; AA Anal.: 1.0 Pro; 1.0 Arg; 1.0 Leu; 0.9 Trp, 1.0 Tyr; 0.8 Ser.

(4-9)[N-(1-Naphthylacetyl)-$Ser^4$-D-$Phe^6$-$Pro^9$-NHEt] LHRH(29), $R_T=20.27$ minutes, Fab Mass spec m/e 977$(M+H)^+$; AA Anal.: 1.0 Pro; 1.0 Arg; 1.1 Leu; 1.0 Tyr; 0.8 Ser.

(4-9)[N-(1-Naphthylacetyl)-$Ser^4$(OBzl)-D-$Phe^6$-$Pro^9$-NHEt]LHRH(30), $R_T=24.69$ minutes, Fab Mass spec m/e 1067$(M+H)^+$; AA Anal.: 1.1 Pro; 1.0 Arg; 1.0 Leu; 1.0 Phe; 1.0 Tyr; 0.8 Ser.

(4-9)[N-(3-(3-Indole)propionyl)-$Ser^4$-D-$Phe^6$-$Pro^9$-NHEt]LHRH(31), $R_T=30.28$ minutes, Fab Mass spec m/e 980(M+H)+; AA Anal.: 1.1 Pro; 1.0 Arg; 1.0 Leu; 1.0 Phe; 1.0 Tyr; 0.9 Ser.

(4-9)[N-(1-Naphthylacetyl)-Ser$^4$-D-Cha$^6$-Pro$^9$-NHEt] LHRH(32), $R_T$=24.09 minutes, Fab Mass spec m/e 983(M+H)+; AA Anal.: 1.0 Pro; 1.0 Arg; 1.0 Leu; 1.0 Tyr; 0.9 Ser.

(4-9)[N-(1-Naphthylacetyl)-Ser$^4$(OBzl)-D-Cha$^6$-Pro$^9$-NHEt]LHRH(33), $R_T$=28.41 minutes, Fab Mass spec m/e 1073(M+H)+; AA Anal.: 1.0 Pro; 0.9 Arg; 1.0 Leu; 1.0 Tyr; 0.9 Ser.

(4-9)[N-(3-(1-Indole)propionyl)-Ser$^4$-D-Cha$^6$-Pro$^9$-NHEt]LHRH(34), $R_T$=22.4 minutes, Fab Mass spec m/e 986(M+H)+; AA Anal.: 1.1-Pro; 1.0 Arg; 1.0 Leu; 1.0 Tyr; 0.8 Ser.

(4-9)[N-(3-(3-Indole)propionyl)-Ser$^4$-D-Arg$^6$-Pro$^9$-NHEt]LHRH(35), $R_T$=25.39 minutes, Fab Mass spec m/e 989(M+H)+; AA Anal.: 1.1 Pro; 2.0 Arg; 1.0 Leu; 0.9 Tyr; 0.8 Ser.

(4-9)[N-(4-(3-Indole)butyryl)-Ser$^4$-D-Cha$^6$-Pro$^9$-NHEt]LHRH(36) $R_T$=30.43 minutes, Fab Mass spec m/e 1000(M+H)+; AA Anal.: 1.0 Pro; 1.0 Arg; 1.0 Leu; 0.9 Tyr; 0.8 Ser.

(4-9)[N-(1-Naphthylacetyl)-Ser$^4$-D-Arg$^6$-Pro$^9$-NHEt] LHRH(37), $R_T$=30.83 minutes, Fab Mass spec m/e 986(M+H)+; AA Anal.: 1.0 Pro; 2.0 Arg; 1.0 Leu; 1.0 Tyr; 0.8 Ser.

(4-9)[N-(1-Naphthylacetyl)-Ser$^4$(OBzl)-D-Arg$^6$-Pro$^9$-NHEt]LHRH(38), $R_T$ 40.84 minutes, Fab Mass spec m/e 1076(M+H)+; AA Anal.: 1.0 Pro; 2.1 Arg; 1.0 Leu; 1.0 Tyr; 0.9 Ser.

(4-9)[N-(1-Naphthoyl)-Ser$^4$-D Arg$^6$-Pro$^9$-NHEt] LHRH(39), $R_T$=27.81 minutes, Fab Mass spec m/e 972(M+H) ; AA Anal.: 1.0 Pro; 2.1 Arg; 1.0 Leu; 1.0 Tyr; 0.9 Ser.

(4-9)[N-(3-Pyridylacetyl)-Ser4-D-Leu$^6$-Pro$^9$-NHEt] LHRH(40), $R_T$=20.83 minutes, Fab Mass spec m/e 894(M+H)+; AA Anal.: 1.0 Pro; 1.0 Arg; 2.0 Leu; 1.0 Tyr; 0.8 Ser.

(4-9)[N-(3-(3-Pyridyl)propionyl)-Ser$^4$-D-Leu$^6$-Pro$^9$-NHEt]LHRH(41), $R_T$=15.24 Fab Mass spec m/e 908(M+H)+; AA Anal.: 1.0 Pro; 1.0 Arg; 2.1 Leu; 0.9 Tyr; 0.8 Ser.

(4-9)[N-(3-(3-Pyridyl)acryloyl)-Ser$^4$-D-Leu$^6$-Pro$^9$-NHEt]LHRH(42), $R_T$=15.66 minutes, Fab Mass spec m/e 906(M+H)+; AA Anal.: 1.0 Pro; 1.0 Arg; 2.1 Leu; 1.0 Tyr; 0.8 Ser.

(4-9)[N-(3-(3-Pyridyl)acryloyl)-Ser$^4$-D-Trp$^6$-Pro$^9$-NHEt]LHRH(43), $R_T$=15.5 minutes, Fab Mass spec m/e 979(M+H)+; AA Anal.: 1.0 Pro; 1.0 Arg; 1.0 Leu; 0.9 Tyr; 0.8 Ser.

(4-9)[N-(3-(1-Naphthyl)propionyl)-Ser$^4$-D-Arg$^6$-Pro$^9$-NHEt]LHRH(44), $R_T$=30.33 minutes, Fab Mass spec m/e 1001(M+H)+; AA Anal : 1.1 Pro, 1.9 Arg, 1.1 Leu, 1.0 Tyr, 0.8 Ser.

(4-9)[N-(3-(1-Naphthyl)propionyl)-Ser$^4$(OBzl)-D-Arg$^6$-Pro$^9$-NHEt]LHRH(45), $R_T$=37.95 minutes, Fab Mass spec m/e 1091 (M+H) ; AA Anal.: 1.0 Pro, 2.0 Arg, 1.0 Leu, 1.0 Tyr, 0.8 Ser.

EXAMPLE 3

N-(3-(3-Indole)propionyl)Ser-Tyr-D-Trp-N-Me-Leu-Arg-Pro-NHEt(46)

Using the general procedure described in Example 1 and substituting with the appropriate acids and amino acids, except that 0.1% of 4-dimethylaminopyridine was added to the N-Boc-N-indole-formyl-D-tryptophan DMF solution before coupling, provided (4-9)[N-(3-indolepropionyl)Ser$^4$-D-Trp$^6$-N-Me-Leu$^7$-Pro-NHEt]LHRH as the trifluoroacetate salt. $R_T$=22.45 minutes. Fab Mass spec. m/e 1033-(M+H)+. Amino Acid Anal: 1.1 Pro, 1.1 Arg, 0.9 Trp, 0.9 Tyr, 0.8 Ser.

EXAMPLE 4

N-(3-(3-Indole)propionyl)-Ser-Tyr-D-2-Nal-Leu-Arg-Pro-Gly-NH$_2$(47)

Using the general procedure of Example 1, but starting with 1.0 g (0.7 mmol) Boc-Gly-O-Resin (Merrifield Resin), followed by removal of the Boc group, coupling with N-Boc-Pro, and then coupling with the appropriate acids, the desired protected peptide-resin was obtained. The peptide was cleaved from the resin upon treatment with anhydrous liquid ammonia (20 ml) and methanol (5 ml) containing 10% dimethylethanolamine at room temperature for 48 h. The solvent and excess of reagents were removed in vacuo. The residue was triturated with water to give the protected peptide as a white powder. The peptide was filtered and dried over P$_2$O$_5$ overnight. The protected peptide was treated at 0° C. for 1 hr with anhydrous HF (8 ml) containing 10% of anisole and 5% of dimethylphosphite. The excess of reagents was removed in vacuo and the residue was triturated with ether. The residue was filtered and dissolved in (1:1) acetonitrile: water (30 ml) containing 5% acetic acid. The solution was filtered and lyophilized to give the desired crude product as a white powder. This was purified by HPLC using a 25 cm×2.5 cm Dynamax C-18 column (25–40 microns) and using a solvent mixture in a gradient changing from 89% H$_2$O: 11% CH$_3$CN: 0.1% TFA to 49% H$_2$O: 51% CH$_3$CN: 0.1% TFA over a period of 20 minutes and afterwards changing to 100% CH$_3$CN/0.1% TFA over a period of 10 minutes. The flow rate was 15 ml/minutes and UV detection was at 260 nM. N-(3-(3-Indole)propionyl)-Ser-Tyr-D-(2)Nal-Leu-Arg-Pro-Gly-NH$_2$ trifluoroacetate eluted at $R_T$=21.44 minutes as a single peak, was collected and lyophilized. Fab Mass spec. m/e 1059 (M+H). Amino Acid Anal: 1.0 Gly, 1.0 Pro, 0.9 Arg, 1.0 Leu, 1.0 Tyr, 0.8 Ser.

EXAMPLE 5

N-(1-Naphthylacetyl)-Ser-Tyr-D-Leu-Leu-Arg-Pro-Azagly-NH$_2$(48)

This peptide can be prepared according to the following scheme:

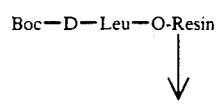 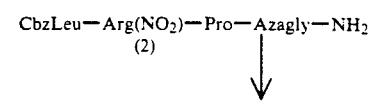

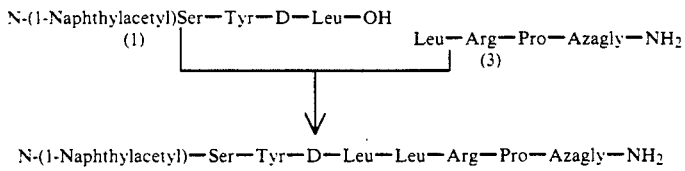

N-(1-Naphthylacetyl)—Ser—Tyr—D—Leu—Leu—Arg—Pro—Azagly—NH₂

Fragment (1) is synthesized using the solid phase technique starting with Boc-D-Leu-0 Resin, then sequentially coupling with Boc-Tyr(2 Br-Cbz), Boc-Ser-(OBzl), and 1-naphthylacetic acid. The peptide is cleaved from the resin with HF to give the desired peptide (1). Peptide (3) is prepared using the procedure described by A. S. Dutta *J. Med. Chem.*, 21, 1018 (1978). Peptide (3) is coupled with (1) using DCC/HOBt. The desired product is purified by HPLC and characterized.

EXAMPLE 6

Using the general prodecure of Example 1, but substituting with the appropriate amino acids and acids, the following peptides can be prepared:

N-(3-(p-Methoxyphenyl)propionyl)-seryl-tyrosyl D-tryptyl-leucyl-arginyl-prolylethylamide.

N-(p-Methoxybenzoyl)-seryl-tryosyl-D-tryptyl-arginyl-prolylethylamide.

N-(2-phenoxyacetyl)-seryl-tyrosyl-D-arginyl-leucyl-arginyl-prolylethylamide.

N-(3-(3-Quinolyl)propionyl)-seryl-tyrosyl-D-leucyl-leucyl-arginyl-prolylethylamide.

N-(2-(2,8-Dehydroisoquinoloyl)-seryl-tyrosyl-D-tryptyl-leucyl-arginyl-prolylethylamide.

N-(2-(2,8-Dehydro)isoquinolyl)-seryl-tyrosyl-D-arginyl-leucyl-arginyl-prolylethylamide.

N-(Butyryl)-seryl-tyrosyl-D-tryptyl-leucyl-arginyl-prolylethylamide.

N-(Adamantylacetyl)-seryl-tyrosyl-D-leucyl-leucyl-arginyl-prolylethylamide.

N-(Adamantylacetyl)-seryl-tyrosyl-D-arginyl-leucyl-arginyl-prolylethylamide.

N-(Adamantylacetyl)-seryl-tyrosyl-O-t-butyl-D-seryl-leucyl-arginyl-prolylethylamide.

N-(3-(3-Indole)propionyl)-seryl-tyrosyl-O-t-butyl-D-seryl-leucyl-arginyl-prolylethylamide.

N-(1-Naphthylacetyl)-seryl-tyrosyl-O-t-butyl-D-seryl-leucyl-arginyl-prolylethylamide.

EXAMPLE 7

Using the general procedure of Example 4, but substituting with the appropriate amino acids and acids, the following peptides can be prepared:

N-(1-Naphthylacetyl)-seryl-tyrosyl-D-(2)-naphthylalanyl-leucyl-arginyl-prolyl-glycylamide.

N-(3-(1-Naphthyl)propionyl)-seryl-tyrosyl D-(2)-naphthylalanyl-leucyl-arginyl-prolyl-glycylamide.

N-(Adamantylacetyl)-seryl-tyrosyl-D-(2)-naphthylalanyl-leucyl-arginyl-prolyl-glycylamide.

N-(1-Naphthoxyacetyl)-seryl-tyrosyl-D-(2)-naphthylalanyl-leucyl-arginyl-prolyl-glycylamide.

N-(2-Naphthylacetyl)-seryl-tyrosyl-D-(2)-naphthylalanyl-leucyl-arginyl-prolyl-glycylamide.

N-(phenylacetyl)-seryl-tyrosyl-D-(2)-naphthylalanyl-leucyl-arginyl-prolyl-glycylamide.

EXAMPLE 8

N(1-Naphthylacetyl))-Ser-Tyr D-Lys-(N-isp)-Leu-Arg-Pro-NHEt

Using the general procedure of Example 1 the peptide-resin N-(1-Naphthylacetyl) Ser(OBzl)Tyr(O-2-Br-Cbz)-D-N-(epsilon)-FMOC-Lys-Leu-Arg(Tos)-Pro-O-Resin can be prepared. The resin is treated with 20% piperidine in methylene chloride overnight at room temperature to remove the FMOC group. The peptide-resin is filtered, washed three times with (1:1) DMF-methylene chloride, three times with methylene chloride, and dried under vacuum for two hours. Then the peptide resin is treated with 2 equivalents of sodium cyanoborohydride in (1:1) DMF methylene chloride containing 10% acetone. The mixture is stirred at room temperature overnight. The peptide-resin is filtered, washed three times with (1:1) DMF-methylene chloride, and dried in vacuo. The peptide is cleaved from the resin with anhydrous ethylamine, then treated with anhydrous HF/anisole/trimethylphosphite (to remove the protecting groups) as described previously. The crude product is purified with HPLC to give N-(1-naphthylacetyl)-Ser-Tyr-D-Lys-(N-isp)-Leu-Arg-Pro-NHEt.

EXAMPLE 9

(2)-N-(1-Naphthylacetyl)-(3)-N-Et-Dap-Tyr-D-Trp-Leu-Arg-Pro-NHEt

Using the general procedure of Example 8, the peptide-resin N-(1-Naphthylacetyl)-3-FMOC-Dap-Tyr(2-Br-Cbz)-D-Trp(N-formyl)-Leu-Arg(Tos)-Pro-O-Resin is prepared. The resin is first treated with piperidine to remove the FMOC group, then treated with acetaldehyde and sodium cyanoborohydride as described above. The peptide is cleaved from the resin with anhydrous ethylamine and then treated with anhydrous HF/anisole/dimethylphosphite to remove the protecting groups and purified by HPLC to give (2)-N-(1-Naphthylacetyl)-(3)-N-Et-Dap-Tyr-D-Trp-Leu-Arg-Pro-NHEt.

EXAMPLE 10

N-(1-Naphthylacetyl)-N-Me-Ser-Tyr-D-Trp-Leu-Arg-Pro-NHEt

Using the general procedure described in Example 1 and using the appropriate acids and amino acids, but adding 0.1% of 4-dimethylaminopyridine to the DMF solution of 1-naphthylacetic acid before coupling with the N-Me-Ser(OBzl) terminal residue, the desired product is prepared.

EXAMPLE 11

N-(3-(1-Naphthyl)propionyl)-Ser-Tyr-6,7-[2-(S-3-amino
2-oxo-pyrrolidin-1-yl)-S-2-isopropylmethylacetyl]-Arg-Pro-NHEt The desired product is prepared according to the following synthetic steps:

(a) H-Arg(Tos)-Pro-NHEt

The protected dipeptide H-Arg(Tos)-Pro-NHEt is prepared by solid phase using Boc-Pro-O-Resin (Merrifield resin), deblocking and coupling with Boc-Arg(Tos) using the same procedure described in Example 1, and finally deblocking the peptide resin using the previously described deblocking solution. The obtained Arg(Tos) Pro-O-Resin is then treated with ethylamine at room temperature for 48 hours. Work up, trituration of the product with water and drying over $P_2O_5$ gives the desired product.

(b) BOC-[2-(S-3-Amino-2-oxo-pyrrolidin-1-yl)-S-2-isopropylmethylacetic Acid

The desired product is prepared using the procedure described by V. F. Veber and R. M. Freidinger in U.S. Pat. No. 4,493,934.

(c) BOC-[2-(S-3-Amino-2-Oxo-Pyrrolidin-1-yl)-S-2-isopropyl methylacetic Arginyl(Tosyl)-Prolylethylamide 10 mmole of BOC-[2-(S-3-amino-2-oxo-pyrrolidin-1-yl)-S-2-isopropylmethylacetic acid is dissolved in 70 ml of degassed DMF and cooled to 0° under nitrogen. 19 mmole of H-Arg(Tos)-ProNHEt, which was previously described, is dissolved in 30 ml of degassed DMF, and cooled. To the acid solution, 11 mmole of diphenylphosphonylazide(DPPA) and 11 mmole of triethylamine are added, followed by the pre-cooled peptide solution. The reaction mixture is stirred at 0° C. for 3 hours, then at room temperature overnight. The product is worked up, purified using silica gel column chromatography, and eluted with 70:30:3 chloroform/methanol/aqueous ammonia.

(d) [2-(S-3-Amino-2-Oxo-Pyrrolidin-1-yl)-S-2-Isopropylmethyl acetyl-Arginyl(Tosyl)-Prolylethylamide BOC-[2-(S-3 -amino-2-oxo-pyrrolidin-1-yl)-S-2-isopropylmethylacetyl-arginyl(tosyl)-propylethylamide, obtained from the previous reaction, is dissolved at 0° C. in trifluoroacetic acid (60ml) containing 1.5% anisole and 1% dimethylphosphite. The solution is then stirred at room temperature for 30 minutes, and afterwards concentrated in vacuo. The residue is washed twice with ether and dried over $P_2O_5$ to give [2-(S-3-amino-2-oxo-pyrrolidin-1-yl)-S-2-isopropylmethylacetyl-arginyl(tosyl)-prolylethyl amide.

(e) N-(3-(1-Naphthyl)propionyl)-Ser(OBzl)-Tyr(O-2-Br-Cbz)-NHNH₂

N-(1-Naphthyl)propionyl)-Ser(OBzl)-Tyr(O-2-Br-Cbz)-O-Resin is synthesized using the solid phase method described in Example 1, but starting with BOC-Tyr(O -2-Br-Cbz)-O-Resin (Merrifield resin), deblocking and coupling in a sequential order with BOC-Ser-(OBzl) and 1-Naphthylpropionic acid. The peptide resin obtained from the synthesis is treated with anhydrous hydrazine in 10% methanol solution at room temperature for 48 hours. The resin is filtered and the filtrate is concentrated in vacuo. The residue is triturated with ether and dried over $P_2O_5$ to give N-(3-(1-Naphthyl)propionyl)-Ser(OBzl)-Tyr(2-Br-Cbz)-NHNH₂.

(f) N-(3-(1-Naphthyl)propionyl)-Ser(OBzl)-Tyr(O-2-Br-Cbz)-6,7[2-(S-3-amino-2-oxo-pyrrolidin-1-yl)-S-2-isopropylmethylacetyl]Arg(Tos)Pro-NHEt 2.6 mmole of the hydrazide N-(1-Naphthylpropionyl)-Ser(OBzl)-Tyr(O-2-Br-Cbz)-NHNH₂ is dissolved in 26 ml of degassed DMF and cooled to −10° under nitrogen. To the solution is added 2.4 ml of 5.8M hydrochloric acid/THF. The reaction mixture is cooled to −25° C. and to it is added a (1:19) solution of isoamylnitrite/DMF until a positive starch/KI test reaction is obtained. About 16 ml of solution is required. When TLC shows that no hydrazide remained, the reaction is cooled to −40° C. and to it is added a cold DMF solution (4 ml) of [2-(S-3-amino-2-oxo pyrrolidin-1-yl)-S-2-isopropylmethylacetyl-arginyl(tosyl)-prolylethylamide, previously obtained. The pH is raised to 8 with triethylamine. The reaction is stirred at −20° C. for 24 hrs, after which the pH is readjusted to pH 8. Additional peptide is added and the reaction is stirred for an additional 24 hrs at the same temperature. The reaction mixture is concentrated in vacuo. The residue is triturated with water. The solid is filtered and dried over $P_2O_5$ to give N-(1-naphthylpropionyl)-Ser (OBzl)-Tyr-(O-2-Br-Cbr)-6,7[2-(S-3-amino-2-oxo pyrrolidin-1-yl)-S-2-isopropylmethylacetyl]-Arg(Tos)-Pro-NHEt.

(g) N-(1-Naphthylpropionyl)-Ser-Tyr-6,7[2-(S-3-amino-2-oxo-pyrrolidin-1-yl)-S-2-isopropylmethylacetyl]-Arg-Pro-NHEt N-(1-naphthylpropionyl)-Ser(OBzl)-Tyr(O-2-Br-Cbz)-6,7[2-(S-3-amino-2-oxo-pyrrolidin-1-yl)-S-2-isopropylmethylacetyl]-Arg-(Tos)-Pro-NHEt, obtained from the previous experiment, is treated at 0° C. for 1 hour with anhydrous hydrogen fluoride (10 ml) in presence of anisole (1.5 ml) and dimethylphosphite (1 ml). The excess reagents are removed in vacuo. The residue is washed three times with ether, then dissolved in (1:1)-water-acetonitrile solution containing 2% acetic acid (30 ml) and lyophilized. The crude product is purified by HPLC to give N-(1-Naphthylpropionyl)-Ser-Tyr-6,7[1-(S-3-amino-2-oxo-pyrroli din-1-yl)-S-2-isopropylmethylacetyl]-Arg-Pro-NHEt.

EXAMPLE 12

N-(alpha)-Morpholinocarbonyl-1-Nal-Ser-Tyr-D-Trp-Leu-Arg-Pro-NHEt

N-(alpha)-Morpholinocarbonyl-(1)-Nal-Ser-Tyr-D-Trp-Leu-Arg-Pro-NHEt is prepared according to the following steps:

(a) N-(alpha)-Morpholinocarbonyl-3-(1-naphthyl)alanine methyl ester 3-(1-Naphthyl)alanine methyl ester hydrochloride (46 mmole) is suspended in dry toluene (200 ml) and heated to 100° C. After a constant temperature is reached, phosgene is bubbled through the mixture for a period of 1 hour. The mixture is then purged with a stream of dry nitrogen and allowed to cool to room temperature. The toluene is removed in vacuo. The oily residue solidifies on cooling to give N-(alpha)-isocyano-3-(1-naphthyl)alanine methyl ester.

N-(alpha)isocyano-3-(1-naphthyl)alanine methyl ester (9.5 mmole) is dissolved in dry methylene chloride (35 ml) and cooled to 0° C. Morpholine (10 mmole) is added dropwise to the solution, and the resultant mixture is stirred overnight at room temperature. The mixture is then diluted to twice its volume, washed with water three times, and then with saturated brine. The organic extract is dried over $Na_2SO_4$ and concentrated in vacuo to give N-(alpha)-morpholinocarbonyl-3-(1-naphthyl)alanine methyl ester.

(b)
N-(alpha)-Morpholinocarbonyl-3-(1-naphthyl)alanine

N-(alpha)-morpholino-carbonyl-3-(1-naphthyl)alanine methyl ester (5.1 mmole) is dissolved in dioxane (10 ml) and cooled to 0° C. 1M solution of LiOH (5 ml) is added dropwise with stirring. After the addition is complete the mixture is allowed to warm to room temperature and stirring is continued overnight. The solvent is removed in vacuo and the residue is dissolved in water. The aqueous solution is first washed with ethyl acetate to remove unreacted compound, then acidified with 1N HCl to pH 3 and extracted three times with ethyl acetate. The last extracts are dried over $Na_2SO_4$ and concentrated in vacuo to give N-(alpha)-morpholinocarbonyl-3-(1-naphthyl)alanine.

(c) Boc-Ser(OBzl)-Tyr(O-2-Br-Cbz)-D-Trp(N formyl)-Leu-Arg(Tos)-Pro-O-Resin

Boc-Ser(OBznl)-Tyr(O-2-Br-Cbz)-D-Trp(N-formyl)-Leu-Arg(Tos)-Pro-O-Resin (0.9 mmole) is prepared using the solid phase synthetic procedure described in Example 1.

(d)
N-(alpha)-Morpholinocarbonyl-3-(L-naphthyl)alanyl-Ser(OBzl)-Tyr(O-2-Br-Cbz)-D-Trp(N-formyl)-Leu-Arg(Tos)-Pro-O-Resin.

Boc -Ser(OBzl)-Tyr(O-2-Br-Cbz)-D-Trp(N-formyl)-Leu-Arg(Tos)-Pro-O-Resin (0.9 mmole) previously obtained from step (e) is deblocked and coupled with 0.3M DMF solution of N-(alpha)-morpholinocarbonyl-3-(1-naphthyl)alanine in a 2.5 molar excess using the solid phase synthetic procedure described in Example 1 to give the desired peptide-resin.

(e) 
N-(alpha)-Morpholinocarbonyl3-(1-aphthyl)alanyl-Ser-Tyr-D-Trp-Leu-Arg-Pro-NHEt N-(alpha)-Morpholinocarbonyl-3-(1-naphthyl)alanyl-Ser(OBzl)-Tyr(O-2-Bz-Cbz)-D-Trp(N-formyl)-Leu-Arg-(Tos)-Pro-O-Resin, previously obtained from step (d), is treated with ethylamine at room temperature for 48 hours. The ethylamine is evaporated and the residue is stirred with methanol (60 ml) for 30 minutes. The resin is filtered and the filtrate is concentrated in vacuo. The residue is triturated with water, filtered, and dried over $P_2O_5$ to give N-(alpha)-morpholinocarbonyl-3-(1-naphthyl)alanyl-Ser-(OBzl)-Tyr(O-2-Br-Cbz)-D-Trp(N-formyl)-Leu-Arg(Tos)-Pro-NHEt. This protected peptide is treated at 0° for 1 hour with anhydrous HF (10 ml) containing anisole (1 ml) and dimethyl phosphite (0.5 ml). The excess reagents are removed in vacuo. The residue is washed three times with ether, then dissolved in (1:1:0.01) water acetonitrile-acetic acid solution (30 ml), and the solution is lyophilized. The crude product is purified using HPLC to give N-(alpha)-morpholinocarbon-3-(1-naphthyl)alanyl-Ser-Tyr-D-Trp-Leu-Arg-Pro-NHEt.

EXAMPLE 13

Using the procedure described in Example 11, but substituting 1-naphthylpropionic acid with the appropriate acids in the synthesis of intermediate (e), the following compounds can be prepared:

N-(1-Naphthylacetyl) seryl-tyrosyl-6,7-[2-(S-3-amino-2-oxo-pyrrolidin-1 -yl)-S-2-isopropylmethylacetyl]arginyl prolylethylamide.

N-(1-Naphthoxyacetyl)-seryl-tyrosyl-6,7-[2-(S-3-amino-2-oxo-pyrrolidin-1-yl)-S-2-isopropylmethyl acetyl]-arginyl-prolylethylamide.

N-(3-Indolepropionyl)-seryl-tyrosyl-6,7 -[2-(S-3-amino-2-oxo-pyrrolidin-1-yl)-S-2-isopropylmethyl acetyl]-arginyl-prolylethylamide.

N-(3-Indoleacetyl)-seryl tyrosyl-6,7-[2-(S-3-amino-2-oxo-pyrrolidin-1-yl)-S-2-isopropylmethyl acetyl]-arginyl-prolylethylamide.

N-(1-Adamantylacetyl)-seryl-tyrosyl-6,7-[2-(S-3-amino-2-oxo pyrrolidin-1-yl)-S-2-isopropylmethyl acetyl]-arginyl-prolylethylamide.

N-(3-Indoloyl)-seryl-tyrosyl-6,7-[2-(S-3-amino-2-oxo-pyrrolidin-1-yl)-S-2-isopropylmethylacetyl]-arginyl-prolylethylamide.

N-(Phenylacetyl)-seryl-tyrosyl-6,7-[2-(S-3-amino-2-oxo pyrrolidin-1-yl)-S-2-isopropylmethylacetyl]-arginyl-prolylethylamide.

N-(para-Chloro-phenylacety)-seryl-tyrosyl-6,7-[2-(S-3-amino-2-oxo-pyrrolidin-1-yl)-S-2-isopropylmethylacetyl]-arginyl-prolylethylamide.

N-(para-Fluoro-phenylacetyl)-seryl-tyrosyl-6,7-[2-(S-3-amino-2-oxo-pyrrolidin-1-yl)-S-2-isopropylmethylacetyl]-arginyl-prolylethylamide.

N-(Cinnamoyl)-seryl-tyrosyl-6,7-[2-(S-3-amino-2-oxo-pyrrolidin-1-yl)-S-2-isopropylmethylacetyl]-arginyl-prolylethylamide.

EXAMPLE 14

N-[2-(1-Naphthylmethyl)-4-(morpholineamido)-succinyl)-Ser-Tyr-D-Arg-Leu-Arg-Pro-NHEt N-[2-(1-Naphthylmethyl)-4-(morpholineamido)-succinyl]-Ser-Tyr-D-Arg-Leu-Arg-Pro-NHEt is synthesized according to the following synthetic steps:

(a)
N-[3-(1-Naphthylmethylene)]-4-(carboethoxy)succinic acid

To a solution of sodium ethoxide in ethanol, prepared by dissolving sodium (0.25 mole) in dry ethanol (130 ml), are added with stirring under nitrogen 1-naphthylaldehyde (0.145 mole) and diethylsuccinate (0.145 mole). The reaction mixture is refluxed for 3 hours. The solvent is removed in vacuo and the residue is dissolved in water and extracted twice with ether. The ether extract is discarded. The aqueous solution is cooled, acidified to pH 3 with cold concentrated HCl, and extracted three times with ether. The extract is dried over $Na_2SO_4$ and concentrated to give N-[3-(1-naphthylmethylene)-4-(carboethoxy)succinic acid as a heavy syrup in 89% yield.

(b) N-[3-(1-Naphthylmethyl)]-4-(carboethoxy)-succinic acid

N-[3-(1-Naphthylmethylene)]-4-(carboethoxy)succinic acid (0.13 mole), previously obtained from step (a), is hydrogenated under atmospheric pressure in ethanol (250 ml) and in the presence of 10% Pd/C (3.7 g). The catalyst is filtered and the filtrate is concentrated in vacuo. The residue is chromatographed on a silica gel column using (1:1) hexane-ethyl acetate to give racemic N-[3-(1-naphthylmethyl)]-4-(carboethoxy) succinic acid in quantitative yield.

(c) Ethyl N-[1-(1-Naphthylmethyl)-4-(morpholineamido)succinate

To a solution of N-[3-(1-naphthylmethyl)]-4-(carboethoxy)succinic acid (36 mmole) in DMF (15 ml) cooled to 0° C. are sequentially added HOBt (90 mmole), morpholine (30 mmole), 1 (3-dimethylaminopropyl)-3-ethylcarbodiimide hydrochloride (30 mmole), and N-ethylmorpholine (30 mmole). The solution is stirred at 0° C. for 2 hours and at room temperature for 48 hours. The solvent is removed in vacuo and the residue is dissolved in ethyl acetate, washed three times with 5% $NaHCO_3$, twice with 1N HCl, and twice with saturated brine, dried over $Na_2SO_4$ and concentrated to give ethyl N-[1-(1-naphthylmethyl)-4-(morpholineamido)-succinate as a crude oil. This is taken to the next step without further purification.

(d) N-[2-(1-Naphthylmethyl)-4-(morpholineamido)succinic acid

Ethyl-N-[2-(1-Naphthylmethyl)-4-(morpholineamido)-succinate (20 mmole) is dissolved in dioxane (30 ml) and to the solution is added at 0° C. 2N sodium hydroxide (30 ml). The mixture is stirred at room temperature for 24 hours. The solvent is removed in vacuo and the residue is dissolved in water. The aqueous solution is extracted twice with ethyl acetate to remove unhydrolyzed ester. The aqueous solution is cooled to 0° C., acidified with 1N HCl to pH 3, and extracted three times with ethyl acetate. The extract is dried over $Na_2SO_4$ and concentrated in vacuo. The residue is purified by silica gel column chromatography using (9:1) methylene chloride-methanol to give pure N-[2-(1-naphthylmethyl)-4-(morpholineamido)-succinic acid as a colorless heavy oil.

(f) N-[2-(1-Naphthylmethyl)-4-(morpholineamido)succinyl]-Ser-Tyr-D-Arg-Leu-Arg-Pro-NHEt N-[2-(1-naphthylmethyl)-4-(morpholineamido)succinic acid from step (d) is coupled with BOCSer(OBzl)Tyr-(O-2-Br-Cbz)-D-Arg(Tos)-Leu-Arg(Tos)-Pro-O-Resin (presynthesized using solid phase) using the solid phase synthetic procedure described in Example 12, but substituting Boc-D-Trp(N-formyl) with Boc-D-Arg(Tos) and N-(alpha)-morpholinocarbonyl-3-(1-naphthyl)alanine with N-[2-(1-naphthylmethyl)-4-(morpholineamido)-succinic acid. The peptide is cleaved from the resin with ethylamine and the protecting groups are removed with HF in the presence of anisole and dimethylphosphite as previously described. The crude product is purified with HPLC to give N-[2-(1-naphthylmethyl)-4-(morpholineamido)-succinyl]-Ser-Tyr-D Arg-Leu-Arg-Pro-NHEt.

EXAMPLE 15

Using the procedure described in Example 12, but substituting the morpholine in step (a) with the appropriate secondary and primary amines and substituting with the appropriate amino acids, the following compounds can be prepared:

N-(alpha)-Morpholinocarbonyl-D-3-(1-naphthyl)alanyl-seryl-tyrosyl-D-tyrosyl-leucyl-arginyl-prolylethylamide.

N-(alpha)-Morpholinocarbonyl-D-3-(4-chlorophenyl)alanyl-seryl-tyrosyl-D-prolyl-leucyl-arginyl-prolylethylamide.

N-(alpha)-Diethylaminocarbonyl-3-(1-naphthyl)alanyl-seryl-tyrosyl-D-tryptyl-leucyl-arginyl-prolylethylamide.

N-(alpha)-Piperidinocarbonyl-3-(1-naphthyl)alanyl-seryl-tyrosyl-D-arginyl-leucyl-arginyl-prolylethylamide.

N-(alpha)-Butylcarbonyl-3-(1-naphthyl)alanyl-seryl-tyrosyl-D-arginyl-leucyl-arginyl-prolylethylamide.

N-(alpha)-(N'-methylpiperazino)carbonyl-3-(1-naphthyl)alanyl-seryl-tyrosyl-D-leucyl-leucyl-arginyl-prolylethylamide.

N-(alpha)-Phenethylaminocarbonyl-3-(1-naphthyl)alanyl-seryl-tyrosyl-D-arginyl-leucyl-arginyl-prolylethylamide.

EXAMPLE 16

Using the procedure described in Example 14, but substituting the morpholine in step (e) with the appropriate secondary and primary amines and substituting with the appropriate amino acids, the following compounds can be prepared (as the L- or D-isomer at position 3):

N-[2-(1-Naphthylmethyl)-4-(diethylamido)succinyl]-seryl-tyrosyl-D-lysyl-leucyl-arginyl-prolylethylamide.

N-[2-(1-Naphthylmethyl)-4-(piperidineamido)succinyl]-seryl-tyrosyl-D-tryptyl-leucyl-arginyl-prolylethylamide.

N-[2-(1-Naphthylmethyl)-4-(butylamido)succinyl]-seryl-tyrosyl-D-tyrosyl-leucyl-arginyl-prolylethylamide.

N-[2-(1-Naphthylmethyl)-4-(N'-methylpiperazineamido)-succinyl]seryl-tyrosyl-D-arginyl-leucyl-arginyl-prolylethylamide.

N-[2-(1-Naphthylmethyl)-4-(phenethylamido)succinyl]-seryl-tyrosyl-D-seryl-leucyl-arginyl-prolylethylamide.

EXAMPLE 17

Using the procedure described in Example 12, but substituting 3-(1-naphthyl)alanine methyl ester hydrochloride in step (a) with D-3-(1-naphthyl)alanine methyl ester, D or L p-methoxytyrosine methyl ester hydrochloride, D or L phenylalanine methyl ester hydrochloride, D or L tryptophan methyl ester hydrochloride, D or L p-chlorophenylalanine methyl ester hydrochloride, D or L 3-(2-naphthyl)alanine methyl ester hydrochloride, D or L p-fluorophenylalanine methyl ester, D or L 3-(3-pyridyl)alanine methyl ester, and D or L 3-(3-quinolyl)alanine methyl ester, respectively, the following compounds can be prepared:

N-(alpha)-Morpholinocarbon-yl-D-3-(1-naphthyl)alanyl-seryl-tyrosyl-D-tyrosyl-leucyl-arginyl-prolylethylamide.

N-(alpha)-Morpholinecarbonyl-(D or L)-(O-methyl)-tyrosyl-seryl-tyrosyl-D-tryptyl-leucyl-arginyl-prolylethylamide.

N-(alpha)-Morpholinocarbonyl-(D or L)-tyrosyl-seryl-tyrosyl-D-tyrosyl-leucyl arginyl-prolylethyl amide.

N-(alpha)-Morpholinecarbonyl-(D or L)-phenylalanyl-seryl-tyrosyl-D-tryptyl-leucyl-arginyl-prolyl ethylamide.

N-(alpha)-Morpholinecarbonyl-(D or L)-tryptyl-seryl-tyrosyl-D-leucyl-leucyl-arginyl-prolylethylamide.

N-(alpha)-Morpholinecarbonyl(D or L)-(p-chlorophenyl)alanyl-seryl-tyrosyl-D-tryptyl-leucyl-arginyl-prolylethylamide.

N-(alpha)-Morpholinecarbonyl-(D or L)-3-(2-naphthyl)alanyl-seryl-tyrosyl-D-tryptyl-leucyl-arginyl-prolylethylamide.

N-(alpha)-Morpholinecarbonyl-(D or L)-(p-fluorophenyl)alanyl-seryl-tyrosyl-D-prolyl-leucyl-arginyl-prolylethylamide.

N-(alpha)-Morpholinecarbonyl-(D or L)-3-(3-pyridyl)alanyl-seryl-tyrosyl-D-tryptyl-leucyl-arginyl-prolylethylamide.

N-(alpha)-Morpholinecarbonyl-(D or L)-3-(3-quinolyl)alanyl)-seryl-tyrosyl-D-seryl(O-t-butyl)-leucyl-arginyl-prolylethylamide.

EXAMPLE 18

Using the procedure described in Example 14 but substituting 1-naphthylaldehyde used in step (a) with p-methoxybenzaldehyde, benzaldehyde, 3-indolecarboxaldehyde, p-chlorobenzaldehyde, p-fluorobenzaldehyde, 2-naphthylaldehyde, 3-pyridinecarboxaldehyde and 3-quinolinecarboxaldehyde, respectively, and substituting with the appropriate amino acids, the following compounds (with D or L configuration at position 3) can be prepared:

N-[2-(p-methoxybenzyl)-4-(morpholineamido)succinyl]-seryl-tyrosyl-D-3-pyridylalanyl-leucyl-arginyl-prolylethylamide.

N-[2-Benzyl-4-(morpholineamido)-succinyl]-seryl-tyrosyl-D-leucyl-leucyl-arginyl-prolylethylamide.

N-[2-(3-indolemethyl)-4-(morpholineamido)succinyl]-seryl-tyrosyl-D-leucyl-leucyl-arginyl-prolylethylamide.

N-[2-(p-Chlorobenzyl)-4-(morpholineamido)succinyl]-seryl-tyrosyl-D-tryptyl-leucyl-arginyl-prolylethylamide.

N-[2-(p-fluorobenzyl)-4-morpholineamido)succinyl]-seryl-tyrosyl-D-tyrosyl-leucyl-arginyl-prolylethylamide.

N-[2-(2-Naphthylmethyl)-4-(morpholineamido)succinyl]-seryl-tyrosyl-D-lysyl(N-epsilon-nicotinyl)leucyl-arginyl-prolylethylamide.

N-[-2-(3-Pyridylmethyl)-4-(morpholineamido)succinyl]-seryl-tyrosyl-D-seryl-leucyl-arginyl-prolylethylamide.

N-[2-(3-Quinolylmethyl)-4-(morpholineamido)succinyl]-seryl-tyrosyl-D-seryl-leucyl-arginyl-prolylethylamide.

EXAMPLE 19

Using a synthesis program identical to that described in Example 1 and substituting the appropriate acids and amino acids using N-alpha-BOC-N-delta-CBZ-D-Orn and N-alpha-BOC-D-Gln for position 6 and using the procedure previously described, the following compounds were prepared, purified by HPLC, and characterized as their trifluoroacetate salts: (4-9) [N-(3-(3-indole) propionyl)-Ser$^4$-D-Orn$^6$-Pro$^9$N-HEt]LHRH(49), $R_T$=12.4 minutes, Fab Mass spec m/e 947 (M+H)$^+$; AA Anal.; 0.9 Pro; 1.0 Arg; 1.1 Leu; 1.0 Orn; 1.0 Tyr; 0.6 Ser.

(4-9)[N-(3-(3-Indole)propionyl)-Ser$^4$-D-Gln$^6$-Pro$^9$-NHEt]LHRH(50), $R_T$=14.64 minutes, Fab Mass spec m/e 961 (M+H)$^+$; AA Anal.; 1.0 Pro; 1.0 Arg; 1.0 Leu; 1.0 Glu; 1.0 Tyr; 0.6 Ser.

EXAMPLE 20

N-(3-(3-Indole)propionyl)-Ser-Tyr-N-delta-ethyl-D-Gln-Leu-Arg-ProNHEt(51)

Using a synthesis program identical to that described in Example 19 but substituting N-BOC-D-glutamic acid delta-benzyl ester at position 6, the benzyl ester group was replaced by ethylamine during the cleavage of the peptide from the resin, to give N-(3-(3-indole)propionyl)-Ser-Tyr-N-delta-ethyl-D-Gln-Leu-Arg-ProNHEt as trifluoroacetate salt. The product was purified by HPLC and eluted as a single peak with $R_T$=17.17 minutes. Fab Mass spec. m/e 989 (M+H)$^+$. AA Anal.: 1.0 Pro; 1.0 Arg; 1.0 Leu; 1.0 Glu, 1.0 Tyr; 0.6 Ser.

EXAMPLE 21

Using the general procedure described in Example 1, 2 g of the peptide resin N-(3-(3-indole)propionyl)-Ser-(OBzl)-Tyr(O-2-Br-CBZ)-D-N-(epsilon)FMOC-Lys-Leu-Arg(Tos)-Pro-O-Resin was prepared. The resin was treated with 20% piperidine in methylene chloride overnight at room temperatures to cleave the FMOC group. The resin was filtered, washed three times with (1:1) DMF methylene chloride, three times with methylene chloride, and dried under vacuum overnight. The resin was split in two equal portions, one was coupled with nicotinic acid and the other with picolinic acid using the same peptide synthesizer protocol described in Example 1. After work-up and HPLC purification the following compounds were obtained: (4-9)[N-(3-(3-Indole)propionyl-Ser$^4$-D-Lys$^6$(N-epsilon-nicotinyl)-Pro$^9$-NHEt]LHRH(52), $R_T$=14.86 minutes, Fab Mass spec. m/e 1066 (M+H)$^+$. AA Anal.: 1.1 Pro; 1.0 Arg; 1.0 Leu; 0.9 Lys; 0.9 Tyr; 0.8 Ser. (4-9) [N-(3-(3-Indole)-propionyl-Ser$^4$-D-Lys$^6$(N-picolinoyl)-Pro$^9$NHEt] LHRH(53), $R_T$=18.8 minutes, Fab Mass spec. m/e 1066 (M+H)$^+$. AA Anal.: 1.1 Pro; 1.0 Arg; 1.0 Leu; 0.9 Lys; 0.9 Tyr; 0.8 Ser.

EXAMPLE 22

N-(3-(3-Indole)propionyl)-Ser-Tyr-D-Lys-(N-epsilon-isp)-Leu-Arg-Pro-NHEt(54)

Using the same procedure described in Example 8, but substituting 3-indolepropionic acid in place of 1-naphthylacetic acid, N-(3-(3-indole)propionyl-Ser-Tyr-D-Lys(N-epsilon-isp)-Leu-Arg-ProNHEt was obtained and purified by HPLC, eluted as a single peak with $R_T$=13.79 minutes, Fab Mass spec. m/e 1003 (M+H)$^+$. AA Anal.: 1.2 Pro; 1.0 Arg; 1.0 Leu; 1.0 Lys; 0.9 Tyr; 0.6 Ser.

EXAMPLE 23

N-(3-(3-Indole)propionyl)-Ser-Tyr-D-Lys-Leu-Arg-Pro-NHEt(55)

Using the same procedure described in Example 21 but first removing the FMOC group and afterwards cleaving the peptide from the resin with ethylamine, and following the same work-up, N-3-(3-indole)propionyl-Ser-Tyr-D-Lys-Leu-Arg-ProNHET was obtained and purified by HPLC. The compound eluted with $R_T$=32.30 minutes, Fab Mass spec. m/e 961 $(M+H)^+$. AA Anal.: 1.1 Pro; 1.1 Arg; 1.0 Leu; 1.0 Lys; 0.9 Tyr; 0.6 Ser.

EXAMPLE 24

N-(3-(3-Indole)propionyl)-Ser-Tyr-D-2-Nal-Leu-Arg-Pro-D-AlaNH$_2$(56)

Using the same procedure described in Example 1 but starting with BOC-D-Ala-NH-Resin (4-methyl-benzhydrylamine resin), cleaving the peptide from the resin and the protecting groups with HF, followed by work up and HPLC purification, N-(3-(3-indole)propionyl)-Ser-Tyr-D-2-Nal-Leu-Arg-Pro-D-AlaNH$_2$ can be obtained as the trifluoroacetate salt.

EXAMPLE 25

N-(3-(1-Naphthyl)propionyl)-Ser-Tyr-D-Tyr-Leu-Arg-Pro-SarNH$_2$

Using the same procedure described in Example 24 but starting with BOC Sar NH Resin (4-methyl-benzhydrylamine resin) and adding 0.1% of 4-dimethylaminopyridine to the BOC-Pro DMF solution before coupling, substituting position 3 with 1-naphthylpropionic acid, following with the same procedure and work-up as previously described, N-(3-(1-naphthyl)propionyl)-Ser-Tyr-D-Tyr-Leu-Arg-Pro-SarNH$_2$ can be obtained and purified by HPLC.

EXAMPLE 26

N-(3-(3-Indole)propionyl)-Ser-N-Me-Tyr-D-Trp-Leu-Arg-Pro-NHEt(54)

Using the same procedure described in Example 1 but adding 0.1% of 4-dimethylaminopyridine to the BOC-Ser(OBzl) DMF solution before coupling, following with the same procedure and work-up as previously described, N-3-(3-indole)propionyl-Ser-N-Me-Tyr-D-Trp-Leu-Arg-ProNHEt can be obtained and purified by HPLC.

EXAMPLE 27

N-(3-(3-Indole)propionyl)-Ser-Tyr-D-N-Me-Leu-Leu-Arg-Pro-NHEt(58)

Using the same procedure described in Example 1, but adding 0.1% of 4-dimethylaminopyridine to the BOC-Tyr-(O-2-Br-CBZ) DMF solution before coupling and substituting the appropriate amino acids and acid, after work-up and HPLC purification N-(3-(3-indole)propionyl)-Ser-Tyr-D-N-Me-Leu-Leu-Arg-ProNHEt can be obtained.

EXAMPLE 28

N-(3-(1-Naphthyl)propionyl)-N-Me-Ser-Tyr-D-Trp-Leu-Arg-Pro-D-AlaNH$_2$

Using the same procedure described in Example 24 but adding 0.1% of 4-dimethylaminopyridine to the 3-(1-naphthyl)propionic acid DMF solution before coupling, followed by the same work up and HPLC purification as previously described, N-(3-(1-naphthyl)propionyl)-N-Me-Ser-Tyr-D-Trp-Leu-Arg-Pro-D-AlaNH$_2$ can be obtained.

EXAMPLE 29

N-(3-(1-Naphthyl)propionyl)-Ser-Tyr-D-2-Nal-Leu-N-Me-Arg-Pro-D-AlaNH$_2$

Using the same procedure described in Example 24 but adding 0.1% of 4-dimethylaminopyridine to the N-BOC-Leu DMF solution before coupling, substituting with the appropriate amino acids and acids, followed by the same work-up and HPLC purification as previously described, N-3-(1-naphthyl)propionyl-Ser-Tyr-D-2-Nal-Leu-N-Me-Arg-Pro-D-AlaNH$_2$ can be obtained.

EXAMPLE 30

N-(3-(1-Naphthyl)propionyl)-Ser-N-Me-Tyr-D-Trp-N-Me-Leu-Arg-Pro-D-AlaNH$_2$

Using the same procedure described in Example 24 but adding 0.1% of 4-dimethylaminopyridine to the DMF solutions of N-BOC-D-tryptophan(N-indole-formyl) and N-BOC-Ser(OBzl) before coupling, substituting with the appropriate amino acids and acids, followed by the same work-up and HPLC purification as previously described, N-(3-(1-naphthyl)propionyl)-Ser-N Me-Tyr-D-Trp-N-Me-Leu-Arg-Pro-D-AlaNH$_2$ can be obtained.

EXAMPLE 31

N-(5,6-Dihydro-5,5-dimethyl-2-oxo-3-phenyl-1-(2H)-pyrazine acetyl)-Ser-Tyr-D-Trp-Leu-Arg-ProNHEt 1,2-Diamino-2-methylpropane (7.4 ml) and methylbenzoyl formate (10 ml) were dissolved in absolute ethanol (250 ml) and heated at reflux for 18 hours. The reaction was concentrated to half volume and hot hexane (225 ml) was added. The solution was filtered and the filtrate was placed in the refrigerator overnight. The resultant crystals were filtered, and dried to give 5,6-dihydro-5,5-dimethyl-2-oxo-3-phenyl-2-(2H)-pyrazine. Mass Spec. m/c 203 $(M+H)^+$. Anal Calcd. for $C_{12}H_{14}N_2O$ ½$H_2O$: C, 69.70; H, 6.82; N, 13.55. Found: C, 70.10; H, 7.04; N, 13.63. 5,6-Dihydro-5,5-dimethyl-2-oxo-3-phenyl (3.5 g) was dissolved in dry THF (35 ml), 1M THF solution of sodium bis-trimethylsilyl amide (17.2 ml) was cannulated into the solution under nitrogen. After the addition was complete, the solution was stirred for an additional 20 minutes. Ethyl bromoacetate (2 ml) in dry THF (2 ml) was added dropwise. Stirring was continued for 48 hours. The solution was then poured into water and extracted twice with ether. The ethereal extracts were washed with saturated brine, dried, and concentrated in vacuo to give ethyl 5,6-dihydro-5,5-dimethyl-2-oxo-3-phenyl-1-(2H)-pyrazineacetate as white crystals. This ester was dissolved in dioxane (7 ml) and treated with 1M aqueous solution of LiOH (6.8 ml) at room temperature overnight. The solution was concentrated in vacuo, the residue was treated with 1N HCl (15 ml) and extracted with ethyl acetate. The organic extracts were dried and concentrated in vacuo to give 5,6-dihydro-5,5-dimethyl-2-oxo-3-phenyl1-(2H)-pyrazineacetic acid as white crystals; NMR (CDCl$_3$): 7.4–7.8 (m, 5H), 4.3 (s, 2H), 3.5 (s, 2H), 1.4 (s, 6H). Mass spec m/e 261 $(M+H)^+$. Using the same procedure and protocol described in Example 1, 5,6-dihydro-5,5-dimethyl-2-oxo-3-phenyl-1-(2H)-pyrazineacetic acid can be coupled to BOC-Ser(OBzl)-Tyr-(O-2-Br-CBZ)-D-Trp-(N-formyl)-Leu-Arg-(Tos)-Pro-O-Resin to give after cleavage from the resin, removal of protecting groups, work up and HPLC purification N-(5,6-dihydro-5,5-dimethyl-2-oxo-3-phenyl-1-(2H)-pyrazineacetyl)-Ser-Tyr-D-Trp-Leu-Arg-ProNHEt.

EXAMPLE 32

N-alpha-Morpholinocarbonyl-Phe-Trp-Ser-Tyr-D-Trp-Leu-Arg-ProNHET (59)

Using the same procedure described in Example 12 but substituting phenylalanine methyl ester hydrochloride in place of 3-(1-naphthyl)alanine methyl ester hydrochloride, N-(alpha)-morpholino-carbonyl phenylalanine was synthesized. This compound was coupled to BOC-Phe-Trp(N-formyl)-Ser(O-Bzl)-Tyr(O-2-Br-CBZ)-D-Trp(N-formyl)-Leu-Arg(Tos)-Pro-O-Resin using the peptide synthesizer and the same protocol described in Example 12. Work-up and purification first on LH-20 Sephadex column followed by HPLC gave N-(alpha)-morpholinocarbonyl-Phe-Trp-Ser-Tyr-D-Trp-Leu-Arg-ProNHEt; $R_T = 2.45$ min; Fab Mass spec m/e 1294 $(M+H)^+$; AA Anal: 1.1 Pro, 1.1 Arg, 1.0 Leu; 1.3 Trp; 0.9 Tyr; 0.4 Ser; 0.9 Phe.

N-(alpha)-Morpholinocarbonyl-Phe-Trp-Ser-Tyr-D-Trp-Leu-Arg-ProNHEt was also prepared by a complete solid phase synthesis according to the following procedure: BOC-Phe-Trp(N-formyl)-Ser(O-Bzl)-Tyr-(O-2-Br-CBZ)-D-Trp(N-formyl)-Leu-Arg(Tos)-Pro-O-Resin was prepared from 1 g of BOC-Pro-O-Resin Merrifield resin using the peptide synthesizer protocol previously described. The BOC-protecting group was removed from the peptide resin using the "deblock" solution (TFA/ anisole/dimethylphosphite in $CH_2Cl_2$), washed with "base wash" (diisopropylethylamine/$CH_2Cl_2$), washed several times with $CH_2Cl_2$ and DMF, and dried. To this resin was added a solution of 0.3M 1,1-carbonyldiimidazole in DMF (18 ml) in 10 fold excess and mixed (by bubbling nitrogen through) for 5 minutes. The excess of reagents and solvent were removed, the resin was washed several times with $CH_2Cl_2$/DMF and dried. To this resin was added a solution of 0.3M morpholine in (1:1) DMF-$CH_2Cl_2$ (18 ml) and mixed overnight at room temperature. The excess of reagents and solvent were removed, the resin was washed several times with $CH_2Cl_1$-DMF, dried and subsequently was treated with ethylamine to cleave the peptide from the resin using the same conditions described in Example 1. The dry peptide was treated with HF to cleave the protecting groups. Following work-up and HPLC purification N-(alpha)-morpholinocarbonyl-Phe-Trp-Ser-Tyr-D-Trp-Leu-Arg-ProNHEt was obtained as the trifluoroacetate salt.

EXAMPLE 33

N-(alpha)-Morpholinocarbonyl-Phe-Trp-Ser-Tyr-D-Arg-Leu-Arg-ProNHEt (60)

Using the same procedure described in Example 32 but substituting BOC-D-Arg(Tos) for BOC-D-Trp-(N-indole-formyl), N-(alpha)-morpholinocarbonyl-Phe-Trp-Ser-Tyr-D-Arg-Leu-Arg-ProNHEt was obtained and purified by HPLC. The compound eluted with $R_T = 25.47$ minutes; Fab Mass spec m/e 1264 $(M+H)^+$; AA Anal; 1.1 Pro, 2.0 Arg, 1.0 Leu, 0.8 Tyr, 0.6 Ser, 0.8 Trp; 1.1 Phe.

EXAMPLE 34

N-(alpha)-Morpholinocarbonyl-D-4-Cl-Phe-D-Trp-Ser-Tyr-D-Trp-Leu-Arg-Pro-D-AlaNH$_2$ and N-(alpha)-Morpholinocarbonyl-4-F-Phe-Trp-Ser-Tyr-D-Trp-Leu-Arg-Pro-D-AlaNH$_2$ Using the same procedure described in Example 12 but substituting D-4-Cl-phenylalanine methyl ester hydrochloride and 4-F-phenylalanine methyl ester hydrochloride in place of phenylalanine methyl ester hydrochloride, N-(alpha)-morpholinocarbonyl-D-4-Cl-phenylalanine and N-(alpha)-morpholinocarbonyl-4-F-phenylalanine were obtained respectively. Using the same procedure and resin described in Example 24 and substituting with the appropriate amino acids, N-(alpha)-morpholinocarbonyl-D-4-Cl Phe D-Trp-Ser-Tyr-D-Trp-Leu-Arg-Pro-D-AlaNH$_2$ and N-(alpha) morpholinocarbon-yl-4-F-Phe-Trp-Ser-Tyr-D-Trp-Leu-Arg-Pro-D-AlaNH$_2$ can be obtained.

EXAMPLE 35

N-[3-(4-Imidazolyl)propionyl]-Trp-Ser-Tyr-D-Trp-Leu-Arg-ProNHEt (61)

Using the same protocol described in Example 1 the resin BOC-Trp(N formyl)-Ser(OBzl)-Tyr-(O-2-Br-CBZ)-D-Trp-(N-formyl)-Leu-Arg(Tos)-Pro-O-Resin was synthesized and coupled to 3-(N-im-BOC-4-imidazolyl)propionic acid. The peptide was cleaved from the resin, worked-up, and purified by HPLC to give N-[3-(4-imidazolyl)propionyl]-Trp-Ser-Tyr-D-Trp-Leu-Arg-ProNHEt. The compound was eluted with $R_T = 24.7$ minutes; Fab Mass spec m/e 1156 $(M+H)^+$, AA Anal.: 1.1 Pro, 1.0 Arg, 1.1 Leu, 1.2 Trp, 0.9 Tyr, 0.5 Ser.

EXAMPLE 36

Using the same procedure describe in Example 35 and substituting with the appropriate amino acids and acids, the following compounds were synthesized, purified by HPLC, and characterized as their trifluoroacetate salts:

(3-9)[N-Cinnamoyl-Trp$^3$-D-Trp$^6$-Pro$^9$-NHEt]LHRH (62), $R_T = 16.56$ minutes, Fab Mass spec m/e 1164 $(M+H)^+$; AA Anal: 1.0 Pro, 1.1 Arg, 1.0 Leu, 1.0 Trp, 1.0 Tyr, 0.6 Ser.

(3-9)[N-Cinnamoyl-Trp$^3$-D-Leu$^6$-Pro$^9$-NHEt]LHRH (63), $R_T = 8.87$ minutes, Fab Mass spec m/e 1091 $(M+H)^+$; AA Anal: 1.0 Pro, 0.9 Arg, 2.0 Leu, 1.0 Tyr, 0.6 Ser, 0.5 Trp.

(3-9)[N-((para-Dimethylamino)cinnamoyl)-Trp$^3$-D-Leu$^6$-Pro$^9$-NHEt]LHRH (64), $R_T = 12.25$ minutes, Fab Mass spec m/e 1134 $(M+H)^+$; AA Anal: 1.1 Pro, 1.3 Arg, 2.1 Leu, 0.8 Tyr, 0.5 Ser, 0.3 Trp.

(3-9)[N-(3-Phenylpropionyl)-Trp$^3$-D-Trp$^6$-Pro$^9$-NHEt]LHRH (65), $R_T = 7.0$ minutes, Fab Mass spec m/e 1166 $(M+H)^+$; AA Anal: 1.0 Pro, 1.0 Arg, 1.0 Leu, 1.9 Trp, 1.3 Tyr, 0.7 Ser.

(3-9)[N-(3-Phenylpropionyl)-Trp$^3$-D-Leu$^6$-Pro$^9$-NHEt]LHRH (66), $R_T = 13.28$ minutes, Fab Mass spec m/e 1093 $(M+H)^+$; AA Anal: 1.0 Pro, 1.0 Arg, 2.0 Leu, 1.0 Tyr, 0.6 Ser, 0.7 Trp.

(3-9)[N-(Phenylacetyl)-Trp$^3$-D-Trp$^6$-Pro$^9$-NHEt]LHRH (67), $R_T = 37.5$ minutes, Fab Mass spec m/e 1079 $(M+H)^+$; AA Anal: 1.0 Pro, 0.9 Arg, 1.1 Leu, 1.2 Trp, 0.9 Tyr, 0.6 Ser.

(3-9)[N-(Phenylacetyl)-Trp$^3$-D-Leu$^6$-Pro$^9$-NHEt]LHRH (68), $R_T = 18.34$ minutes, Fab Mass spec m/e 1079 (M+H)+; AA Anal: 1.0 Pro, 1.0 Arg, 2.1 Leu, 0.9 Tyr, 0.7 Ser, 0.7 Trp.

EXAMPLE 37

N-(5,6-Dihydro-5,5-dimethyl-2-oxo-3-phenyl-1-(2H)-pyrazine acetyl)-Trp-Ser-Tyr-D-Trp-Leu-Arg-ProNHEt 5,6-Dihydro-5,5-dimethyl-2-oxo-3-phenyl-1-(2H)-pyrazineacetic acid, synthesized according to the procedure described in Example 31, can be coupled to BOC-Trp(N-indole-formyl)-Ser(OBzl)-Tyr(O-2-Br-CBZ)-D-Trp-(N-indole-formyl)-Leu-Arg(Tos)-Pro-O-Resin following the same procedure and protocol described in Example 1. After cleavage of the peptide from the resin with ethylamine, removal of the protecting groups with HF, work up and HPLC purification N-(5,6-dihydro5,5-dimethyl-2-oxo-3-phenyl-1-(2H)-pyrazineacetyl)-Trp-Ser-Tyr-D-Trp-Leu-Arg-ProNHEt can be obtained.

EXAMPLE 38

N-(5,6-Dihydro-5,5-dimethyl-2-oxo-3-phenyl-1-(2H)-pyrazineacetyl-Trp-Ser-Tyr-D-2-Nal-Leu-Arg-Pro-D-AlaNH$_2$ 5,6-Dihydro-5,5-dimethyl-2-oxo-3-phenyl-1-(2H)-pyrazineacetic acid, synthesized according to the procedure described in Example 31, can be coupled to BOC-Trp(N-formyl)-Ser(OBzl)-Tyr(O-2-Br-CBZ)-D-2-Nal-Leu-Arg(Tos)-Pro-D-Ala-NH-Resin (4-methyl-benzhydrylamine resin) using the same procedure described in Example 24. The peptide and the protecting groups are cleaved from the resin with HF. Work up and HPLC purification can give N-(5,6-dihydro-5,5-dimethyl-2-oxo-3-phenyl-1-(2H)-pyrazineacetyl)-Trp-Ser-Tyr-D-2-Nal-Leu-Arg-Pro-D-AlaNH$_2$.

EXAMPLE 39

N-(5,6-Dihydro-5,5-dimethyl-2-oxo-3-(para-Cl-phenyl)1-(2H)-pyrazineacetyl-Trp-Ser-Tyr-D-Trp-Leu-Arg-Pro-D-AlaNH$_2$ and
N-(5,6-Dihydro-5,5-dimethyl-2-oxo-3-(para-F-phenyl)-1-(2H)-pyrazineacetyl-Trp-Ser-Tyr-D-Trp-Leu-Arg-Pro-D-AlaNH$_2$ Using the procedure described in Example 31 but substituting methylbenzoyl formate with methyl (para-chloro)benzoyl formate and with methyl (para-fluoro)benzoyl formate, respectively, 5,6-dihydro-5,5-dimethyl-2-oxo-3-(para-chloro)phenyl-1-(2H)-pyrazineacetic acid and 5,6-dihydro-5,5-dimethyl-2-oxo-3-(para-fluoro)phenyl-1-(2H)-pyrazineacetic acid can be obtained. These acids can be separately coupled to BOC-Trp-(N-formyl)-Ser(OBzl)-Tyr(O-2-Br-CBZ)-D-Trp-(N-formyl)-Leu-Arg(Tos)-Pro-D-Ala-NH-Resin according to the procedure described in Example 24. The peptides and the protecting groups are cleaved with HF. Work up and HPLC purification gives
N-(5,6-dihydro-5,5-dimethyl-2-oxo-3-(para-Cl-phenyl)-1-(2H)-pyrazineacetyl)-Trp-Ser-Tyr-D-Trp-Leu-Arg-Pro-D-AlaNH$_2$ and
N-(5,6-dihydro-5,5-dimethyl-2-oxo-3-(para-F-phenyl)-1-(2H)-pyrazineacetyl)-Trp-Ser-Tyr-D-Trp-Leu-Arg-Pro-D-AlaNH$_2$, respectively.

EXAMPLE 40

N-(3-(5-Imidazolyl)propionyl)-His-Trp-Ser-Tyr-D-Trp-Leu-Arg-Pro-NHEt (69)

Using the same procedure described in Example 31 but substituting positions 1, 2, 3 and 6 with 3-[N-BOC-5-imidazolyl]propionic acid, N-BOC-His(N-im-CBZ), N-BOC-Trp(N-indole-formyl), and N-BOC-D-Trp(N-indole-formyl), respectively, after work-up and purification by HPLC, N-(3-(5-imidazolyl)propionyl)-His-Trp-Ser-Tyr-D-Trp-Leu-Arg-Pro-NHEt was obtained. The compound eluted with R$_T$=23.20 min; Fab Mass spec m/e 1293 (M+H)+; AA Anal: 1.0 Pro; 1.0 Arg; 1.1 Leu; 1.2 Trp; 1.0 Tyr; 0.5 Ser.

EXAMPLE 41

Using the same procedure described in Example 40 and substituting with the appropriate acids and amino acids the following compounds can be prepared:
N-(3-phenylpropionyl)-histidyl-tryptyl-seryl-tyrosyl-D-tyrosyl-leucyl-arginyl-prolylethylamide.
N-[3-(4-Chlorophenyl)propionyl]-histidyl-tryptyl-seryl-tyrosyl-D-tryptyl-leucyl-arginyl-prolylethylamide.
N-(4-Fluorophenylacetyl)-D-phenylalanyl-D-tryptyl-seryl-tyrosyl-D-2-naphthylalanyl-leucyl-arginyl-prolylethylamide.
N-(1-Naphthylacetyl)-D-histidyl-D-tryptyl-seryl-tyrosyl-D-tyrosyl-leucyl-arginyl-prolylethylamide.
N-[3-(2-Naphthyl)propionyl]-histidyl-tryptyl-seryl-tyrosyl-D-tryptyl-leucyl-arginyl-prolylethylamide.
N-(3-Nicotinoyl)-D-phenylalanyl-D-tryptyl-seryl-tyrosyl-D-tyrosyl-leucyl-arginyl-prolylethylamide.

EXAMPLE 42

Using the same resin and procedure described in Example 38 and substituting with the appropriate acids and amino acids the following compounds can be prepared:
N-[3-(4-Chlorophenyl)propionyl]-histidyl-tryptyl-seryl-tyrosyl-D-2-naphthylalanyl-leucyl-arginyl prolyl-D-alanylamide.
N-[3-(4-Fluorophenyl)propionyl]-D-phenylalanyl-D-tryptyl-seryl-tyrosyl-D-tryptyl-leucyl-arginyl-prolyl-D-alanylamide.
N-[3-(1-Naphthylacetyl)]-D-4-Cl-phenylalanyl-D-tryptyl-seryl-tyrosyl-D-tyrosyl-leucyl-arginyl-prolyl-D-alanylamide.
N-(3-Nicotinoyl)-phenylalanyl-tryptyl-seryl-tyrosyl-D-seryl-leucyl-arginyl-prolylethylamide.

EXAMPLE 43

Using the procedure described in Example 41 and substituting with the appropriate acids, but adding 0.1% of 4-dimethylaminopyridine to the DMF solution of the acid or amino acid which is to be coupled with the preceding (with respect to the C-terminus) N-methyl-amino acid, as described in Example 3, the following compounds can be synthesized:
N-[3-(4-Chlorophenyl)propionyl]-N-methyl-phenylalanyl-tryptyl-seryl-tyrosyl-D-tryptyl-leucyl-arginyl-prolylethyl amide.
N-[3-(2-Naphthyl)propionyl]-N-methyl-D-phenylalanyl-D-tryptyl-seryl-N-methyl-tyrosyl-D-tyrosyl-leucyl-arginyl-prolylethylamide.

N-[(4-Chlorophenyl)acetyl]]-phenylalanyl-tryptyl-N-methyl-seryl-tyrosyl-D-tryptyl-leucyl-arginyl-prolylethylamide.

N-[3-(4-fluorophenyl)propionyl]-tryptyl-seryl-N-methyl-tyrosyl-D-tryptyl-leucyl-arginyl-prolylethylamide.

EXAMPLE 44

N-(Cyclopentylcarbonyl)-Phe-Trp-Ser-Tyr-D-Arg-Leu-Arg-Pro-NHEt (70)

Using the same procedure described in Example 1 but substituting positions 1, 2, 3 and 6 with cyclopentylcarboxylic acid, N-BOC-Phe, N-BOC-Trp(N-indole-formyl), and N-BOC-N-D-Arg(Tos), respectively, followed by work up and HPLC purification as previously described, N-cyclopentylcarbonyl-Phe-Trp-Ser-Tyr-D-Arg-Leu-Arg-Pro-NHEt bis-trifluoroacetate was obtained. The compound eluted with $R_T$=28.2 minutes; Fab Mass spec m/e 1247 (M+H)$^+$; AA Anal: 1.0 Pro; 1.9 Arg; 1.0 Leu; 1.0 Tyr; 0.4 Ser; 0.6 Trp; 1.0 Phe.

EXAMPLE 45

N-(5,6-Dihydro-5,5-dimethyl-2-oxo-3-phenyl-1-(2H)-pyrazineacetyl)-His-Trp-Ser-Lys-D-Trp-Leu-Arg-ProNHEt (71).

Using the same procedure described in Example 1 but substituting positions 1, 2, 3, 5 and 6 with 5,6-dihydro-5,5-dimethyl-2-oxo-3-phenyl-1-(2H)-pyrazineacetic acid (described in Example 31), N-BOC-His(N-im-CBZ), N-BOC-Trp(N-indole-formyl), N-BOC-Lys(N-epsilon-CBZ), and N-BOC-D-Trp(N-indole-formyl), respectively, following work-up and HPLC purification, N-(5,6-dihydro-5,5-dihydro- 5,5-dimethyl-2-oxo-3-phenyl-1-(2H)-pyrazineacetyl)-His-Trp-Ser-Lys-D-Trp-Leu-Arg-ProNHEt was obtained as the bis trifluoroacetate salt. The compound eluted with $R_T$=34.4 minutes; Fab Mass spec m/e 1378 (M+H)$^+$; AA Anal: 1.1 Pro; 1.2 Arg; 1.1 Leu; 1.5 Trp; 0.9 Lys; 0.6 Ser; 1.0 His.

EXAMPLE 46

N-Acetyl-Phe-Trp-Ser-Tyr-D-Trp-Leu-Arg-ProNHEt (72)

Using the same procedure described in Example 43 but substituting acetic acid for cyclopentycarboxylic acid and N BOC-D-Arg(Tos) with N-BOC-D-Trp(N-indole-formyl); following work-up and HPLC purification N-acetyl-Phe-Trp-Ser-Tyr-D-Trp-Leu-Arg-ProNHEt was obtained as the trifluoroacetate salt. The compound eluted with $R_T$=20 minutes; Fab Mass spec m/e 1223 (M+H)$^+$; AA Anal: 1.0 Pro; 1.0 Arg; 1.0 Leu; 1.2 Trp; 0.9 Tyr; 0.5 Ser; 0.7 Phe.

EXAMPLE 47

N-Acetyl-D-Phe-N-Me-1-Nal-Ser-N-Me-Tyr-D-Trp-Leu-Arg-ProNHEt

Using the procedure described in Example 43 and substituting the following positions with the following acids and amino acids: 1 with acetic acid, 2 with BOC-D-Phe containing 0.1% 4-dimethylaminopyridine in DMF, 3 with BOC-N-Me-1-Nal, 4 with BOC-Ser(OBzl) containing 0.1% 4-dimethylaminopyridine in DMF, 5 with BOC-N Me-Tyr(O-2,6-di-Cl-Bzl), 6 with BOC-D-Trp(N-indole-formyl), 7 with BOC-Leu, and 8 with BOC-Arg(Tos), following work up and HPLC purification N-acetyl-D-phenylalanyl-N-methyl-1-naphthylalanyl-seryl-N-methyl-tyrosyl-D-tryptyl-leucyl-arginyl-prolylethyl amide can be obtained.

EXAMPLE 48

N-Cyclopentylcarbonyl-4-Cl-D-Phe-Trp-N-Me-Ser-Tyr-D-Trp-Leu-Arg-ProNHEt

Using the procedure described in Example 47 and substituting with the appropriate acid and amino acids but adding 0.1% of 4-dimethyl aminopyridine only to the DMF solution of BOC D-Trp(N-indole-formyl) at position 3 before coupling with the BOC-N-Me-Ser, following work up and HPLC purification cyclopentylcarbonyl-D-4-Cl-phenylalanyl-D-tryptyl-N-methyl-seryl-tyrosyl-D-tryptyl-leucyl-prolylethyl amide can be obtained.

EXAMPLE 49

N-(3-(4-Cl phenyl)propionyl)-D-Trp-Ser-N-Me-Tyr-D-Trp-Leu-N-Me-Arg-ProNHEt

Using the procedure described in Example 48 and substituting with the appropriate acid and amino acids but adding before coupling 0.1% of 4-dimethylaminopyridine only to the DMF solutions of BOC-Ser(OBzl) at position 4 and BOC-Leu at position 7, following work-up and HPLC purification N-(3-(4-Cl-phenyl)propionyl)-D-tryptyl-seryl-N-methyl-tyrosyl-D-tryptyl-leucyl-N-methyl-arginyl-prolylethyl amide can be obtained.

EXAMPLE 50

N-(3-(4-F-phenyl)propionyl)-D-Trp-Ser-N-Me-Tyr-D-Trp -Leu-Arg-Pro-D-AlaNH$_2$

Using the same procedure described in Example 24 and substituting with the appropriate acids and amino acids but adding 0.1% of 4-dimethylaminopyridine to the DMF solution of BOC Ser(OBzl) before coupling to BOC-N-Me-Tyr(O-2,6-di-Cl-Bzl), following work-up and HPLC purification N-(3-(4-F-phenyl)propionyl) -D-tryptyl-seryl-N-methyl-tyrosyl-D-tryptyl-leucyl -arginyl-prolyl-D-alanylamide can be obtained.

EXAMPLE 51

N-(3-(4-Cl phenyl)propionyl)-1-Nal-N-Me-Ser-Tyr -D-Trp-Leu-Arg-Pro-SarNH$_2$

Using the same procedure described in Example 24 but starting with BOC-Sar NH-Resin (4-methylbenzhydrylamine resin), substituting with the appropriate acid and amino acid, and adding 0.1% of 4-dimethylaminopyridine to the DMF solution of BOC-1-Nal before coupling to BOC-N-Me-Ser(OBzl), following work up and HPLC purification, N-(3-(4-Cl-phenyl)propionyl)-1-naphthylalanyl-N-methyl-seryl-tyrosyl -D-tryptyl-leucyl-arginyl-prolyl-sarcosylamide can be obtained.

EXAMPLE 52

Using the same procedure described in Example 35 and substituting the appropriate acids and amino acids, the following compounds were prepared, purified by HPLC, and characterized as their trifluoroacetate salts:
(4-9)[N-(3-(4-Hydroxyphenyl)acetyl) -Ser$^4$-D-Trp$^6$-Pro$^9$NHEt]LHRH(73), $R_T$= 33.9 min; Fab Mass spec m/e 982 (M+H)$^+$; AA Anal: 1.04 Pro; 1.1 Arg; 1.03 Leu; 0.98 Trp; 0.93 Tyr; 0.53 Ser.

(4-9)[N-(3-(4-Fluorophenyl)acetyl) -Ser⁴-D-Trp⁶-Pro⁹NHEt]LHRH(74), $R_T$=38.53 min; Fab Mass spec m/e 984 (M+H)⁺; AA Anal: 0.92 Pro; 0.9 Arg; 1.09 Leu; 0.94 Trp; 1.01 Tyr; 0.39 Ser.

(4-9)[N-(3-(4-Chlorophenyl)acetyl) -Ser⁴-D-Trp⁶-Pro⁹NHEt]LHRH(75), $R_T$=37.22 min; Fab Mass spec m/e 1000 (M+H)⁺; AA Anal: 1.10 Pro; 1.05 Arg; 0.99 Leu; 0.9 Trp; 0.91 Tyr; 0.5 Ser.

(4-9)[N-(3-(4-Hydroxyphenyl)propionyl) -Ser⁴-D-Trp⁶-Pro⁹NHEt]LHRH(76), $R_T$=34.37 min; Fab Mass spec m/e 996 (M+H)⁺; AA Anal: 1.0 Pro; 1.1 Arg; 1.0 Leu; 0.7 Trp; 0.9 Tyr; 0.3 Ser.

(4-9)[N-(3-(4-Fluorophenyl)propionyl) -Ser⁴-D-Trp⁶-Pro⁹NHEt]LHRH(77), $R_T$=41 min; Fab Mass spec m/e 998 (M+H)⁺; AA Anal: 1.0 Pro; 1.0 Arg; 1.0 Leu; 1.0 Trp; 1.0 Tyr; 0.6 Ser.

(4-9)[N-(3-(4-Methoxyphenyl)propionyl) -Ser⁴-D-Trp⁶-Pro⁹NHEt]LHRH(78), $R_T$=39.82 min; Fab Mass spec m/e 1010 (M+H)⁺; AA Anal: 1.0 Pro; 1.0 Arg; 1.0 Leu; 0.9 Trp; 1.0 Tyr; 0.6 Ser.

(4-9)[N-(3-(4-Trifluoromethylphenyl) propionyl)-Ser⁴-D-Trp⁶-Pro⁹NHEt]LHRH(79), $R_T$=44.5 min; Fab Mass spec m/e 1048 (M+H)⁺; AA Anal: 1.06 Pro; 1.06 Arg; 1.0 Leu; 0.76 Trp; 0.95 Tyr; 0.93 Ser.

(4-9)[N-(3-(3-Indole)propionyl) -Ser⁴-D-Thia⁶-Pro⁹NHEt]LHRH(80), $R_T$=39.7 min; Fab Mass spec m/e 986 (M+H)⁺; AA Anal: 1.0 Pro; 1.0 Arg; 1.0 Leu; 0.7 Thia; 1.0 Tyr; 0.6 Ser.

EXAMPLE 53

N-[(1-Adamantyl)acetyl]-Ser-N-Me-Tyr-D-Trp-Leu-Arg-Pro -NHEt(81)

Using the same procedure described in Example 1 and substituting 1-naphthylacetyl with 1-adamantylacetyl, BOC-Tyr-(O-2-Br-Cbz) with BOC-N-Me-Tyr()-2,6-di-Cl-Bzl), BOC-D-Leu with BOC-D-Trp (N-indole-formyl), and adding 0.1% of 4-dimethyl aminopyridine to the DMF solution of BOC-Ser(OBzl-) before coupling, following work up and HPLC purification using same conditions previously described, N-(1-adamantylacetyl)Ser-N-MeTyr-D-Trp-Leu-Arg-ProNHEt trifluoroacetate eluted at $R_T$=30.68 min; Fab Mass spec m/e 1038 (M+H)⁺; AA Anal: 0.99 Pro; 1.1 Arg; 1.0 Leu; 0.87 Trp; 0.44 Ser.

EXAMPLE 54

N-Acetyl-1-Nal-Ser-Tyr-D-Trp-Leu-Arg-ProNHEt (isomer A) (82) and N-acetyl-1-Nal Ser-Tyr-D-Trp Leu Arg proNHEt (isomer B) (83).

Using the same procedure described in Example 1 and substituting 1 naphthylacetic acid with N-acetyl-D,L-1-Nal and BOC-D-Leu with BOC-D-Trp (N-indole formyl), following with the usual work up (3-9)[N-Ac D,L-1-Nal³-D-Trp⁶-Pro⁹NHEt]LHRH was obtained as a racemic mixture. The two isomers were separated by HPLC to give (3-9)[N-Ac-1-Nal³-D-Trp⁶-Pro⁹NHEt]LHRH (82) isomer A, $R_T$=39.2 min; Fab Mass spec m/e 1087 (M+H)⁺; AA Anal: 1.04 Pro; 1.1 Arg; 1.02 Leu; 1.0 Trp; 0.93 Tyr; 0.36 Ser. And (3-9)[N-Ac-1-Nal³-D-Trp⁶-Pro⁹NHEt]LHRH (83) isomer B, $R_T$=40.2 min; Fab Mass spec m/e 1087 (M+H)⁺; AA Anal: 1.03 Pro; 1.05 Arg; 1.02 Leu; 1.1 Trp; 0.96 Tyr; 0.71 Ser.

EXAMPLE 55

N-Acetyl-2-Nal-Ser-Tyr-D-Trp-Leu-Arg ProNHEt (84)

Using the same procedure described in Example 1 and substituting 1 naphthylacetic acid with BOC-2-Nal and BOC-D-Leu with BOC-D-Trp(N-indole-formyl), following with deblocking and twice capping with N-acetyl-imidazole at the end of the synthesis, after work up and purification by HPLC (3-9)[N-Ac-2-Nal³-D-Trp⁶-Pro⁹NHEt]LHRH (84) was obtained, $R_T$=39.5 min; Fab Mass spec m/e 1087 (M+H)⁺; AA Anal: 0.99 Pro; 1.04 Arg; 1.04 Leu; 0.86 Trp; 0.98 Tyr; 0.57 Ser.

EXAMPLE 56

Using the same procedure described in Example 35 and substituting with the appropriate amino acids and acids, the following compounds were synthesized, purified by HPLC, and characterized as their trifluoroacetate salt:

(3 9)[N-(3-(4-Chlorophenyl)propionyl)-D-Trp³,⁶-Pro⁹NHEt]LHRH(85), $R_T$=44.6 min; Fab Mass spec m/e 1200 (M+H)⁺; AA Anal: 1.0 Pro; 1.2 Arg; 1.0 Leu; 2.0 Trp; 1.0 Tyr; 0.5 Ser.

(3-9)[N-(3-(4-Chlorophenyl)propionyl)-D -Tyr³-D-Trp⁶-Pro⁹NHEt]LHRH(86), $R_T$=44.16 min; Fab Mass spec m/e 1177 (M+H)⁺; AA Anal: 1.0 Pro; 0.9 Arg; 1.0 Leu; 0.9 Trp; 2.0 Tyr; 0.8 Ser.

(3-9)[N-(3-(4-Chlorophenyl)propionyl) -Tyr³-D-Trp⁶-Pro⁹NHEt]LHRH(87), $R_T$=40.18 min; Fab Mass spec m/e 1177 (M+H)⁺; AA Anal: 1.1 Pro; 1.1 Arg; 1.0 Leu; 0.6 Trp; 1.9 Tyr; 0.6 Ser.

(3-9)[N-(3-(2-Fluorophenyl)propionyl) -Trp³-D-Trp⁶-Pro⁹NHEt]LHRH(88), $R_T$=45 min; Fab Mass spec m/e 1184 (M+H)⁺; AA Anal: 1 0 Pro; 1.0 Arg; 1 0 Leu; 1.5 Trp; 1.0 Tyr; 0.3 Ser.

(3-9)[N-(3-(3-Fluorophenyl)propionyl) -Trp³-D-Trp⁶-Pro⁹NHEt]LHRH(89), $R_T$=46.3 min; Fab Mass spec m/e 1087 (M+H)⁺; AA Anal: 1.0 Pro; 1.1 Arg; 1.1 Leu; 0.8 Trp; 0.9 Tyr; 0.6 Ser.

(3-9)[N-(3-(2,4-Difluorophenyl)propionyl) -D-Trp³,⁶-Pro⁹NHEt]LHRH(90), $R_T$=46.75 min; Fab Mass spec m/e 1202 (M+H)⁺; AA Anal: 1.0 Pro; 1.1 Arg; 1.0 Leu; 1.4 Trp; 0.9 Tyr; 0.6 Ser.

(3-9)[N-(3-(4-Fluorophenyl)propionyl) -D-Trp³,⁶Pro⁹NHEt]LHRH(91), $R_T$=47.14 min; Fab Mass spec m/e 1184 (M+H)⁺; AA Anal: 1.0 Pro; 0.9 Arg; 1.0 Leu; 1.6 Trp; 1.0 Tyr; 0.3 Ser.

(3-9)[N-(3-(4-Fluorophenyl)propionyl) -Trp³-D-Tyr⁶-Pro⁹NHEt]LHRH(92), $R_T$=41.34 min; Fab Mass spec m/e 1161 (M+H)⁺; AA Anal: 1.0 Pro; 1.2 Arg; 1.0 Leu; 1.1 Trp; 2.0 Tyr; 0.6 Ser.

(3-9)[N-(3-(4-Fluorophenyl)propionyl) -D-Tyr³,⁶-Pro⁹NHEt]LHRH(93), $R_T$=28.27 min; Fab Mass spec m/e 1139 (M+H)⁺; AA Anal: 1.0 Pro; 1.1 Arg; 1.0 Leu; 2.9 Tyr; 0.4 Ser.

(3-9)[N-(3-(4-Fluorophenyl)propionyl) -D-Trp³-D-2-Nal⁶-Pro⁹NHEt]LHRH(94), $R_T$=50.75 min; Fab Mass spec m/e 1195 (M+H)⁺; AA Anal: 1.0 Pro; 1.1 Arg; 1.0 Leu; 0.7 Trp; 1.0 Tyr; 0.4 Ser.

(3-9)[N-(3-(4-Methoxyphenyl)propionyl) -Trp³-D-Trp⁶-Pro⁹NHEt]LHRH(95), $R_T$=46 min; Fab Mass spec m/e 1196 (M+H)⁺; AA Anal: 1.0 Pro; 1.2 Arg; 1.0 Leu; 1.0 Tyr; 1.7 Trp; 0.5 Ser.

(3-9)[N-(3-(4-Trifluoromethylphenyl)propionyl) -Trp⁶-D-Pro⁹-NHEt]LHRH(96), $R_T$=45.65 min; Fab Mass spec m/e 1234 (M+H)+; AA Anal: 1.0 Pro; 1.1 Arg; 1.0 Leu; 2.0 Trp; 1.0 Tyr; 0.5 Ser.

(3-9)[N-(3-(4-Fluorophenyl)propionyl) -Trp³-D-Trp⁶-Pro⁹NHEt]LHRH(97), $R_T$=43.87 min; Fab Mass spec m/e 1184 (M+H)+; AA Anal: 1.0 Pro; 1.1 Arg; 1.0 Leu; 2.2 Trp; 1.0 Tyr; 0.3 Ser.

(3-9)[N-(3-(4-Chlorophenyl)propionyl) -Trp³-D-Trp⁶-Pro⁹NHEt]LHRH(98), $R_T$=49.5 min; Fab Mass spec m/e 1200 (M+H)+; AA Anal: 1.0 Pro; 1.2 Arg; 1.0 Leu; 2.0 Trp; 1.0 Tyr; 0.5 Ser.

(3-9)[N-(3-(4-Hydroxyphenyl)propionyl) -Trp³-D-Trp⁶-Pro⁹NHEt]LHRH(99), $R_T$=39.67 min; Fab Mass spec m/e 1182 (M+H)+; AA Anal 1.0 Pro; 1.1 Arg; 1.0 Leu; 2.4 Trp; 1.0 Tyr; 0.6 Ser.

(3-9)[N-(3-(4-Fluorophenyl)propionyl)-D -Trp³,⁶-Pro⁴,⁹NHEt]LHRH(100), $R_T$=49.89 min; Fab Mass spec m/e 1194 (M+H)+; AA Anal: 2.0 Pro; 1.1 Arg; 1.0 Leu; 2.0 Trp; 1.0 Tyr.

(3-9)[N-(2-Indolecarbonyl)-Trp³-D-Trp⁶-Pro⁹NHEt]LHRH (101), $R_T$=37.62 min; Fab Mass spec m/e 1177 (M+H)+; AA Anal: 1.1 Pro; 1.1 Arg; 1.0 Leu; 0.8 Trp; 1.0 Tyr; 0.7 Ser.

(3-9)[N-(5-Fluoro-2-indolecarbonyl)-D -Trp³,⁶-Pro⁹-NHEt]LHRH(102), $R_T$=47.2 min; Fab Mass spec m/e 1195 (M+H)+; AA Anal: 1.0 Pro; 1.0 Leu; 0.9 Trp; 1.0 Tyr; 0.4 Ser.

(3-9)[N-(3-Indolepropionyl)-D-Trp³,⁶-Pro⁹-NHEt]LHRH (103), $R_T$=4.3 min; Fab Mass spec m/e 1205 (M+H)+; AA Anal: 1.1 Pro; 1.1 Arg; 1.0 Leu; 1.7 Trp; 1.) Tyr; 0.4 Ser.

(3-9)[N-(4-Chlorophenyl)acetyl-Trp³-D-Trp⁶-Pro⁹NHEt]LHRH(104), $R_T$=47.15 min; Fab Mass spec m/e 1186 (M+H)+; AA Anal: 1.0 Pro; 1.1 Arg; 1.0 Leu; 1.4 Trp; 1.0 Tyr; 0.4 Ser.

(3-9)[N-(4-Hydroxyphenyl)acetyl-Trp³-D -Trp⁶-Pro⁹NHEt]LHRH(105), $R_T$=40 min; Fab Mass spec m/e 1168 (M+H)+; AA Anal: 1.0 Pro; 0.9 Arg; 1.0 Leu; 1.2 Trp; 1.0 Tyr; 0.4 Ser.

(3-9)[N-(4-Trifluoromethylphenyl)acetyl -Trp³,⁶-Pro⁹NHEt]LHRH(106), $R_T$=35.7 min; Fab Mass spec m/e 1220 (M+H)+; AA Anal: 1.0 Pro; 1.1 Arg; 1.0 Leu; 2.3 Trp; 1.0 Tyr; 0.4 Ser.

EXAMPLE 57

Using the procedure described in Example 32, and substituting with the appropriate amino acids in the synthesis followed by work up and HPLC purification, the following compounds were obtained as trifluoroacetate salts:

(2 9)[N-(N-alpha-Morpholinocarbonyl)-Phe²-D-Trp³,⁶-Pro⁹NHEt]LHRH (107), $R_T$=26.24 min; Fab Mass spec m/e 1294 (M+H); AA Anal: 0.86 Pro; 0.9 Arg; 1.0 Leu; 1.54 Trp; 1.02 Tyr; 0.42 Ser; 0.98 Phe.

(2-9)[N-(N-alpha-Morpholinocarbonyl)-Phe²-D-Tyr³-D-Trp⁶-Pro⁹NHEt]LHRH (108), $R_T$=24.55 min; Fab Mass spec m/e 1271 (M+H); AA Anal: 0.94 Pro; 0.87 Arg; 1.03 Leu; 0.63 Trp; 2.03 Tyr; 0.5 Ser; 1.0 Phe.

(2-9)[N-(N-alpha-Morpholinocarbonyl)-His²-D-Trp⁶-Pro⁹NHEt]LHRH (109), $R_T$=32.29 min; Fab Mass spec m/e 1284 (M+H); AA Anal: 1.04 Pro; 1.08 Arg; 1.0 Leu; 1.61 Trp; 0.97 Tyr; 0.23 Ser; 0.92 His.

(2-9)[N-(N-alpha-Morpholinocarbonyl)-1-Nal²-D-Trp⁶-Pro⁹NHEt]LHRH (110), $R_T$=47.09 min; Fab Mass spec m/e 1344 (M+H)+; AA Anal: 0.99 Pro; 1.08 Arg; 1.02 Leu; 2.05 Trp; 0.99 Tyr; 0.6 Ser.

(2-9)[N-(N-alpha-Morpholinocarbonyl)-D-2-Nal²-D-Trp⁶-Pro⁹NHEt]LHRH (111), $R_T$=47.3 min; Fab Mass spec m/e 1344 (M+H)+; AA Anal: 1.05 Pro; 0.98 Arg; 1.02 Leu; 2.7 Trp; 0.98 Tyr; 0.48 Ser.

(2-9)[N-(N-alpha-Morpholinocarbonyl)-4-Cl -Phe²-D-Trp⁶-Pro⁹NHEt]LHRH (112), $R_T$=47.8 min; Fab Mass spec m/e 1328 (M+H)+; AA Anal: 1.1 Pro; 1.1 Arg; 1.0 Leu; 1.8 Trp; 0.9 Tyr; 0.5 Ser.

(2-9)[N-(N-alpha-Morpholinocarbonyl)-D,L-4-F-Phe²-D-Trp⁶-Pro⁹NHEt]LHRH (113), $R_T$=42 min; Fab Mass spec m/e 1312 (M+H)+; AA Anal: 1.0 Pro; 1.1 Arg; 1.0 Leu; 2.2 Trp; 1.0 Tyr; 0.6 Ser.

EXAMPLE 57

Using the same procedure described in Example 32, substituting the appropriate amino acids in the synthesis and adding 0.1% of 4-N,N-dimethylaminopyridine to the amino acid solution to be coupled with the N-methylamino group of the preceding amino acid in the synthesis, after work up and HPLC purification the following compounds were obtained as trifluoro acetate salts:

(2-9)[N-(N-alpha-Morpholinocarbonyl)-Phe²-N-Me-Tyr⁵-D-Trp⁶-Pro⁹-NHEt]LHRH (114), $R_T$=27.68 min; Fab Mass spec m/e 1308 (M+H)+; AA Anal: 0.97 Pro; 1.0 Arg; 1.05 Leu; 2.06 Trp; 0.5 Ser; 0.98 Phe.

(2-9)[N-(N-alpha-Morpholinocarbonyl)-Phe²-N-Me-Ser⁴-D-Trp⁶-Pro⁹-NHEt]LHRH (115), $R_T$=20.8 min; Fab Mass spec m/e 1308 (M+H)+; AA Anal: 1.00 Pro; 0.9 Arg; 0.93 Leu; 1.93 Trp; 0.9 Tyr; 1.1 Phe.

(2-9)[N-(N-alpha-Morpholinocarbonyl)-Phe²-N-Me-Tyr³-D-Trp⁶-Pro⁹NHEt]LHRH (116), $R_T$=39.26 min; Fab Mass spec m/e 1285 (M+H)+; AA Anal: 1.04 Pro; 0.92 Arg; 0.99 Leu; 1.31 Trp; 0.96 Tyr; 0.37 Ser; 0.93 Phe.

EXAMPLE 58

N-(N-alpha-Morpholinocarbonyl)-Phe-Trp-Ser-Tyr-D-Lys(Nic) -Leu-Arg-ProNHEt (117)

Using the procedure described in Example 32 and substituting with the appropriate amino acids, the peptide resin N-(N-alpha-morpholinocarbonyl-Phe-Trp(N-CHO) -Ser(OBzl)-Tyr(O-2-Br-Cbz)-D-Lys(FMOC)-Leu-Arg(Tos)-Pro-O -Resin was prepared. This resin was treated overnight with 30% piperidine in DMF to remove the FMOC propecting group. The resin was washed three times with methylene chloride, dried, and then deblocked and coupled with nicotinic acid using the same protocol as before. The peptide was cleaved from the resin with anhydrous ethylamine at room temperature for 48 hours. The protecting groups were removed with HF at 0° C. for 1 hr in the presence of anisole. The crude peptide was purified by HPLC, using the same conditions described in Example 1, to give N-(N-alpha-morpholinocarbonyl)-Phe -Trp-Ser-Tyr-D-Lys(Nic)-Leu-Arg-ProNHEt as trifluoroacetate salt; $R_T$=20.1 min; Fab Mass spec m/e 1341 (M+H)+; AA Anal: 1.07 Pro; 0.7 Arg; 1.06 Leu; 0.97 Lys; 1.04 Tyr; 0.63 Ser; 0.93 Phe.

EXAMPLE 59

N-(N-alpha-Morpholino-carbonyl)-Phe-Trp-Ser-Tyr-D-Trp-Leu -Arg-Pro-D-AlaNH₂ (118)

Using the procedure described in Example 32 but starting with BOC-D-Ala-NH-Resin (benzhydrylamine resin) and substituting with the appropriate amino acids, the peptide resin N-(N-alpha morpholinocarbonyl)-Phe -Trp-(N-formyl)-Ser(OBzl)-Tyr(O-2-Br-Cbz)-D-Trp-(N-formyl) -Leu-Arg-(Tos)-Pro-D-Ala-NH-Resin was obtained. This was treated with HF/anisole at 0° C. for 1 hr to cleave the peptide from the resin and remove the protecting groups. After work-up the crude peptide was purified by HPLC to give N-(N-alpha-morpholinocarbonyl)-Phe-Trp-Ser-Tyr-D -Trp-Leu-Arg-Pro-DAlaNH$_2$ as trifluoroacetate salt; $R_T$=29.22 min; Fab Mass spec m/e 1337 (M+H)$^+$; AA Anal: 0.94 Ala; 1.03 Pro; 0.93 Arg; 1.03 Leu; 2.12 Trp; 0.99 Tyr; 0.55 Ser; 0.98 Phe.

EXAMPLE 60

N-(3-(4-Fluorophenyl)propionyl)-Trp-Ser-Tyr-D-Lys(-Nic) -Leu-Arg-Pro-NHEt (119) and N-(3-(4-Fluorophenyl)propionyl)-D-Trp-Ser-Tyr-D-Lys(Nic) -Leu-Arg-ProNHEt (120)

Using the procedure described in Example 1 and substituting with the appropriate amino acids, the peptide-resins N-(3-(4-fluorophenyl)propionyl)-Trp -(N-CHO)-Ser(OBzl)-Tyr(O-Br-Cbz)-D-Lys(FMOC)-Leu-Arg(Tos) -Pro-O-Resin and N-(3-(4-fluorophenyl)propionyl)-D-Trp -(N-CHO)-Ser(OBzl)-Tyr(O-Br-Cbz)-D-Lys(FMOC)-Leu-Arg -(Tos)-Pro-O-Resin were obtained. These were separately treated with 30% piperidine in DMF overnight to remove the FMOC groups, then coupled with nicotinic acid using the same protocol which was previously described. The peptides were cleaved from the resin with anhydrous ethylamine at room temperature for 48 hrs. After work-up and drying the crude peptides were treated with HF/anisole at 0° C. for 1 hr. After work-up and HPLC purification N-(3-(4-fluorophenyl)propionyl)-Trp-Ser -Tyr-D-Lys(Nic)-Leu-Arg-Pro-NHEt; $R_T$=37.2 min. Fab Mass spec m/e 1231 (M+H)$^+$; AA Anal: 0 9 Pro; 0.8 Arg; 1.1 Leu; 0.9 Lys; 1.0 Tyr; 0.5 Ser; 0.5 Trp and N-(3-(4-fluorophenyl)propionyl) -D-Trp-Ser-Tyr-D-Lys(Nic)-Leu-Arg-ProNHEt, $R_T$=35.9 min; Fab Mass spec m/e 1231 (M+H)$^+$; AA Anal: 1.0 Pro; 0.9 Arg; 1 1 Leu; 1.0 Lys; 1.0 Tyr; 0.5 Ser; 1.0 Trp; were obtained respectively.

EXAMPLE 61

N-(3-(4-Fluorophenyl)propionyl)-D-Trp-Ser-N-Me-Tyr-D-Trp -Leu-Arg-Pro-NHEt (120) and (3-9)[N-(3-(4-Fluorophenyl)propionyl)-D-Trp -N-Me-Ser-Tyr-D-Trp-Leu-Arg-ProNHEt (121)

Using the procedure described in Example 35 and substituting with the appropriate acids and amino acids, BOC-N-Me-Tyr()-2,4-di-Cl-Bzl) for compound 120 and BOC-N-Me-Ser(OBze) for compound 121, and adding 0.1% 4-dimethylaminopyridine to the amino acid solution to be coupled with the N-methylamino group of the preceding amino acid in the synthesis, after work up and HPLC purification N-(3-(4-fluorophenyl)propionyl-D-Trp -Ser-NMe-Tyr-D-Trp-Leu-Arg-ProNHEt, $R_T$=35.8 min; Fab Mass spec m/e 1198 (M+H)$^+$; AA Anal: 1.0 Pro; 1.0 Arg; 1.0 Leu; 1.2 Trp; 0.5 Ser; and (3-9)[N-(3 (4 fluorophenyl)propionyl]-D-Trp-N-Me-Ser-Tyr-D-Trp-Leu-Arg-ProNHEt, $R_T$=46.35 min; Fab Mass spec m/e 1198 (M+H)$^+$; AA Anal: 1.0 Pro; 1.1. Arg; 1.0 Leu; 1.9 Trp; 1.0 Tyr; were obtained respectively.

EXAMPLE 62

N-(3-(4-Fluorophenyl)propionyl)-D-Trp-Ser-N-Me-Tyr-D -Lys(Nic)-Leu-Arg-ProNHEt (122).

Using the same procedure described in Example 61 the peptide resin N-3-(4-fluorophenyl)propionyl-D-Trp (N-formyl)-Ser(OBzl)-N-Me-Tyr(O-2,6-di-Cl-Bzl)-D-Lys(FMOC) -Leu-Arg(Tos)Pro-O-Resin was prepared. Tis was treated with 30% piperidine in DMF overnight at room temperature to remove the FMOC group. After washing with methylene chloride and drying under vacuum the peptide resin was coupled with nicotinic acid using the s-ynthetic protocol previously described. The resin was subseguently treated with anhydrous ethylamine for 48 hours at room temperature to cleave the peptide from it. The protecting groups were removed upon treatment with HF/anisole at 0° C. for 1 hr. After work up and HPLC purification N-(3-(4-fluorophenyl)propionyl)-D-Trp -Ser-N-Me-Tyr-D-Lys(Nic)-Leu-Arg-ProNHEt, $R_T$=34.63 min; Fab Mass spec m/e 1245 (M+H)$^+$; AA Anal: 1.1 Pro; 0.8 Arg; 1.1 Leu; 0.9 Lys, 0.1 Ser; 0.9 Trp.

EXAMPLE 63

N-3-(4-Fluorophenyl)propionyl-D-Trp-(N-indole-formyl)-Ser -Tyr-D-Trp(N-indole-formyl)-Leu-Arg-Pro-D-AlaNH$_2$(123)

Using the procedure described in Example 1 but starting with BOC-D-Ala-NH-Resin (benzhydrylamine resin) and substituting with the appropriate amino acids and acid, the peptide-resin N-(3-(4-fluorophenyl)propionyl)-D -Trp(N-indole-formyl)-Ser(O-Bzl)-Tyr-(O-2-Br-Cbz)-D-Trp -(N-indole-formyl)-Leu-Arg(Tos)-Pro-D-Ala-NH-Resin was obtained. This was treated with HF/anisole at 0° C. for 1 h. After work-up and purification N-(3-(4-fluorophenyl)propionyl)-D-Trp(N-indole-formyl)-Ser -Tyr-D-Trp(N-indole-formyl)-Leu-Arg-Pro-D-AlaNH$_2$ was obtained as trifluoroacetate salt, $R_T$=44.63 min; Fab Mass spec m/e 1283 (M+H)$^+$; AA Anal: 1.0 Ala; 1.1 Pro; 1.0 Arg; 1.0 Leu; 2.3 Trp; 1.0 Tyr; 0.4 Ser.

EXAMPLE 64

Using the same procedure described in Example 32, and substituting morpholine in the synthesis with th appropriate amine the following compounds were prepared:

(2-9)[N-(N-alpha-Phenethylaminocarbonyl)-Phe$^2$-D-Trp$^6$-Pro$^9$NHEt]LHRH(124), $R_T$=48.63 min; Fab Mass spec m/e 1328 (M+H)$^+$; AA Anal: 0.96 Pro; 1.04 Arg; 1.05 Leu; 2.16 Trp; 0.99 Tyr; 0.42 Ser; 0.01 Phe.

(2-9)[N-(N-alpha-Cyclohexylaminocarbonyl)-Phe$^2$-D-Trp$^6$-Pro$^9$NHEt]LHRH(125), $R_T$=49.5 min; Fab Mass spec m/e 1306 (M+H)$^+$; AA Anal: 1.03 Pro; 1.0 Arg; 1.01 Leu; 1.24 Trp; 0.96 Tyr; 0.69 Ser; 0.04 Phe.

(2-9)[N-(N-alpha-Dicyclohexylaminocarbonyl)-Phe$^2$-D-Trp$^6$-Pro$^9$NHEt]LHRH(126), $R_T$=55 min; Fab Mass spec m/e 1388 (M+H)$^+$; AA Anal: 0.99 Pro; 1.03 Arg; 1.01 Leu; 2.08 Trp; 0.99 Tyr; 0.60 Ser; 0 45 Phe.

(2-9)[N-(N-alpha-Ethylaminocarbonyl)-Phe$^2$-D-Trp$^6$-Pro$^9$NHEt]LHRH(127), $R_T$=40.83 min; Fab Mass spec m/e 1252 (M+H)$^+$; AA Anal: 1.04 Pro; 1.2 Arg; 0.98 Leu; 1.07 Trp; 0.95 Tyr; 0.4 Ser; 0.09 Phe.

(2-9)[N-(N-alpha-N-methylpiperazinocarbonyl)-Phe²-D-Trp⁶-Pro⁹NHEt]LHRH(128), $R_T$=35.72 min; Fab Mass spec m/e 1307 (M+H)⁺; AA Anal: 0.98 Pro; 1.06 Arg; 1.03 Leu; 1.97 Trp; 1.01 Tyr; 0.48 Ser; 0.98 Phe.

EXAMPLE 65

N-(N-alpha-(N-Methylpiperazinosulfonyl))-Phe-Trp-Ser-Tyr -D-Trp-Leu-Arg-ProNHEt (129)

Using the procedure described in Example 35 the resin BOC Trp(N indole formyl) Ser(OBzl)-Tyr (O-2-Br-Cbz)-D-Trp(N-indole-formyl)-Leu-Arg(Tos)-Pro-O -Resin was synthesized and coupled to N-(N-alpha -(N-methylpiperazinosulfonyl))-Phe using coupling a protocol of two coupling of 6 hours each. The peptide was cleaved from the resin with ethylamine, and the protecting groups were cleaved with HF as previously described. The crude peptide was purified by HPLC to give N-(N-alpha-(N-methylpiperazinosulfonyl))-Phe-Trp -Ser-Tyr-D Trp-Leu-Arg-ProNHEt, $R_T$=36.32 min; Fab Mass spec m/e 1343 (M+H)⁺; AA Anal: 1.02 Pro; 0.93 Arg; 1.02 Leu; 2.56 Trp; 0.97 Tyr; 0.46 Ser; 0.74 Phe.

EXAMPLE 66

N-[2-(1-Naphthylmethyl)-4-(morpholineamido)succinyl) ]-Trp-Ser-Tyr-D-Trp-Leu-Arg-proNHEt isomer A (130) and isomer B (131)

Racemic 2-(1-naphthylmethyl)-4-(morpholineamido) succinic acid was synthesized according to the procedure described in Example 14 and coupled to BOC-Trp-(N-indole-formyl)-Ser(OBzl)-Tyr (O-2-Br-Cbz)-D-Trp-(N-indole-formyl)-Leu-Arg(Tos)-Pro-O -Resin using the regular solid phase coupling procedure. The peptide was cleaved from the resin with ethylamine and the protecting groups with HF. The racemic product was separated and purified by HPLC using the conditions previously described to give N-[2-(1-naphthylmethyl)-4 -(morpholineamido)succinyl]-Trp-Ser-Tyr-D-Trp-Leu-Arg -ProNHEt isomer A, $R_T$=47 min; 1.04 Pro; 1.04 Arg; 1.0 Leu; 1.92 Trp; 0.96 Try; 0.42 Ser. And isomer B, $R_T$=49.62 min; Fab Mass spec m/e 1343 (M+H)⁺; AA Anal: 1.03 Pro; 1.04 Arg; 1.01 Leu; 1.97 Trp; 0.96 Tyr; 0.42 Ser.

EXAMPLE 67

N-(2-(1-Naphthylmethyl)-4-ethylamidosuccinyl)-Trp -Ser-Tyr-D-Trp-Leu-Arg-ProNHEt (132)

Using the procedure described in Example 66 and substituting 2-(1-naphthylmethyl)-4-(morpholineamido) succinic acid with 2-(1-naphthylmethyl)-4-(ethylamido) succinic acid, racemic N-(2-(1-naphthylmethyl)-4 -ethylamidosuccinyl)-Trp-Ser-Tyr-DTrp-Leu-Arg-ProNHEt was obtained and purified by HPLC; $R_T$=48.7 min; Fab Mass spec m/e 1300 (M+H)⁺; AA Anal: 1.02 Pro; 1.13 Arg; 1.02 Leu; 1.07 Trp; 0.97 Tyr; 0.54 Ser.

EXAMPLE 68

N-3-(2-Naphthyl)propionyl-Phe-Trp-Ser-Tyr-D-Trp-Leu-Arg -Pro-NHEt (133)

Using the procedure described in Example 41 and substituting with the appropriate acid and amino acids N-3-(2-naphthyl)propionyl-Phe-Trp-Ser-Tyr-D-Trp -Leu-Arg-ProNHEt was synthesized and purified by HPLC, $R_T$=46.74 min; Fab Mass spec m/e 1363 (M+H)⁺; AA Anal: 1.0 Pro; 1.1 Arg: 1.0 Leu; 1.1 Trp; 1.0 Tyr; 0.7 Ser; 1.0 Phe.

EXAMPLE 69

N-Acetyl-D-Phe-Trp-Ser-Tyr-D-Trp-Leu-Arg-ProNHEt (134)

Using the procedure described in Example 46 and substituting with the appropriate amino acids N-acetyl-D-Phe-Trp-Ser-Tyr-DTrp-Leu-Arg-NHEt was synthesized and purified by HPLC, $R_T$=38.5 min., Fab Mass spec m/e 1223 (M+H); AA Anal: 1.0 Pro; 1.2 Arg; 1.1 Leu; 2.2 Trp; 1.0 Tyr; 0.5 Ser; 0.9 Phe.

EXAMPLE 70

N-2-Indolinecarbonyl-Trp-Ser-Tyr-D-Trp-Leu-Arg-Pro-NHEt isomer A (135) and isomer B (136)

Using the procedure described in Example 47 and substituting 5,6-dihydro-5,5-dimethyl-2-oxo-3-phenyl -1-(2H)-pyrazineacetic acid with Boc-D,L-2-indolinecarboxylic acid D,L-N-2-indolinecarbonyl-Trp-Ser-Tyr-D-Trp-Leu-Arg -ProNHEt was synthesized, purified and separated by HPLC to give isomer A, $R_T$=32.8 min; Fab Mass spec m/e 1179 (M+H)⁺; AA Anal: 1.0 Pro; 1.1 Arg; 1.0 Leu; 1.2 Trp; 1.0 Tyr; 0.6 Ser; and isomer B, $R_T$=34.54 min; Mass spec m/e 1179 (M+H)⁺; AA Anal: 1.1 Pro; 1.2 Arg; 1.0 Leu; 1.2 Trp; 1.0 Tyr; 0.6 Ser.

EXAMPLE 71

N-(N-alpha-Morpholinocarbonyl)-1-Nal-Ser-Tyr-D-Trp-Leu -Arg-ProNHEt (137) and N-(N-alpha-morpholinocarbonyl) -2-Nal-Ser-Tyr-D-Trp-Leu-Arg-ProNHEt (138)

Using the procedure described in Example 32, and substituting with the appropriate amino acids in the synthesis N-(N-alpha-morpholinocarbonyl)-1-Nal-Ser-Tyr -D-Trp-Leu-Arg-ProNHEt, $R_T$=40.6 min; Fab Mass spec m/e 1158 (M+H)⁺; AA Anal: 1.0 Pro; 1.07 Arg; 1.02 Leu; 1.13 Trp; 0.96 Tyr; 0.53 Ser; and N-(N-alpha-morpholinocarbonyl)-2-Nal-Ser-Tyr-D-Trp -Leu-Arg-ProNHEt, $R_T$=41.5 min; Fab Mass spec m/e 1158 (M+H)⁺; AA Anal: 0.98 Pro; 1.17 Arg; 1.01 Leu; 0.6 Trp; 0.99 Tyr; 0.47 Ser; were obtained.

EXAMPLE 72

Using the procedures described in Examples 56 and 62 the following compounds are made:

N-3-(4-Fluorophenyl)propionyl-D-4-Cl-phenylalanyl -seryl-tyrosyl-D-tryptyl-leucyl-arginyl-prolylethylamide.

N-3-(4-Fluorophenyl)proiionyl-D-tyrosyl-seryl-tyrosyl-D -tryptyl-leucyl-arginyl-prolylethylamide.

N-3-(4-Fluorophenyl)propionyl-D-5-(indole) -fluorotryptyl-seryl-tyrosyl-D-tryptyl-leucyl-arginyl-prolylethylamide.

N-3-(4-Fluorophenyl)propionyl-5-(indole) -fluorotryptyl-seryl-tyrosyl-D-tryptyl-leucyl-arginyl-prolyl-ethylamide.

N-3-(4-Fluorophenyl)propionyl-D-1-naphthylalanyl -seryl-tyrosyl-D-tryptyl-leucyl-arginyl-prolylethylamide.

N-3-(4-Fluorophenylpropionyl-1-naphthylalanyl -seryl-tyrosyl-D-tryptyl-leucyl-arginyl-prolylethylamide.

N-3-(2,4-Difluorophenyl)propionyl-D-tryptyl-seryl-N -methyl-tyrosyl-D-lysyl(N-epsilon nicotinyl)-leucyl -arginyl-prolylethylamide.

N-3-(3-Fluorophenyl)propionyl-D-tryptyl-seryl-N-methyl -tyrosyl-D-lysyl(N-epsilon-nicotinyl)-leucyl-arginyl -prolylethylamide.

N-3-(4-Chlorophenyl)propionyl-D-tryptyl-seryl-N-methyl -tyrosyl-D-lysyl(N-epsilon-nicotinyl)-leucyl-arginyl -prolylethylamide.

N-3-(4-Fluorophenyl)propionyl-D-3-pyridylalanyl -seryl-N-methyl-tyrosyl-D-lysyl(N-epsilon-nicotinyl)-leucylarginyl prolylethylamide.

N-3-(4-Fluorophenyl)propionyl-D-2-thienylalanyl -seryl-N-methyl-tyrosyl-D-lysyl(N-epsilon-nicotinyl)-leucyl -arginyl-prolylethylamide.

N-3-(4-Fluorophenyl)propionyl-D-2-thienylalanyl -seryl-tyrosyl-D-lysyl-leucyl-arginyl-prolylethylamide.

N-3-(3-Indolyl)propionyl-D-2-indolinecarbonyl -D-tryptyl-seryl-tyrosyl-D-tryptyl-leucyl-arginyl-prolylethylamide.

N-(3-(2-Naphthyl)propionyl)-D-2-indolinecarbonyl -D-tryptyl-seryl-tyrosyl-D-tryptyl-leucyl-arginyl-prolylethylamide.

N-(3-(2-Naphthyl)propionyl)-2-indolinecarbonyl -D-tryptyl-seryl-tyrosyl-D-tryptyl-leucyl-arginyl-prolylethylamide.

EXAMPLE 73

Using the procedure described in Examples 56 and 62 but starting with BOC-D-Ala-NH-Resin (benzhydrylamine resin) and cleaving the peptide from the resin and protecting group with HF/anisole at 0° C. for 1 h. After work up and HPLC purification the following compounds are obtained:

N-3-(4-Fluorophenyl)propionyl-D-tryptyl-seryl-tyrosyl -D-lysyl(N-epsilon-nicotinyl)-leucyl-arginyl-prolyl-D-alanylamide.

N-3-(4-Fluorophenyl)propionyl-D-tryptyl-seryl-tyrosyl -D-tryptyl-leucyl-arginyl-prolyl-D-alanylamide.

N-3-(4-Fluorophenyl)propionyl-D-3-pyridylalanyl -seryl-lysyl(N-epsilon-nicotinyl)-D-lysyl(N-epsilon-nicotinyl) -leucyl-lysyl(N-epsilon-isopropyl)-prolyl-D-alanylamide.

N-3-(4-Fluorophenyl)propionyl-D-2-thienylalanyl -seryl-tyrosyl-D-lysyl-leucyl-arginyl-prolyl-D-alanylamide.

N-3-(4-Fluorophenyl)propionyl-D-2-thienylalanyl -seryl-N-methyl-tyrosyl-D-lysyl(N-epsilon-nicotinyl)-leucyl -arginyl-prolyl-D-alanylamide.

N-3-(4-Fluorophenyl)propionyl-D-tryptyl-seryl-N-methyl -tyrosyl-D-lysyl(N-episolon-nicotinyl)-leucyl-arginylprolyl -D-alanylamide.

EXAMPLE 74

Using the procedure described in Examples 72 and 73 and substituting with the appropriate amino acids and acids the following compounds are synthesized and purified by HPLC:

N-3(2-Naphthyl)propionyl-D-4-Cl-phenylalanyl-D -3-pyridyl-alanyl-seryl-lysyl(N-epsilon nicotinyl)-D-lysyl(N -epsilon-nicotinyl)-leucyl-lysyl(N-epsilon-isopropyl)-prolyl-D -alanylamide.

N-3(4-Chlorophenyl)propionyl-D-4-Cl-phenylalanyl -D-2-thienylalanyl-seryl-tyrosyl-D-lysyl-leucyl-arginyl-prolyl -D-alanylamide.

N-3(4-Fluorophenyl)propionyl-D-4-Cl-phenylalanyl -D-2-thienylalanyl-seryl-tyrosyl-D-lysyl-leucyl-arginyl-prolyl -D-alanylamide.

N-3-(2-Naphthyl)propionyl-D-4-Cl-phenylalanyl -D-3-pyridyl-alanyl-seryl-N-methyl-tyrosyl-d-lysyl(N-epsilon -nicontinoyl)-leucyl-lysyl(N-epsilon-isopropyl)-prolyl-D -alanylamide.

N-3-(2-Naphthyl)propionyl-D-4-Cl-phenylalanyl-D -3-pyridyl-alanyl-N-methyl-seryl-N-methyl-tyrosyl-D-lysyl(N-epsilon -nicotinyl)-leucyl-lysyl(N-epsilon-isopropyl)-prolyl-D -alanylamide.

N-3-(2-Naphthyl)propionyl-D-4-Cl-phenylanalyl -D-3-pyridyl-alanyl-N-methyl-seryl-lysyl-(N-epsilon-nicotinyl)-D -lysyl(N-epsilon-nicotinyl)-leucyl-lysyl(N-epsilon -isopropyl)-prolyl-D-alanylamide.

N-3-(4-Chlorophenyl)propionyl-D-4-Cl-phenylalanyl -D-2-thienylalanyl-seryl-N-methyl-tyrosyl-D-lyssyl-leucyl -arginyl-prolyl-D-alanylamide.

N-3-(4-Chlorophenyl)propionyl-D-4-Cl-phenylalanyl -D-thienylalanyl-N-methyl-seryl-tyrsoyl-D-lysyl-leucyl -arginyl-prolyl-D-alanylamide.

N-3-(4-Chlorophenyl)propionyl-D-4-Cl-phenylalanyl -D-2-thienylalanyl-N-methyl-seryl-N-methyl-tyrosyl-D-lysyl -arginyl-prolyl-D-alanylamide.

EXAMPLE 75

N-(5-Fluoro-2-indolecarbonyl)-D-Trp-Ser-Tyr-D-Trp-Leu -Arg-ProNHEt(139)

The procedure described in Example 35 was used, but substituting 5-fluoro-2-indolecarboxylic acid for 3-(4-imidazolyl)propionic acid and Boc-D-Trp$^3$(N-indoleformyl) for Boc-Trp$^3$(N-indole-formyl). Afer HF treatment, workup, and HPLC purification N-(5-Fluoro-2-indolecarbonyl)-D-Trp-Ser-Tyr-D-Trp-Leu-Arg-ProNHEt was obtained as the trifluoroaCetate salt; $R_T$=47.2 minutes; Fab Mass spec m/e 1195 (M+H)$^+$. Amino Acid Anal: 1.0 Pro; 1.1 Arg; 1.0 Leu; 0.9 Trp; 1.0 Tyr; 0.4 Ser.

EXAMPLE 76

The procedure described in Example 75 is used, but substituting with the appropriate amino acids and carboxylic acids. After HF treatment, workup, and HPLC purification the following compounds were obtained and characterized as the trifluoroacetate salt:

(3-9) [N-(3-(4-Fluorophenyl)propionyl) -D-4-Cl-Phe$^3$-D-Trp$^6$-Pro$^9$NHEt]LHRH (140), $R_T$=49.80 minutes; Fab mass spec m/e 1179 (M+H)$^+$. Amino Acid Anal: 1.0 Pro; 1.0 Arg; 1.0 Leu; 0.7 Trp; 1.0 Tyr; 0.5 Ser.

(3-9)[N-(3-(4-Fluorophenyl)propionyl) -D-Tyr$^3$-D-Trp$^6$-Pro$^9$NHEt]LHRH (141), $R_T$=41.41 minutes; Fab Mass spec m/e 1161 (M+H)$^+$. Amino Acid Anal: 1.1 Pro; 0.9 Arg; 1.0 Leu; 1.0 Trp; 1.9 Tyr; 0.5 Ser.

(3-9)[N-(3-(4-Fluorophenyl)propionyl) -5-F-Trp$^3$-D-Trp$^6$-Pro$^9$NHEt]LHRH (142), $R_T$=46.18 minutes; Fab Mass spec m/e 1202 (M+H)$^+$. Amino Acid Anal: 1.1 Pro; 1.1 Arg; 1.0 Leu; 0.9 Trp; 1.0 Tyr; 0.4 Ser.

(3-9)[N-(3-(4-Fluorophenyl)propionyl)-D -5-F-Trp$^3$-D-Trp$^6$-Pro$^9$NHEt]LHRH (143), $R_T$=47.11 minutes; Fab Mass spec m/e 1202 (M+H)$^+$. Amino Acid Anal: 1.1 Pro; 1.1 Arg; 1.0 Leu; 0.9 Trp; 1.0 Tyr; 0.4 Ser.

(3-9)[N-(3-(4-Fluorophenyl)propionyl) -1-Nal$^3$-D-Trp$^6$-Pro$^9$NHEt]LHRH (144), $R_T$=50.23 minutes; Fab Mass spec m/e 1195 (M+H)$^+$. Amino Acid Anal: 1.0 Pro; 1.2 Arg; 1.1 Leu; 1.0 Trp; 1.0 Tyr; 0.6 Ser.

(3-9)[N-(3-(4-Fluorophenyl)propionyl) -D-1-Nal$^3$-D-Trp$^6$-Pro$^9$NHEt]LHRH (145), $R_T$=50.23 minutes; Fab Mass spec m/e 1195 (M+H)$^+$. Amino Acid Anal: 1.0 Pro; 1.2 Arg: 1.0 Leu; 1.0 Trp; 1.0 Tyr; 0.5 Ser.

(3-9)[N-(3-(4-Fluorophenyl)propionyl) -D-Trp$^{3,6}$-4-OH-Pro$^4$-Pro$^9$NHEt]LHRH (146), R$_T$=46.5 minutes; Fab Mass spec m/e 1210 (M+H)$^+$. Amino Acid Anal: 1.0 Pro; 1.1 Ar9; 1.0 Leu; 2.3 Trp; 1.0 Tyr.

(3-9)[N-(3-(4-Fluorophenyl)propionyl) -D-Pro$^3$-D-Trp$^6$-Pro$^9$NHEt]LHRH (147), R$_T$=41.89 minutes; Fab Mass spec m/e 1095 (M+H)$^+$. Amino Acid Anal: 2.0 Pro; 1.1 Arg; 1.0 Leu; 1.1 Trp; 1.0 Tyr; 0.6 Ser.

(3-9)[N-(3-(4-Fluorophenyl)propionyl) -Pro$^3$-D-Trp$^6$-Pro$^9$NHEt]LHRH (148), R$_T$=40.59 minutes; Fab Mass spec m/e Leu; 0.8 Trp; 1.0 Tyr; 0.6 Ser.

(3-9)[N-(3-(4-Fluorophenyl)propionyl) -D-Trp3-D-4-Cl-Phe$^6$-Pro$^9$NHEt]LHRH (149), R$_T$=50.04 minutes; Fab Mass spec m/e 1179 (M+H)$^+$. Amino Acid Anal: 1.0 Pro; 1.0 Arg; 1.1 Leu; 1.0 Tyr; 0.7 Trp; 0.6 Ser.

(3-9)[N-(3-(4-Fluorophenyl)propionyl) -D-Trp$^3$-D-Tyr$^6$-Pro$^9$NHEt]LHRH (150), R$_T$=41.24 minutes; Fab Mass spec m/e 1161 (M+H)$^+$. Amino Acid Anal: 1.0 Pro; 1.1 Arg; 1.1 Leu; 2.0 Tyr; 0.9 Trp; 0.6 Ser.

(3-9)[N-(3-(3,4-diFluorophenyl)propionyl) -D-Trp$^{3,6}$-Pro$^9$NHEt]LHRH (151), R$_T$=47.51 minutes; Fab Mass spec m/e 1202 (M+H)$^+$. Amino Acid Anal: 1.0 Pro; 1.0 Arg; 1.1 Leu; 1.2 Trp; 1.0 Tyr; 0.6 Ser.

EXAMPLE 77

The procedure described in Example 61 was used, but substituting with the appropriate amino acids and carboxylic acids. After HF treatment, workup, and HPLC purification the following compounds were obtained and characterized as the trifluoroacetate salt:

(3-9)[N-(3-(2,4-diFluorophenyl)propionyl) -D-Trp$^3$-NMeTyr$^5$-D-Lys$^6$(N-epsilon-nicotinyl)-Pro$^9$NHEt]LHRH (152), R$_T$=36.10 minutes; Fab Mass spec m/e 1263 (M+H)$^+$. Amino Acid Anal: 1.0 Pro; 1.1 Arg; 1.0 Leu; 0.9 Lys; 0.9 Trp; 0.5 Ser.

(3-9)[N-(3-(3-Fluorophenyl)propionyl) -D-Trp$^3$-NMeTyr$^5$-D-Lys$^6$(N-epsilon-nicotinyl)-Pro$^9$NHEt]LHRH (153), R$_T$=35.38 minutes; Fab Mass spec m/e 1245 (M+H)$^+$. Amino Acid Anal: 1.1 Pro; 1.1 Arg; 1.0 Leu; 1.0 Lys; 0.9 Trp; 0.5 Ser.

(3-9)[N-(3-(4-Chlorophenyl)propionyl) -D-Trp$^3$-NMeTyr$^5$-DLys$^6$(N-epsilon-nicotinyl)-Pro$^9$NHEt]LHRH (154), R$_T$=35.38 minutes; Fab Mass spec m/e 1261 (M+H)$^+$. Amino Acid Anal: 1.0 Pro; 1.1 Arg; 1.0 Leu; 1.0 Lys; 0.9 Trp; 0.5 Ser.

(3-9)[N-(3-(2,4-diFluorophenyl)propionyl) -D-Trp$^{3,6}$-NMeTyr$^5$-Pro$^9$NHEt]LHRH (155), R$_T$=47.73 minutes; Fab Mass spec m/e 1216 (M+H)$^+$. Amino Acid Anal: 1.0 Pro; 1.0 Arg; 1.0 Leu; 0.7 Trp; 0.5 Ser.

(3-9)[N-(3-(4-Chlorophenyl)propionyl) -D-Trp$^{3,6}$-NMeTyr$^5$-Pro$^9$NHEt]LHRH (156), R$_T$=49.34 minutes; Fab Mass spec m/e 1214 (M+H)$^+$. Amino Acid Anal: 1.0 Pro; 1.0 Arg; 1.0 Leu; 2.0 Trp; 0.5 Ser.

(3-9)[N-(3-(4-Fluorophenyl)propionyl)-D -1-Nal$^3$-NMeTyr$^5$-D-Trp$^6$-Pro$^9$NHEt]LHRH (157), R$_T$=50.88 minutes; Fab Mass spec m/e 1209 (M+H)$^+$. Amino Acid Anal: 1.0 Pro; 1.2 Arg; 1.0 Leu; 1.0 Trp; 0.6 Ser.

(3-9)[N-(3-(4-Fluorophenyl)propionyl) -1-Nal$^3$-NMeTyr$^5$-DTrp$^6$-Pro$^9$NHEt]LHRH (158), R$_T$=51 98 minutes; Fab Mass spec m/e 1209 (M+H)$^+$. Amino Acid Anal: 1.0 Pro; 1.0 Arg; 1.0 Leu; 1.0 Trp; 0.6 Ser.

(3-9)[N-(3-(4-Bromophenyl)propionyl)-D -1-Nal$^3$-NMeTyr$^5$-DTrp$^6$-Pro$^9$NHEt]LHRH (159), R$_T$=54.23 minutes; Fab Mass spec m/e 1271 (M+H)$^+$. Amino Acid Anal: 1.0 Pro; 1.0 Arg; 1.0 Leu; 0.9 Trp; 0.6 Ser.

(3-9)[N-(3-(4-Bromophenyl)propionyl) -1-Nal$^3$-NMeTyr$^5$-DTrp$^6$-Pro$^9$NHEt]LHRH (160), R$_T$=56.23 minutes; Fab Mass spec m/e 1271 (M+H)$^+$. Amino Acid Anal: 1 0 Pro; 1.0 Arg; 1.0 Leu; 1.2 Trp; 0.5 Ser.

EXAMPLE 78

N-[3-(4-Fluorophenyl)propionyl]-D-Thia-Ser-NMeTyr-D-Lys(N-epsilon-nicotinyl)-Leu-Arg-Pro-D-AlaNH$_2$ (161)

The synthetic protocol described in Example 1 was slightly modified as follows: Boc-D-Ala-NH-Resin (benzhydrylamine resin) was substituted for Boc-Pro-P-Resin to be coupled to Boc-Pro using two coupling-1 hr, Boc-D-Lys(N-epsilon-FMOC) was substituted for Boc-D-Leu, Boc-N-Me-Tyr(O-2,6-diCl-Bzl) was substituted for Boc-Tyr(O-2-Br-Cbz), 0.1% DMAP was added to the solution of Boc-Ser(O-Bzl) and two couplings of 2 hour each were used for Boc-D-Thia and 3-(4-fluorophenyl)propionic acid. Upon completion of the synthesis the resin was treated with 30% piperidine solution in DMF overnight to remove the FMOC group. After washing (3×) with methylene chloride and drying the resin was coupled with nicotinic acid using two couplings of 1 hour each. The resin was dried over P$_2$O$_5$ overnight and then treated with HF/anisole at 0° C. for 1 hour. After workup and HPLC purification, using the same conditions previously described, N-[3-(4-Fluorophenyl)propionyl]-D-Thia-Ser-NMeTyr-D-Lys(N-epsilon-nicotinyl)-Leu-Arg-Pro-D-AlaNH$_2$ was obtained as the trifluoracetate salt; R$_T$=33.65 minutes; Fab Mass spec m/e 1255(M+H)$^+$. Amino Acid Anal: 0.9 Ala; 1.1 Pro; 1.0 Arg; 1.0 Leu; 0.9 Lys; 0.4 Ser.

EXAMPLE 79

The procedure described in Example 75 is used, but substituting with the appropriate amino acids and carboxylic acids. After HF treatment, workup, and HPLC purification the following compounds were obtained and characterized as the trifluoroacetate salts:

(3-10)[N-(3-(4-Fluorophenyl)propionyl)-D-Trp$^{3,6}$-D-Ala$^{10}$]LHRH (162), R$_T$=44.23 minutes; Fab Mass spec m/e 1228 (M+H)$^+$. Amino Acid Anal: 1.0 Ala; 1.0 Pro; 1.0 Arg; 1.0 Leu; 1.4 Trp; 1.0 Tyr; 0.4 Ser.

(3-10)[N-(3-(4-Fluorophenyl)propionyl)-D-Trp$^3$-NMeTyr$^5$-D-Lys$^6$(N-epsilon-nicotinyl)-D-Ala$^{10}$]LHRH (163), R$_T$=33.65 minutes; Fab Mass spec m/e 1228 (M+H)$^+$. Amino Acid Anal: 1.0 Ala; 1.0 Pro; 1.0 Arg; 1.0 Leu; 1.0 Lys; 0.8 Trp; 0.4 Ser.

(3-10)[N-(3-(4-Fluorophenyl)propionyl)-D-Trp$^{3,6}$-NMeTyr$^5$-D-Ala$^{10}$]LHRH (164), R$_T$=44.93 minutes; Fab Mass spec m/e 1241 (M+H)$^+$. Amino Acid Anal: 1.0 Ala; 1.0 Pro; 1.0 Arg; 1.0 Leu; 1.7 Trp; 0.4 Ser.

(3-10)[N-(3-(4-Fluorophenyl)propionyl)-D-Thia$^3$-D-Lys$^6$-D-Ala$^{10}$]LHRH (165), R$_T$=34.38 minutes; Fab Mass spec m/e 1152 (M+H)$^+$. Amino Acid Anal: 1.0 Ala; 1.0 Pro; 1.0 Arg; 1.0 Leu; 1.0 Lys; 1.0 Tyr; 0.7 Ser.

(3-10)[N-(3-(4-Fluorophenyl)propionyl)-D-Thia³-NMeTyr⁵-D-Lys⁶-D-Ala ]LHRH (166), $R_T$=34.10 minutes; Fab Mass spec m/e 1166 (M+H)⁺. Amino Acid Anal: 1.0 Ala; 1.0 Pro; 1.0 Arg; 1.0 Leu; 1.0 Lys; 0.6 Ser.

(3-10)[N-(3-(4-Chlorophenyl)propionyl)-D-Thia³-Ser-(O-Bzl)⁴-D-Lys⁶-D-Ala¹⁰]LHRH (167), $R_T$=43.46 minutes; Fab Mass spec m/e 1242 (M+H)⁺. Amino Acid Anal: 1.0 Ala; 1.1 Pro; 1.1 Arg; 1.0 Leu; 1.1 Lys; 0.9 Tyr; 0.6 Ser.

(3-10)[N-(3-(4-Chlorophenyl)propionyl)-D-Thia³-Ser-(O-Bzl)⁴-NMeTyr⁵-D-Lys⁶-D-Ala¹⁰]LHRH (168), $R_T$=43.13 minutes; Fab Mass spec m/e 1256 (M+H)⁺. Amino Acid Anal: 0.9 Ala; 1.0 Pro; 1.0 Arg; 1.0 Leu; 1.0 Lys; 0.6 Ser.

(3-10)[N-(3-(4-Fluorophenyl)propionyl)-D-1-Nal³-NMeTyr⁵-D-Lys⁶-D-Ala¹⁰]LHRH (169), $R_T$=36.85 minutes; Fab Mass spec m/e 1194 (M+H)⁺. Amino Acid Anal: 1.0 Ala; 1.0 Pro; 1.0 Arg; 1.0 Leu; 1.0 Lys; 0.6 Ser.

(3-10)[N-(3-(4-Fluorophenyl)propionyl)-D-3-Pal³-NMeTyr⁵-D-Lys⁶-D-Ala¹⁰]LHRH (170), $R_T$=21.48 minutes; Fab Mass spec m/e 1145 (M+H)⁺. Amino Acid Anal: 1.0 Ala; 1.0 Pro; 1.0 Arg; 1.0 Leu; 1.0 Lys; 0.7 Ser.

(3-10)[N-(3-(4-Fluorophenyl)propionyl-D-3-Pal³-NMeTyr⁵-D-Lys⁶(N-epsilon-nicotinyl)-D-Ala¹⁰]LHRH (171), $R_T$=23.59 minutes; Fab Mass spec m/e 1250 (M+H)⁺. Amino Acid Anal: 1.0 Ala; 1.0 Pro; 1.0 Arg; 1 0 Leu; 1.0 Lys; 0.6 Ser.

(3-10)[N-(3-(4-Chlorophenyl)propionyl)-D-3-Pal³-Lys⁵(N-epsilon-nicotinyl)-D-Lys⁶(N-epsilon-nicotinyl)-D-Ala¹⁰]LHRH (172), $R_T$=22.44 minutes; Fab Mass spec m/e 1336 (M+H)⁺. Amino Acid Anal: 1.0 Ala; 1.0 Pro; 1.0 Arg; 1 0 Leu; 2.0 Lys; 0.6 Ser.

(3-10)[N-(3-(4-Fluorophenyl)propionyl)-D-Trp³-NMeTyr⁵-D-Lys⁶-D-Ala¹⁰]LHRH (173), $R_T$=32.48 minutes; Fab Mass spec m/e 1183 (M+H)⁺. Amino Acid Anal: 1.0 Ala; 1.0 Pro; 1.0 Arg; 1.0 Leu; 1.0 Lys; 1.0 Trp; 0.5 Ser.

(3-10)[N-(3-(4-Fluorophenyl)propionyl)-D-1-Nal³-NMeTyr⁵-D-Lys⁶(N-epsilon-nicotinyl)-D-Ala¹⁰]LHRH (174), $R_T$=38.18 minutes; Fab Mass spec m/e 1299 (M+H)⁺. Amino Acid Anal: 1.0 Ala; 1.0 Pro; 1 0 Arg; 1.0 Leu; 1.0 Lys; 0.5 Ser.

(3-10)[N-(3-(4-Fluorophenyl)propionyl)-D-4-Cl-Phe³-NMeTyr⁵-D-Lys⁶-D-Ala¹⁰]LHRH (175), $R_T$=35.82 minutes; Fab Mass spec m/e 1178 (M+H)⁺. Amino Acid Anal: 1.0 Ala; 1.0 Pro; 1.0 Arg; 1.0 Leu; 1.0 Lys; 0.5 Ser.

(3-10)[N-(3-(4-Fluorophenyl)propionyl)-D-1-Nal³-hhPhe⁴-NMeTyr⁵-D-Lys⁶-D-Ala¹⁰]LHRH (176), $R_T$=45.58 minutes; Fab Mass spec m/e 1282 (M+H)⁺. Amino Acid Anal: 1.0 Ala; 1.0 Pro; 1.0 Arg; 1.0 Leu; 1.0 Lys.

(3-10)[N-(3-(4-Fluorophenyl)propionyl)-D-3-Bal³-NMeTyr⁵-D-Lys⁶-D-Ala¹⁰]LHRH (177), $R_T$=36.8 minutes; Fab Mass spec m/e 1200 (M+H)⁺. Amino Acid Anal: 1.0 Ala; 1.0 Pro; 1.0 Arg; 1.0 Leu; 1.1 Lys; 0.8 Ser.

(3-10)[N-(3-(4-Fluorophenyl)propionyl)-D-1-Nal³-NMeTyr⁵-D-Hcit⁶-D-Ala¹⁰]LHRH (178), $R_T$=40.28 minutes; Fab Mass spec m/e 1237 (M+H)⁺. Amino Acid Anal: 1.0 Ala; 1.0 Pro; 1.0 Arg; 1.0 Leu; 1.0 Hcit; 0.7 Ser.

(3-10)[N-(3-(4-Fluorophenyl)propionyl)-D-1-Nal³-NMeTyr⁵-D-Lys⁶-D-Ala¹⁰]LHRH (179), $R_T$=36.68 minutes; Fab Mass spec m/e 1194 (M+H)⁺. Amino Acid Anal: 1.0 Ala; 1.0 Pro; 1.0 Arg; 1.0 Leu; 1.0 Lys; 0.6 Ser.

(3-10)[N-(3-(4-Fluorophenyl)propionyl)-1-Nal³-NMeTyr⁵-D-Ser⁶-D-Ala¹⁰]LHRH (180), $R_T$=40.98 minutes; Fab Mass spec m/e 1153 (M+H)⁻. Amino Acid Anal: 1.0 Ala; 1.0 pro; 1.0 Arg; 1.0 Leu; 1.2 Ser.

(3-10)[N-(3-(4-Fluorophenyl)propionyl)-D-1-Nal³-NMeTyr⁵-D-Ser⁶-D-Ala¹⁰]LHRH (181), $R_T$=41.15 minutes; Fab Mass spec m/e 1153 (M+H)⁺. Amino Acid Anal: 1.0 Ala; 1.1 Pro; 1.0 Arg; 1.0 Leu; 1.1 Ser.

(3-10)[N-(3-(4-Fluorophenyl)propionyl)-D-Trp³-NMeTyr⁵-D-Lys⁶-D-Ala¹⁰]LHRH (182), $R_T$=36.5 minutes; Fab Mass spec m/e 1215 (M+H)⁺. Amino Acid Anal: 1.0 Ala; 1.1 Pro; 1.0 Arg; 1.0 Leu; 1.0 Lys; 0.6 Ser.

(3-10)[N-(3-(4-Fluorophenyl)propionyl)-D-Thiaz³-NMeTyr⁵-D-Lys⁶-D-Ala¹⁰]LHRH (183), $R_T$=27.26 minutes; Fab Mass spec m/e 1151 (M+H)⁺. Amino Acid Anal: 1.0 Ala; 1.1 Pro; 1.0 Arg; 1.1 Leu; 1.0 Lys; 1.0 Thiaz; 0.6 Ser.

(3-10)[N-(3-(4-Fluorophenyl)propionyl)-D-1-Nal³-NMeTyr⁵-D-3-Pal⁶-D-Ala¹⁰]LHRH (184), $R_T$=37.9 minutes; Fab Mass spec m/e 1214 (M+H)⁻. Amino Acid Anal: 1.0 Ala; 1.1 Pro; 1.0 Arg; 1.0 Leu; 0.6 Ser.

(3-10)[N-(3-(4-Fluorophenyl)propionyl)-D-1-Nal³-NMeTyr⁵-D-Lys⁶-Cha⁷-D-Ala¹⁰]LHRH (185), $R_T$=38.46 minutes; Fab Mass spec m/e 1234 (M+H)⁺. Amino Acid Anal: 1.0 Ala; 1.1 Pro; 1.0 Arg; 0.9 Cha; 1.0 Lys; 0.5 Ser.

(3-10)[N-(3-(4-Fluorophenyl)propionyl)-D-2-Nal³-NMeTyr⁵-D-Lys⁶-D-Ala¹⁰]LHRH (186), $R_T$=36.18 minutes; Fab Mass spec m/e 1194 (M+H)⁺. Amino Acid Anal: 1.0 Ala; 1.1 Pro; 1.0 Arg; 1.0 Leu; 1.0 Lys; 0.5 Ser.

(3-10)[N-(3-(4-Fluorophenyl)propionyl)-D-2-Nal³-NMeTyr⁵-D-Lys⁶(N-epsilon-nicotinyl)-D-Ala¹⁰]LHRH (187), $R_T$=37.00 minutes; Fab Mass spec m/e 1299 (M+H)⁺. Amino Acid Anal: 1.0 Ala; 1.1 Pro; 1.0 Arg; 1.0 Leu; 1.0 Lys; 0.5 Ser.

(3-10)[N-(3-(4-Fluorophenyl)propionyl)-D-1-Nal³-Tyr⁵(OMe)-D-Lys⁶-D-Ala¹⁰]LHRH (188), $R_T$=39.75 minutes; Fab Mass spec m/e 1194 (M+H)⁺. Amino Acid Anal: 1.0 Ala; 1.2 Pro; 1.0 Arg; 1.1 Leu; 1.0 Lys; 1.0 Tyr; 0.5 Ser.

(3-10)[N-(3-(4-Fluorophenyl)propionyl)-D-1-Nal³-NMePhe⁵-D-Lys⁶-D-Ala¹⁰]LHRH (189), $R_T$=40.20 minutes; Fab Mass spec m/e 1178 (M+H)⁺. Amino Acid Anal: 1.0 Ala; 1.1 Pro; 1.0 Arg; 1.1 Leu; 1.0 Lys; 1.1 NMePhe; 0.5 Ser.

(3-10)[N-(3-(4-Fluorophenyl)propionyl)-D-1-Nal³-NMeTyr⁵-D-Lys⁶-NMeLeu⁷-D-Ala¹⁰]LHRH (190), $R_T$=37.98 minutes; Fab Mass spec m/e 1208 (M+H)⁺. Amino Acid Anal: 1.0 Ala; 1.0 Pro; 1.0 Arg; 1.0 Lys; 0.5 Ser.

(3-10)[N-(3-(4-Fluorophenyl)propionyl)-D-1-Nal³-Lys⁵(N-epsilon-nicotinyl)-D-Lys⁶(N-epsilon-nicotinyl)-D-Ala¹⁰]LHRH (191), $R_T$=34.83 minutes; Fab Mass spec m/e 1355 (M+H)⁺. Amino Acid Anal: 1.0 Ala; 1.1 Pro; 1.0 Arg; 1.1 Leu; 1.9 Lys; 0.6 Ser.

(3-10)[N-(3-(4-Fluorophenyl)propionyl)-D-1-Nal³-NMeTyr⁵-D-Orn⁶-D-Ala¹⁰]LHRH (192), $R_T$=37.38 minutes; Fab Mass spec m/e 1180 (M+H)⁺. Amino Acid Anal: 1.0 Ala; 1.1 Pro; 1.0 Arg; 1.0 Leu; 1.1 Orn; 1.1 NMeTyr; 0.6 Ser.

EXAMPLE 80

The synthetic protocol described in Example 79 was used, but substituting Boc-Lys(N,N-epsilon-isopropyl,Cbz) for Boc-Arg(Tos) and substituting with the appropriate amino acids and carboxylic acids. After HF treatment, workup, and HPLC purification the following compounds were obtained and characterized as the trifluoroacetate salts:

(3-10)[N-(3-(4-Fluorophenyl)propionyl)-D-3-Pal$^3$-Lys$^5$(N-epsilon-nicotinyl)-D-Lys$^6$(N-epsilon-nicotinyl)-Lys$^8$(N-epsilon-isopropyl)-D-Ala$^{10}$]LHRH (193), $R_T$=20.88 minutes; Fab Mass spec m/e 1320 (M+H)$^+$. Amino Acid Anal: 1.0 Ala; 1.0 Pro; 1.0 Leu; 1.0 Lys; 0.5 Ser.

(3-10)[N-(3-(4-Chlorophenyl)propionyl)-D-3-Pal$^3$-NMeTyr$^5$-D-Lys$^6$(N-epsilon-nicotinyl)-Lys$^8$(N-epsilon-isopropyl)-D-Ala$^{10}$]LHRH (194), $R_T$=26.40 minutes; Fab Mass spec m/e 1280 (M+H)$^+$. Amino Acid Anal: 1.0 Ala; 1.0 Pro; 1.0 Leu; 1.0 Lys; 0.5 Ser.

(3-10)[N-(3-(4-Fluorophenyl)propionyl)-D-Trp$^3$-NMeTyr$^5$-D-Lys$^6$(N-epsilon-nicotinyl)-Lys$^8$(N-epsilon-isopropyl)-D-Ala$^{10}$]LHRH (195), $R_T$=34.68 minutes; Fab Mass spec m/e 1302 (M+H)$^+$. Amino Acid Anal: 1.0 Ala; 1.0 Pro; 1.0 Leu; 1.0 Lys; 0.4 Ser; 0.3 Trp.

(3-10)[N-(3-(4-Fluorophenyl)propionyl)-D-Trp$^3$-NMeTyr$^5$-D-Tyr$^6$-Lys$^8$(N-epsilon-isopropyl)-D-Ala$^{10}$]LHRH (196), $R_T$=40.88 minutes; Fab Mass spec m/e 1232 (M+H)$^+$. Amino Acid Anal: 1.0 Ala; 1.0 Pro; 1.0 Leu; 1.0 Tyr; 0.5 Ser; 1.0 Trp.

(3-10)[N-(3-(4-Fluorophenyl)propionyl)-D-1-Nal$^3$-NMeTyr$^5$-D-Lys$^6$(N-epsilon-nicotinyl)-Lys$^8$(N-epsilon-isopropyl)-D-Ala$^{10}$]LHRH (197), $R_T$=38.97 minutes; Fab Mass spec m/e 1313 (M+H)$^+$. Amino Acid Anal: 1.0 Ala; 1.0 Pro; 1.0 Leu; 1.0 Lys; 0.7 Ser.

(3-10)[N-(3-(4-Fluorophenyl)propionyl)-D-3-Bal$^3$-NMeTyr$^5$-D-Lys$^6$(N-epsilon-isopropyl)-D-Ala$^{10}$]LHRH (198), $R_T$=38.16 minutes; Fab Mass spec m/e 1242 (M+H)$^+$. Amino Acid Anal: 1.0 Ala; 1.0 Pro; 1.0 Arg; 1.0 Leu; 0.6 Ser.

(3-10)[N-(3-(4-Fluorophenyl)propionyl)-D-1-Nal$^3$-NMeTyr$^5$-D-Lys$^6$-Lys$^8$(N-epsilon-isopropyl)-D-Ala$^{10}$]LHRH (199), $R_T$=35.78 minutes; Fab Mass spec m/e 1208 (M+H)$^+$. Amino Acid Anal: 1.0 Ala; 1.1 pro; 1.0 Leu; 1.0 Lys; 0.5 Ser.

(3-10)[N-(3-(4-Fluorophenyl)propionyl)-D-1-Nal$^3$-Tyr$^5$(OMe)-D-Lys$^6$(N-epsilon-nicotinyl)-Lys$^8$(N-epsilon-isopropyl)-D-Ala$^{10}$]LHRH (200), $R_T$=42.58 minutes; Fab Mass spec m/e 1313 (M+H)$^+$. Amino Acid Anal: 1.0 Ala; 1.2 Pro; 1.1 Leu; 1.0 Lys; 1.0 Tyr; 0.5 Ser.

(3-10)[N-(3-(4-Fluorophenyl)propionyl)-D-1-Nal$^3$-D-3Pal$^6$-Lys$^8$(N-epsilon-isopropyl)-D-Ala$^{10}$]LHRH (201), $R_T$=38.92 minutes; Fab Mass spec m/e 1214 (M+H)$^+$. Amino Acid Anal: 1.0 Ala; 1.0 Pro; 1.0 Leu; 0.9 Tyr; 0.6 Ser.

(3-10)[N-(3-(4-Fluorophenyl)propionyl)-D-1-Nal$^3$-Ser$^4$-(O-Bzl)-D-3-Pal$^6$-Lys$^8$(N-epsilon-isopropyl)-D-Ala$^{10}$]LHRH (202), $R_T$=41.83 minutes; Fab Mass spec m/e 1304 (M+H)$^+$. Amino Acid Anal: 1.0 Ala; 1.0 Pro; 1.0 Leu; 0.9 Tyr; 0.6 Ser.

(3-10)[N-(3-(4-Fluorophenyl)propionyl)-D-1-Nal$^3$-Tyr$^5$(OMe)-D-Lys$^6$(N-epsilon-2-carbonylpyrazinyl)-Lys$^8$(N-epsilon-isopropyl)-D-Ala$^{10}$]LHRH (203), $R_T$=48.10 minutes; Fab Mass spec m/e 1314 (M+H)$^+$. Amino Acid Anal: 1.0 Ala; 1.2 Pro; 1.1 Leu; 1.0 Lys; 1.1 Tyr; 0.5 Ser.

(3-10)[N-(3-(4-Fluorophenyl)propionyl)-D-1-Nal$^3$-NMeTyr$^5$-D-Thiaz6-Lys$^8$(N-epsilon-isopropyl)-D-Ala$^{10}$]LHRH (204), $R_T$=52.43 minutes; Fab Mass spec m/e 1234 (M+H)$^+$. Amino Acid Anal: 1.0 Ala; 1.0 Pro; 1.0 Leu; 0.5 Ser.

(3-10)[N-(3-(4-Fluorophenyl)propionyl)-D-1-Nal$^3$-NMePhe$^5$-D-Lys$^6$(N-epsilon-nicotinyl)-D-Ala$^{10}$]LHRH (205), $R_T$=42.22 minutes; Fab Mass spec m/e 1297 (M+H)$^+$. Amino Acid Anal: 0.9 Ala; 1.0 Pro; 1.0 Leu; 1.0 Lys; 0.9 NMePhe; 0.5 Ser.

(3-10)[N-(3-(4-Fluorophenyl)propionyl)-D-1-Nal$^3$-D-Lys$^6$(N-epsilon-4-methoxybenzoyl)-Lys$^8$(N-epsilon-isopropyl)-D-Ala$^{10}$]LHRH (206), $R_T$=49.18 minutes; Fab Mass spec m/e 1343 (M+H)$^+$. Amino Acid Anal: 1.1 Ala; 1.1 Pro; 1.1 Leu; 0.9 Lys; 1.0 NMeTyr; 0.5 Ser.

(3-10)[N-(3-(4-Fluorophenyl)propionyl)-D-1-Nal$^3$-NMeTyr$^5$-D-Lys$^6$(N-epsilon-2-pyrazinyecarbonyl)-Lys$^8$(N-epsilon-isopropyl)-D-Ala$^{10}$]LHRH (207), $R_T$=43.23 minutes; Fab Mass spec m/e 1314 (M+H)$^+$. Amino Acid Anal: 1.0 Ala; 1.0 Pro; 1.0 Leu; 1.0 Lys; 0.8 NMeTyr; 0.5 Ser.

(3-10)[N-(3-(4-Fluorophenyl)propionyl)-D-1-Nal$^3$-NMeTyr$^5$-D-3-Pal$^6$-Lys$^8$(N-epsilon-isopropyl)-D-Ala$^{10}$]LHRH (208), $R_T$=39.13 minutes; Fab Mass spec m/e 1228 (M+H)$^+$. Amino Acid Anal: 1.0 Ala; 1.0 Pro; 1.0 Leu; 1.0 NMeTyr; 0.5 Ser.

EXAMPLE 81

N-(3-(4-Fluorophenyl)propionyl)-D-1-Nal-Ser-NMeTyr-D-Lys(N-epsilon-nicotinyl)-Leu-Lys(N-epsilon-isopropyl)-Pro-NHEt (209)

The procedure described in Example 77 was used, but substituting Boc-Lys(N,N-epsilon-isopropyl,Cbz) for Boc-Arg(Tos). After HF treatment, workup, and HPLC purification N-(3-(4-Fluorophenyl)propionyl)-D-1-Nal-Ser-NMeTyr-D-Lys(N-epsilon-nicotinyl)-Leu-Lys(N-epsilon-isopropyl)-Pro-NHEt was obtained as the trifluoroacetate salt; $R_T$=41.55 minutes; Fab Mass spec m/e 1270 (M+H)$^+$. Amino Acid Anal: 1.0 Pro; 1.0 Leu; 1.0 Lys; 1.0 NMeTyr; 0.5 Ser.

EXAMPLE 82

N-(3-(4-Fluorophenyl)propionyl)-D-1-Nal-Ser-NMeTyr-D-Lys(N-epsilon-morpholinecarbonyl)-Leu-Arg-Pro-D-AlaNH$_2$(210)

The procedure described in Example 80 was used to prepare N-(3-(4-Fluorophenyl)propionyl)-D-1-Nal-Ser-(O-Bzl)-NMeTyr(O-2,6-diCl-Bzl)-D-Lys(N-epsilon-FMOC)-Leu-Arg(Tos)-Pro-D-AlaNH-Resin. The resin was treated with 30% piperidine in DMF overnight to remove the FMOC group. After washing and drying the resin was treated with 0.3M solution of carbonyldiimidazole in DMF (18 mL) for 7 minutes. After washing (3×) with methylene chloride the resin was treated overnight with a solution of 0.3M morpholine in DMF. After washing (3×) with methylene chloride and drying over P$_2$O$_5$ overnight, the resin was treated with HF/anisole at 0° C. for 1 hour. After workup and purification with HPLC using the same conditions previously described, N-(3-(4-Fluorophenyl)propionyl)-D-1-Nal-Ser-NMeTyr-D-Lys(N-epsilon-morpholinecarbonyl)-Leu-Arg-Pro-D-AlaNH$_2$ was obtained as the trifluoroacetate salt; $R_T$=42.7 minutes; Fab Mass spec m/e 1307 (M+H)$^+$. Amino Acid Anal: 1.0 Ala; 1.0 Pro; 1.0 Arg; 1.1 Leu; 0.9 Lys; 0.5 Ser.

EXAMPLE 83

N-(3-(4-Fluorophenyl)propionyl)-D-1-Nal-Ser-NMeTyr-D-Lys(N-epsilon-N'-N"-methyl-piperazinecarbonyl)-Leu-Arg-Pro-D-AlaNH$_2$(211)

The procedure described in Example 82 was used, but substituting N-methyl-piperazine for morpholine. After HF treatment, workup, and HPLC purification N-(3-(4-Fluorophenyl)propionyl)-D-1-Nal-Ser-NMeTyr-D-Lys(N-epsilon-N'-N"-methyl-piperazinecarbonyl)-Leu-Arg-Pro-D-AlaNH$_2$ was obtained as the trifluoroacetate salt; $R_T = 37.30$ minutes; Fab Mass spec m/e 1320 (M+H)$^+$. Amino Acid Anal: 1.0 Ala; 1.0 Pro; 1.0 Arg; 1.0 Leu; 1.0 Lys; 0.5 Ser.

EXAMPLE 84

N-(3-(4-Fluorophenyl)propionyl)-D-1-Nal-Ser-Lys(N-epsilon-hydrazinecarbonyl)-D-Lys(N-epsilon-nicotinyl)-Leu-Arg-Pro-D-AlaNH$_2$(212)

The procedure described in Example 80 was used to prepare N-(3-(4-Fluorophenyl)propionyl)-D-1-Nal-Ser-(O-Bzl)-Lys(N-epsilon-FMOC)-D-Lys(N-epsilon-nicotinyl)-Leu-Arg-Pro-D-AlaNH-Resin. This resin was treated with 30% piperidine in DMF overnight to remove the FMOC group. After washing (3×) with methylene chloride the resin was treated overnight with anhydrous hydrazine (1.5 mL) in (1:1) DMF/methylene chloride (18 mL). After washing (3×) with methylene chloride and drying over P$_2$O$_5$ overnight the resin was treated with HF/anisole at 0° C. for 1 hour. After workup and HPLC purification, using the same conditions previously described, N-(3-(4-Fluorophenyl)propionyl)-D-1-Nal-Ser-Lys(N-epsilon-hydrazinecarbonyl)-D-Lys(N-epsilon-nicotinyl)-Leu-Arg-Pro-D-AlaNH$_2$ was obtained as the trifluoroacetate salt; $R_T = 34.10$ minutes; Fab Mass spec m/e 1308 (M+H)$^+$. Amino Acid Anal: 1.0 Ala; 1.1 Pro; 1.0 Arg; 1.0 Leu; 2.1 Lys; 0.6 Ser.

EXAMPLE 85

N-(3-(4-Fluorophenyl)propionyl)-D-1-Nal-Ser-NMeTyr-D-Lys(N-epsilon-morpholnecarbonyl)-Leu-Lys(N-epsilon-isopropyl)-Pro-D-AlaNH$_2$(213)

The procedure described in Example 82 was used, but substituting Boc-Lys(N,N-epsilon-isopropyl,Cbz) for Boc-Arg(Tos). After HF treatment, workup, and HPLC purification N-(3-(4-Fluorophenyl)propionyl)-D-1-Nal-Ser-NMeTyr-D-Lys(N-epsilon-morpholinecarbonyl)-Leu-Lys(N-epsilon-isopropyl)-Pro-D-AlaNH$_2$ was obtained as the trifluoroacetate salt; $R_T = 43.65$ minutes; Fab Mass spec m/e 1321 (M+H)$^+$. Amino Acid Anal: 1.0 Ala; 1.0 Pro; 1.1 Leu; 1.0 Lys; 1.1 NMeTyr; 0.6 Ser.

EXAMPLE 86

N-alpha-(3-Chloro-4-Fluorobenzoyl)-Lys(N-epsilon-acetyl)-D-1-Nal-Ser-NMeTyr-D-Lys-Leu-Arg-Pro-D-AlaNH$_2$(214)

The procedure described in Example 80 was used to Prepare N-(3-Chloro-4-Fluorobenzoyl)-Lys(N-epsilon-FMOC)-D-1-Nal-Ser(O-Bzl)-NMeTyr(O-2,6-diCl-Bzl)-D-Lys(N-epsilon-Cbz)-Leu-Arg(Tos)-Pro-D-AlaNH-Resin. The resin was treated with 30% piperidine/DMF solution overnight to remove the FMOC group. After washing (3×) with methylene chloride, the resin was acetylated using 0.3M acetylimidazole in DMF for 2 hours. After washing (3×) with methylene chloride and drying over P$_2$O$_5$ overnight, the resin was treated with HF/anisole at 0° C. for 1 hour. After workup and HPLC purification, using the conditions previously described, N-alpha-(3-Chloro-4-Fluorobenzoyl)-Lys(N-epsilon-acetyl)-D-1-Nal-Ser-NMeTyr-D-Lys-Leu-Arg-Pro-D-AlaNH$_2$ was obtained as the trifluoroacetate salt; $R_T = 34.33$ minutes; Fab Mass spec m/e 1370 (M+H)$^+$. Amino Acid Analysis: 1.0 Ala; 1.0 Pro; 1.0 Arg; 1.0 Leu; 1.9 Lys; 0.4 Ser.

EXAMPLE 87

N-alpha-(4-Fluorobenzoyl)-Orn(N-delta-acetyl)-D-1-Nal-Ser-NMeTyr-D-Thiaz-Leu-Lys(N-epsilon-isopropyl)-Pro-D-AlaNH$_2$(215)

The procedure described in Example 86 was used, but substituting 4-fluorobenzoic acid for 3-chloro-4-fluorobenzoic acid, Boc-Orn(N-delta-acetyl) for the Boc-Lys(N-epsilon-FMOC), Boc-D-Thiaz for Boc-D-Lys(N-epsilon-Cbz), and Boc-Lys(N,N-epsilon-isopropyl,Cbz) for Boc-Arg(Tos). The FMOC cleavage procedure is eliminated in this case. After HF treatment, workup, and HPLC purification, using the conditions previously described, N-alpha-(4-Fluorobenzoyl)-Orn(N-delta-acetyl)-D-1-Nal-Ser-NMeTyr-D-Thiaz-Leu-Lys(N-epsilon-isopropyl)-Pro-D-AlaNH$_2$ can be obtained as the trifluoroacetate salt; $R_T = 38.23$ minutes; Fab Mass spec m/e 1362 (M+H)$^+$. Amino Acid Anal: 1.0 Ala; 1.1 Pro; 1.0 Leu; 0.5 Ser; 1.0 Orn.

EXAMPLE 88

N-alpha-(4-Fluorobenzoyl)-Orn(N-delta-acetyl)-D-1-Nal-Ser-Tyr-D-Lys-Leu-Arg-Pro-D-AlaNH$_2$(216)

The same procedure described in Example 87 was used, but substituting Boc-Tyr(O-2-Br-Cbz) for Boc-NMeTyr(O-2,6-diCl-Bzl), Boc-D-Lys(N-epsilon-Cbz) for Boc-D-Thiaz, and Boc-Arg(Tos) for Boc-Lys(N,N-epsilon-isopropyl,Cbz). After HF treatment, workup, and HPLC purification N-alpha-(4-Fluorobenzoyl)-Orn(N-delta-acetyl-D-1-Nal-Ser-Tyr-D-Lys-Leu-Arg-Pro-D-AlaNH$_2$ was obtained as trifluoroacetate salt; $R_T = 30.95$ minutes; Fab Mass spec m/e 1308 (M+H)$^+$. Amino Acid Anal: 1.0 Ala; 1.1 Pro; 1.0 Arg; 1.0 Leu; 1.0 Lys; 1.0 Tyr; 0.6 Ser; 1.1 Orn.

EXAMPLE 89

N-alpha-(4-Fluorobenzoyl)-Orn(N-delta-acetyl)-D-1-Nal-Ser-Tyr-D-Lys(N-epsilon-nicotinyl)-Leu-Arg-Pro-D-AlaNH$_2$(217)

The procedure described in Example 88 was used, but susbtituting Boc-D-Lys(N-epsilon-FMOC) for Boc-D-Lys(n-epsilon-Cbz) to give the N-(4-Fluorobenzoyl)-Orn(N-delta-acetyl)-D-1-Nal-Ser(O-Bzl)-Tyr(O-2,6-diCl-Bzl)-D-Lys(N-epsilon-FMOC)-Leu-Arg(Tos)-Pro-D-AlaNH-Resin. The resin was treated with 30% piperidine/DMF solution overnight to remove the FMOC group. After washing (3×) with methylene chloride, the resin was coupled with nicotinic acid for 2 hours. After washing (3×) with methylene chloride and drying over P$_2$O$_5$ overnight, the resin was treated with HF/anisole at 0° C. for 1 hour. After workup and HPLC purification N-alpha-(4-Fluorobenzoyl)-Orn(N-delta-acetyl)-D-1-Nal-Ser-Tyr-D-Lys(N-epsilon-nicotinyl)-Leu-Arg-Pro-D-AlaNH$_2$ was obtained as the trifluoroacetate salt; $R_T = 32.12$ minutes; Fab Mass spec m/e 1413 (M+H)$^+$. Amino Acid Anal: 1.0 Ala; 1.0 Pro; 1.0 Arg; 1.0 Leu; 0.9 Lys; 0.9 Tyr; 0.6 Ser; 1.0 Orn.

EXAMPLE 90

N-alpha-(4-Fluorobenzoyl)-Orn(N-delta-acetyl)-D-1-Nal-Ser-NMeTyr-D-Lys(N-epsilon-nicotinyl)-Leu-Lys(N-epsilon-isopropyl)-Pro-D-AlaNH$_2$(218)

The procedure described in Example 89 was used, but substituting Boc-NMeTyr(O-2,6-diCl-Bzl) for Boc-Tyr(O-2-Br-Cbz) and Boc-Lys(N,N-epsilon-isopropyl,Cbz) for Boc-Arg(Tos). After HF treatment, workup, and HPLC purification N-alpha-(4-Fluorobenzoyl)-Orn(N-delta-acetyl)-D-1-Nal-Ser-NMeTyr-D-Lys(N-epsilon-nicotinyl)-Leu-Lys(N-epsilon-isopropyl)-Pro-D-AlaNH$_2$ can be obtained as the trifluoroacetate salt; $R_T$=32.42 minutes; Fab Mass spec m/e 1441 (M+H)$^+$. Amino Acid Anal: 1.0 Ala; 1.0 Pro; 1.0 Leu; 0.9 Lys; 1.1 NMeTyr; 0.6 Ser; 1.0 Orn.

EXAMPLE 91

N-alpha-Morpholinocarbonyl-Phe-Trp-Ser-Tyr-D-Trp-Leu-Arg-Pro-D-AlaNH$_2$(219)

The procedure described in Example 32 is used, but substituting Boc-D-Ala-NH-Resin (benzhydrylamine resin) for Boc-Pro-O-Resin (Merrifiled resin). Upon the completion of the synthesis the resin was treated with HF/anisole at 0° C. for 1 hour. After workup and HPLC purification N-alpha-Morpholino-carbonyl-Phe-Trp-Ser-Tyr-D-Trp-Leu-Arg-Pro-D-AlaNH$_2$ was obtained as the trifluoroacetate salt; $R_T$=21.66 minutes; Fab Mass spec m/e 1337 (M+H)$^+$. Amino Acid Anal: 0.98 Ala; 1.1 Pro; 0.94 Arg; 1.98 Trp; 1.02 Tyr; 0.57 Ser; 0.95 Phe.

EXAMPLE 92

The synthetic procedure described in Example 91 is used, but substituting with the appropriate amino acids. After HF treatment, workup, and HPLC purification the following compounds can be obtained as the trifluoroacetate salt:

(2-10)[N-(alpha-Morpholinocarbonyl)-D-1-Nal$^2$-D-Trp$^{3,6}$-NMeTyr$^5$-D-Ala$^{10}$]LHRH (220), $R_T$=28.51 minutes; Fab Mass spec m/e 1401 (M+H)$^+$. Amino Acid Anal: 0.98 Ala; 0.98 Pro; 0.99 Arg; 1.03 Leu; 0.98 Trp; 0.37 Ser.

(2-10)[N-(alpha-Morpholinocarbonyl)-1-Nal$^2$-D-Trp$^{3,6}$-NMeTyr$^5$-D-Ala$^{10}$]LHRH (221), $R_T$=28.73 minutes; Fab Mass spec m/e 1401 (M+H)$^+$. Amino Acid Anal: 0.98 Ala; 1.0 Pro; 0.99 Arg; 1.03 Leu; 0.98 Trp; 0.37 Ser.

(2-10)[N-(alpha-Morpholinocarbonyl)-Phe$^2$-D-Trp$^3$-NMeTyr$^5$-D-Tyr$^6$-D-Ala$^{10}$]LHRH (222), $R_T$=26.18 minutes; Fab Mass spec m/e 1328 (M+H)$^+$. Amino Acid Anal: 1.01 Ala; 1.02 Pro; 1.01 Arg; 1.00 Leu; 0.79 Trp; 0.96 Tyr; 0.26 Ser; 0.92 Phe.

(2-10)[N-(alpha-Morpholinocarbonyl)-1-Nal$^2$-D-Trp$^6$-D-Ala$^{10}$]LHRH (223), $R_T$=48.84 minutes; Fab Mass spec m/e 1387 (M+H)$^+$. Amino Acid Anal: 0.95 Ala; 1.04 Pro; 0.97 Arg; 1.05 Leu; 1.00 Tyr; 0.4 Ser; 1.85 Trp.

(2-10)[N-(alpha-Morpholinocarbonyl)-Phe$^2$-D-Thia$^3$-D-Lys$^6$-D-Ala$^{10}$]LHRH (224), $R_T$=30.24 minutes; Fab Mass spec m/e 1246 (M+H)$^+$. Amino Acid Anal: 1.01 Ala; 0.95 Pro; 1.02 Arg; 1.05 Leu; 1.01 Lys; 0.97 Tyr; 0.59 Ser; 0.99 Phe.

(2-10)[N-(alpha-Morpholinocarbonyl)-Phe$^2$-D-Thia$^3$-D-Lys$^6$(N-epsilon-nicotinyl)-D-Ala$^{10}$]LHRH (225), $R_T$=31.68 minutes; Fab Mass spec m/e 1351 (M+H)$^+$. Amino Acid Anal: 1.01 Ala; 1.01 Pro; 0.98 Arg; 1.04 Leu; 1.01 Lys; 0.96 Tyr; 0.63 Ser; 1.01 Phe.

(2-10)[N-(alpha-Morpholinocarbonyl)-Phe$^2$-D-Thia$^3$-NMeTyr$^5$-D-Lys$^6$-D-Ala$^{10}$]LHRH (226). $R_T$=30.35 minutes; Fab Mass spec m/e 1260 (M+H)$^+$. Amino Acid Anal: 1.01 Ala; 1.00 Pro; 1.00 Arg; 1.04 Leu; 1.00 Lys; 0.6 Ser; 0.96 Phe.

(2-10)[N-(alpha-Morpholinocarbonyl)-Phe$^2$-D-Thia$^3$-NMeTyr$^5$-D-Lys$^6$(N-epsilon-nicotinyl)-D-Ala$^{10}$]LHRH (227), $R_T$=32.12 minutes; Fab Mass spec m/e 1365 (M+H)$^+$. Amino Acid Anal: 1.01 Ala; 1.00 Pro; 0.97 Arg; 1.03 Leu; 0.99 Lys; 0.61 Ser; 0.98 Phe.

(2-10)[N-(alpha-Morpholinocarbonyl)-D-4-Cl-Phe$^2$-D-Thia$^3$-D-Lys$^6$-D-Ala$^{10}$]LHRH (228), $R_T$=32.72 minutes; Fab Mass spec m/e 1286 (M+H)$^+$. Amino Acid Anal: 0.94 Ala; 1.03 Pro; 1.02 Arg; 1.02 Leu; 0.98 Lys; 0.93 Tyr; 0.54 Ser.

(2-10)[N-(alpha-Morpholinocarbonyl)-D-4-Cl-Phe$^2$-D-Thia$^3$-NMeTyr$^5$-D-Lys$^6$-D-Ala$^{10}$]LHRH (229), $R_T$=31.90 minutes; Fab Mass spec m/e 1293 (M+H)$^+$. Amino Acid Anal: 0.96 Ala; 1.04 Pro; 1.03 Arg; 0.98 Leu; 0.99 Lys; 0.5 Ser.

(2-10)[N-(alpha-Morpholinocarbonyl)-4-Cl-Phe$^2$-D-Thia$^3$-NMeTyr$^5$-D-Lys$^6$-D-Ala$^{10}$]LHRH (230), $R_T$=32.70 minutes; Fab Mass spec m/e 1294 (M+H)$^+$. Amino Acid Anal: 0.95 Ala; 1.0 Pro; 1.03 Arg; 1.02 Leu; 0.99 Lys; 0.51 Ser.

(2-10)[N-(alpha-Morpholinocarbonyl)-D-4-Cl-Phe$^2$-D-3-Pal$^3$-NMeTyr$^5$-D-Lys$^6$(N-epsilon-nicotinyl)-Lys$^8$(N-epsilon-isopropyl)-D-Ala$^{10}$]LHRH (231), $R_T$=26.71 minutes; Fab Mass spec m/e 1408 (M+H)$^+$. Amino Acid Anal: 0.95 Ala; 1.00 Pro; 1.05 Leu; 1.01 Lys; 0.45 Ser.

(2-10)[N-(alpha-Morpholinocarbonyl)-D-4-Cl-Phe$^2$-D-3-Pal$^3$-Lys$^5$(N-epsilon-nicotinyl)-D-Lys$^6$(N-epsilon-nicotinyl)-Lys$^8$(N-epsilon-isopropyl)-D-Ala$^{10}$]LHRH (232), $R_T$=22.82 minutes; Fab Mass spec m/e 1464 (M+H)$^+$. Amino Acid Anal: 1.02 Ala; 1.1 Pro; 1.05 Leu; 1.94 Lys; 0.56 Ser.

EXAMPLE 93

N-(alpha-Phenethylaminocarbonyl)-Phe-D-Trp-Ser-NMeTyr-D-Tyr-Leu-Arg-Pro-D-AlaNH$_2$(233)

The synthetic procedure described in Example 92 is used, but substituting phenethylamine for morpholine and substituting the appropriate amino acids. After HF treatment, workup, and HPLC purification N-(alpha-phenethylaminocarbonyl)-Phe-D-Trp-Ser-NMeTyr-D-Tyr-Leu-Arg-Pro-D-AlaNH$_2$ was obtained as the trifluoroacetate salt; $R_T$=26.78 minutes; Fab Mass spec m/e 1362 (M+H)$^+$. Amino Acid Anal: 1.02 Ala; 1.04 Pro; 1.00 Arg; 1.00 Leu; 0.94 Tyr; 0.26 Ser; 0.83 Trp.

EXAMPLE 94

N-(alpha-Phenethylaminocarbonyl)-D-Phe-D-Trp-Ser-NMeTyr-D-Trp-Leu-Arg-Pro-D-AlaNH$_2$(234)

The synthetic procedure described in Example 93 is used, but substituting Boc-D-Phe for Boc-Phe and Boc-D-Trp for Boc-D-Tyr(O-2-Br-Cbz). After HF treatment, workup, and HPLC purification N-(alpha-phenethylaminocarbonyl)-D-Phe-D-Trp-Ser-NMeTyr-D-Trp-Leu-Arg-Pro-D-AlaNH$_2$ was obtained as the trifluoroacetate salt; $R_T$=48.48 minutes; Fab Mass spec m/e 1385 (M+H)$^+$. Amino Acid Anal: 0.96 Ala; 1.04 Pro; 0.99 Arg; 1.06 Leu; 1.77 Trp; 0.43 Ser.

EXAMPLE 95

N-(alpha-Phenethylaminocarbonyl)-Phe-D-Trp-Ser-NMeTyr-D-Trp-Leu-Arg-Pro-D-AlaNH$_2$(235)

The synthetic procedure described in Example 94 is used, but substituting Boc-Phe for Boc-D-Phe. After HF treatment, workup, and HPLC purification N-(alpha-phenethylaminocarbonyl)-Phe-D-Trp-Ser-NMeTyr-D-Trp-Leu-Arg-Pro-D-AlaNH$_2$ was obtained as the trifluoroacetate salt; R$_T$=47.64 minutes; Fab Mass spec m/e 1385 (M+H)$^+$. Amino Acid Anal: 0.97 Ala; 1.0 Pro; 1.02 Arg; 1.06 Leu; 1.76 Trp; 0.39 Ser.

EXAMPLE 96

The procedure described in Example 64 was used, but substituting in the synthesis the appropriate amino acids and amines. After HF treatment, workup, and HPLC purification the following compounds were be obtained and characterized as the trifluoroacetate salts:

(2-9)[N-(alpha-Morpholinocarbonyl)-Phe$^2$-D-Thia$^3$-D-Trp$^6$-Pro$^9$NHEt]LHRH (236), R$_T$=43 24 minutes; Fab Mass spec m/e 1261 (M+H)$^+$. Amino Acid Anal: 1.01 Pro; 1.0 Arg; 1.02 Leu; 1.01 Trp; 1.00 Tyr; 0.5 Ser; 0.96 Phe.

(2-9)[N-(alpha-Morpholinocarbonyl)-Phe$^2$-1-Nal$^3$-D-Trp$^6$-Pro$^9$NHEt]LHRH (237), R$_T$=50.77 minutes; Fab Mass spec m/e 1305 (M+H)$^+$. Amino Acid Anal: 1.02 Pro; 1.1 Arg; 1.07 Leu; 1.08 Trp; 1.02 Tyr; 0.38 Ser; 0.89 Phe.

(2-9)[N-(alpha-Ethylaminocarbonyl)-Phe$^2$-D-1-Nal$^3$-D-Trp$^6$-Pro$^9$NHEt]LHRH (238), R$_T$=48.08 minutes; Fab Mass spec m/e 1263 (M+H)$^+$. Amino Acid Anal: 0.98 Pro; 1.1 Arg; 1.04 Leu; 1.38 Trp; 0.98 Tyr; 0.42 Ser.

(2-9)[N-(alpha-Ethylaminocarbonyl)-Phe$^2$-1-Nal$^3$-D-Trp$^6$-Pro$^9$NHEt]LHRH (239), R$_T$=49.82 minutes; Fab Mass spec m/e 1263 (M+H)$^+$. Amino Acid Anal: 0.99 Pro; 1.0 Arg; 1.03 Leu; 1.2 Trp; 0.99 Tyr; 0.35 Ser.

EXAMPLE 97

N-(alpha-4-Cl-Phenethylaminocarbonyl)-D-4-Cl-Phe-D-Thia-Ser-Tyr-D-Lys-Leu-Arg-Pro-D-AlaNH$_2$(240)

The procedure described in Example 95 was used, but substituting 4-Cl-phenethylamine for phenethylamine, Boc-D-4-Cl-Phe for Boc-Phe, Boc-D-Thia for Boc-D-Trp at position 3, and Boc-D-Lys(N-epsilon-Cbz) for Boc-D-Trp at position 6. After HF treatment, workup, and HPLC purification N-(alpha-4-Cl-Phenethylaminocarbonyl)-D-4-Cl-Phe-D-Thia-Ser-Tyr-D-Lys-Leu-Arg-Pro-D-AlaNH$_2$ was obtained as the trifluoroacetate salt; R$_T$=42.52 minutes; Fab Mass spec m/e 1348 (M+H)$^+$. Amino Acid Anal: 1.02 Ala; 0.96 Pro; 0.97 Arg; 1.04 Leu; 1.00 Lys; 0.91 Tyr; 0.59 Ser.

EXAMPLE 98

N-(alpha-4-Cl-Phenethylaminocarbonyl)-D-4-Cl-Phe-D-Thia-Ser-NMeTyr-D-Lys-Leu-Arg-Pro-D-AlaNH$_2$(241)

The procedure described in Example 97 was used, but substituting Boc-NMeTyr(O-2,6-diCl-Bzl) for Boc-Tyr(O-2,Br-Cbz) and adding 0.1% DMAP to the Boc-Ser(O-Bzl) solution. After HF treatment, workup, and HPLC purification N-(alpha-4-Cl-Phenethylaminocarbonyl)-D-4-Cl-Phe-D-Thia-Ser-NMeTyr-D-Lys-Leu-Arg-Pro-D-AlaNH$_2$ was obtained as the trifluoroacetate salt; R$_T$=43.30 minutes; Fab Mass spec m/e 1390 (M+H)$^+$. Amino Acid Anal: 0.98 Ala; 0.99 Pro; 1.00 Arg; 1.05 Leu; 0.98 Lys; 0.89 NMeTyr; 0.49 Ser.

EXAMPLE 99

N-(3-(4-Chlorophenyl)propionyl)-D-4-Cl-Phe-D-Thia-Ser-Tyr-D-Lys-Leu-Arg-Pro-D-AlaNH$_2$(242)

The procedure described in Example 63 was used, but substituting with the appropriate amino acids and carboxylic acids. After HF treatment, workup, and HPLC purification N-(3-(4-Chlorophenyl)propionyl)-D-4-Cl-Phe-D-Thia-Ser-Tyr-D-Lys-Leu-Arg-Pro-D-AlaNH$_2$ was obtained as the trifluoroacetate salt; R$_T$=25.91 minutes; Fab Mass spec m/e 1333 (M+H)$^+$. Amino Acid Anal: 0.97 Ala; 1.06 Pro; 1.01 Arg; 1.04 Leu; 0.99 Lys; 0.95 Tyr; 0.56 Ser.

EXAMPLE 100

N-(3-(2-Naphthyl)propionyl)-D-4-Cl-Phe-D-3-Pal-Ser-NMeTyr-D-Lys(N-epsilon-nicotinyl)-Leu-Lys(N-epsilon-isopropyl)-Pro-D-AlaNH$_2$(243)

The procedure described in Example 99 was used, but substituting 3(2-naphthyl)propionic acid for 3-(4-chlorophenyl)propionic acid, Boc-D-3-Pal for Boc-D-Thia, Boc-NMeTyr(O-2,6-diCl-Bzl) for Boc-Tyr(O-2-Br-Cbz), Boc-D-Lys(N-epsilon-FMOC) for Boc-D-Lys(N-epsilon-Cbz), Boc-Lys(N,N-epsilon-isopropyl,Cbz) and adding 0.1% DMAP to the Boc-Ser-(O-Bzl) solution. The resin N-(3-(2-Naphthyl)propionyl)-D-4-Cl-Phe-D-3-Pal-Ser(O-Bzl)-NMeTyr(O-2,6-diCl-Bzl)-D-Lys(N-epsilon-FMOC)-Leu-Lys(N,N-epsilon-isopropyl,Cbz)-Pro-D-AlaNH-Resin was treated with 30% piperidine in DMF overnight to remove the FMOC group. After washing (3×) with methylene chloride the resin was coupled with nicotinic acid using two couplings of 1 hour each. After drying over P$_2$O$_5$ overnight, the resin was treated with HF/anisole at 0° C. for 1 hour. Workup and HPLC purification gave N-(3-(2-Naphthyl)propionyl)-D-4-Cl-Phe-D-3-Pal-Ser-NMeTyr-D-Lys(N-epsilon-nicotinyl)-Leu-Lys(N-epsilon-isopropyl)-Pro-D-AlaNH$_2$ as the trifluoroacetate salt; R$_T$=22.50 minutes; Fab Mass spec m/e 1477 (M+H)$^+$. Amino Acid Anal: 0.99 Ala; 0.97 Pro; 1.04 Leu; 1.02 Lys; 0.52 Ser.

EXAMPLE 101

N-(3-(2-Naphthyl)propionyl)-D-4-Cl-Phe-D-3-Pal-Ser-Lys(N-epsilon-nicotinyl)-D-Lys(N-epsilon-nicotinyl)-Leu-Lys(N-epsilon-isopropyl)-Pro-D-AlaNH$_2$(245)

The procedure described in Example 100 was used, but substituting Boc-Lys(N-epsilon-FMOC) for Boc-NMeTyr(O-2,6-diCl-Bzl), excluding addition of 0.1% DMAP and doubling the amount of nicotinic acid and its coupling time. After HF treatment, workup and HPLC purification N-(3-(2-Naphthyl)propionyl)-D-4-Cl-Phe-D-3-Pal-Ser-Lys(N-epsilon-nicotinyl)-D-Lys(N-epsilon-nicotinyl)-Leu-Lys(N-epsilon-isopropyl)-Pro-D-AlaNH$_2$ was obtained as the trifluoroacetate salt; R$_T$=26.47 minutes; Fab Mass spec m/e 1533 (M+H)$^+$. Amino Acid Anal: 0.99 Ala; 0.99 Pro; 1.02 Leu; 1.00 Lys; 0.32 Ser.

N-(3-(2-Naphthyl)propionyl)-D-4-Cl-Phe-D-3-Pal-Ser(O-Bzl)-Lys(N-epsilon-nicotinyl)-D-Lys(N-epsilon-nicotinyl)-Leu-Lys(N-epsilon-isopropy-Pro-D-AlaNH$_2$(246) was obtained as a byproduct from the above synthesis; R$_T$=25.38 minutes; Fab Mass spec m/e 1623 (M+H)⁻. Amino Acid Anal: 0.98 Ala; 0.98 Pro; 1.03 Leu; 1.98 Lys; 0.39 Ser.

EXAMPLE 102

N-(3-(4Chlorophenyl)propionyl)-D-4-Cl-Phe-D-3-Pal-Ser-NMeTyr-D-Lys(N-epsilon-nicotinyl)-Leu-Lys(N-epsilon-isopropyl)Pro-D-AlaNH₂(274)

The procedure described in Example 100 was used, but substituting 3-(4-chlorophenyl)propionic acid for 3-(2-naphthyl)propionic acid. After HF treatment, workup, and HPLC purification N-(3-(4-Chlorophenyl)propionyl)-D-4-Cl-Phe-D-3-Pal-Ser-NMeTyr-D-Lys(N-epsilon-nicotinyl)-Leu-Lys(N-epsilon-isopropyl)-Pro-D-AlaNH₂ was obtained as the trifluoroacetate salt; $R_T$=22.07 minutes; Fab Mass spec m/e 1461 (M+H)⁺. Amino Acid Anal: 0.99 Ala; 0.99 Pro; 1.02 Leu; 1.00 Lys; 0.32 Ser.

EXAMPLE 103

N-(3-(4-Fluorophenyl)propionyl)-D-4-Cl-Phe-D-Thia-Ser-NMeTyr-D-Lys-Leu-Arg-Pro-D-AlaNH₂(248)

The procedure described in Example 102 was used, but substituting 3-(4-fluorophenyl)propionic acid for 3-(4-chlorophenyl)propionic acid, Boc-D-Thia for Boc-D-3-Pal, Boc-D-Lys(N-epsilon-Cbz) for Boc-D-Lys(N-epsilon-FMOC), and Boc-Arg(Tos) for Boc-Lys(N,N-epsilon-isopropyl,Cbz). After HF treatment, workup, and HPLC purification N-(3-(4-Fluorophenyl)propionyl)-D-4-Cl-Phe-D-Thia-Ser-NMeTyr-D-Lys-Leu-Arg-Pro-D-AlaNH₂ was obtained as the trifluoroacetate salt; $R_T$=23.5 minutes; Fab Mass spec m/e 1337 (M+H)⁺. Amino Acid Anal: 1.00 Ala; 1.03 Pro; 0.97 Arg; 1.02 Leu; 0.98 Lys; 0.5 Ser.

EXAMPLE 104

N-(3-(4-Chlorophenyl)propionyl)-D-4-Cl-Phe-D-1-Nal-Ser-Tyr-D-Lys-Leu-Arg-Pro-D-AlaNH₂(249)

The procedure described in Example 103 was used, but substituting 3-(4-chlorophenyl)propionic acid for 3-(4-fluorophenyl)propionic acid, Boc-D-1-Nal for Boc-D-Thia, and Boc-Tyr(O-2-Br-Cbz) for Boc-NMeTyr(O-2,6-diCl-Bzl) with no addition of 0.1% DMAP. After HF treatment, workup, and HPLC purification N-(3-(4-Chlorophenyl)propionyl)-D-4-Cl-Phe-D-1-Nal-Ser-Tyr-D-Lys-Leu-Arg-Pro-D-AlaNH₂ was obtained as the trifluoroacetate salt; $R_T$=35.3 minutes; Fab Mass spec m/e 1377 (M+H)⁺. Amino Acid Anal: 1.01 Ala; 0.99 Pro; 0.99 Arg; 1.02 Leu; 1.02 Lys; 0.92 Tyr; 0.45 Ser.

EXAMPLE 105

N-(3-(4-Fluorophenyl)propionyl)-D-4-Cl-Phe-D-Thia-Ser-Tyr-D-Lys-Leu-Arg-Pro-D-AlaNH₂(250)

The procedure described in Example 104 was used, but substituting 3-(4-fluorophenyl)propionic acid for 3-(4-chlorophenyl)propionic acid and Boc-D-Thia for Boc-D-1-Nal. After HF treatment, workup, and HPLC purification N-(3-(4-Fluorophenyl)propionyl)-D-4-Cl-Phe-D-Thia-Ser-Tyr-D-Lys-Leu-Arg-Pro-D-AlaNH₂ was obtained as the trifluoroacetate salt; $R_T$=27.02 minutes; Fab Mass spec m/e 1318 (M+H)⁺. Amino Acid Anal: 0.99 Ala; 1.01 Pro; 1.06 Arg; 1.01 Leu; 1.06 Lys; 0.86 Tyr; 0.68 Ser.

EXAMPLE 106

N-(3-(4-Chlorophenyl)propionyl)-D-4-Cl-Phe-NMe-D-1-Nal-Ser-Tyr-D-Lys-Leu-Arg-Pro-D-AlaNH₂(251)

The procedure described in Example 104 was used, but substituting Boc-NMe-D-1-Nal for Boc-D-1-Nal and adding 0.1% DMAP to the solution of Boc-D-4-Cl-Phe. After HF treatment, workup, and HPLC purification N-(3-(4-Chlorophenyl)propionyl)-D-4-Cl-Phe-NMe-D-1-Nal-Ser-Tyr-D-Lys-Leu-Arg-Pro-D-AlaNH₂ was obtained as the trifluoroacetate salt; $R_T$=26.74 minutes; Fab Mass spec m/e 1391 (M+H)⁺. Amino Acid Anal: 1.02 Ala; 0.97 pro; 0.8 Arg; 1.00 Leu; 1.00 Lys; 0.83 Tyr; 0.42 Ser.

EXAMPLE 107

The procedure described in Example 81 was used, but substituting in the synthesis the appropriate amino acids without addition of 0.1% DMAP when NMeTyr is absent. After HF treatment, workup, and HPLC purification the following compounds were obtained:

(3-10)[N-(3-(4-Fluorophenyl)propionyl)-D-1-Nal³-Phe⁵-D-Lys⁶(N-epsilon-nicotinyl)-Lys⁸(N-epsilon-isopropyl)-D-Ala¹⁰]LHRH (252), $R_T$=42.43 minutes; Fab Mass spec m/e 1283 (M+H)⁺. Amino Acid Anal: 0.9 Ala; 1.0 Pro; 1.1 Leu; 1.0 Lys; 1.0 Phe; 0.6 Ser.

(3-10)[N-(3-(4-Fluorophenyl)propionyl)-D-3-Bal³-NMeTyr⁵-D-Lys⁶(N-epsilon-nicotinyl)-Lys⁸(N-epsilon-isopropyl)-D-Ala¹⁰]LHRH (253), $R_T$=39.30 minutes; Fab Mass spec m/e 1319 (M+H)⁺. Amino Acid Anal: 0.9 Ala; 1.1 Pro; 1.1 Leu; 1.0 Lys; 0.6 Ser.

(3-10)[N-(3-(4-Fluorophenyl)propionyl)-D-Cha³-NMeTyr⁵-D-Lys⁶(N-epsilon-nicotinyl)-Lys⁸(N-epsilon-isopropyl)-D-Ala¹⁰]LHRH (254), $R_T$=39.08 minutes; Fab Mass spec m/e 1269 (M+H)⁺. Amino Acid Anal: 0.9 Ala; 1.1 Pro; 1.1 Leu; 1.1 Lys; 0.6 Ser.

EXAMPLE 108

N-(3-(4-Fluorophenyl)propionyl)-D-1-Nal-Ser-NMeTyr-D-Lys(N-epsilon-nicotinyl)-Leu-Lys(N-epsilon-isopropyl)-Pro-SarNH₂(255)

The procedure described in Example 81 was used, but substituting Boc-Sar-NH-Resin for Boc-D-Ala-NH-Resin. After HF treatment, workup, and HPLC purification N-(3-(4-Fluorophenyl)propionyl)-D-1-Nal-Ser-NMeTyr-D-Lys(N-epsilon-nicotinyl)-Leu-Lys(N-epsilon-isopropyl)-Pro-SarNH₂ was obtained as the trifluoroacetate salt; $R_T$=38.7 minutes; Fab Mass spec m/e 1313 (M+H)⁺. Amino Acid Anal: 1.3 Sar; 0.9 Pro; 1.0 Leu; 1.0 Lys; 0.7 Ser.

EXAMPLE 109

N-(3-(4-Fluorophenyl)propionyl)-D-1-Nal-Ser-NMeTyr-D-Ser(O-alpha-L-Rha)-Leu-Lys(N-epsilon-isopropyl)-Pro-D-AlaNH₂

The peptide Leu-Lys(N,N-epsilon-isopropyl,Cbz)-Pro-D-AlaNH₂ is prepared by solid phase synthesis and afterwards is coupled to N-alpha-FMOC-D-Ser(O-tri-Ac-alpha-L-Rhamnosyl)-OH in DMF and in the presence of DCC and HOBt to give after purification N-alpha-FMOC-D-Ser(O-tri-Ac-alpha-L-Rhamnosyl)-Leu-Lys(N,N-epsilon-isopropyl,Cbz)-Pro-D-AlaNH₂. The obtained peptides is treated with 30% diisopropylamine in DMF and then coupled to N-(3-(4-fluorophenyl)propionyl)-D-1-Nal-Ser-NMeTyr-OH using the aforementioned conditions to give N-(3-(4-fluorophenyl)propionyl)-D-1-Nal-Ser-NMeTyr-D-Ser(O-tri-Ac-alpha-L-Rhamnosyl)-Leu-Lys(N,N-epsilon-isopropyl,Cbz)-Pro-D-AlaNH₂. This peptide is catalytically hydrogenated in methanol at pH 4.5 in the presence of Pd catalyst. At the end of the reaction the catalyst is filtered and the filtrate is concentrated in vacuo. The residue is dissolved in dimethylacetamide and treated with hydrazine hydrate for 4 hours at room temperature. After removal of the solvents in vacuo and purification of the residue with HPLC N-(3-(4-Fluorophenyl)propionyl)-D-1-Nal-Ser-NMeTyr-D-Ser(O-alpha-L Rha)-Leu Lys(N-epsilon-isopropyl)-Pro-D-AlaNH₂ can be obtained as the trifluoroacetate salt.

EXAMPLE 110

N-(3-(4-Fluorophenyl)propionyl)-D-1-Nal-Ser-NMeTyr-D-Lys(N-epsilon-nicotinyl)-Leu-Lys(N-epsilon-isopropyl)-Pro-azaGlyNH₂

To a solution of Cbz-Pro (1.25 g), semicarbazide hydrochloride (5.5 g), and HOBt (6.75 g) in DMF (100 mL) is added triethylamine (7.5 mL) and DCC (10.5 g) at 0° C. with stirring. The reaction is stirred at 0° C. for 24 hours. The precipitate is filtered and the filtrate is concentrated in vacuo. The residue is triturated with saturated NaHCO₃ solution, filtered, washed with water and dried to give Cbz-Pro-azaGlyNH₂. Cbz-Pro-azaGlyNH₂ (10 g) is catalytically hydrogenated in (1:1) methanol/DMF at pH 4.5 in the presence of Pd catalyst. At the end of the hydrogenation the catalyst is filtered and the filtrate is concentrated in vacuo to give H-Pro-azaGlyNH₂.HCl. To a solution of H-Pro-azaGlyNH₂.HCl (2.08 g), HOBt (1.63 g), and Boc-Lys(N,N-epsilon-isopropyl,Cbz)-OH (1.26 g) in DMF (40 mL), DCC (2.1 g) is added with stirring at 0° C. for 2 hours and then at 4° C. for 24 hours. After workup and trituration with ether Boc-Lys(N,N-epsilon-isopropyl,Cbz)-Pro-azaGlyNH₂ is obtained.

Boc-Lys(N,N-epsilon-isopropyl,Cbz)-Pro-azaGlyNH₂ is treated with 50% TFA/methylene chloride at room temperature for 1 hour. After removal in vacuo of solvent and reagent the residue is triturated with ether to give after drying H-Lys(N,N-epsilon-isopropyl,Cbz)-Pro-azaGlyNH₂.

H-Lys(N,N-epsilon-isopropyl,Cbz)-Pro-azaGlyNH₂ is coupled to N-(3-(4-fluorophenyl)propionyl)-D-1-Nal-Ser-NMeTyr-D-Lys(N-epsilon-nicotinyl)-Leu-OH in the presence of DCC and HOBt using the aforementioned conditions to give after workup N-(3-(4-fluorophenyl)propionyl)-D-1-Nal-Ser-NMeTyr-D-Lys(N-epsilon-nicotinyl)-Leu-Lys(N,N-epsilon-isopropyl,Cbz)-Pro-azaGlyNH₂. This peptide is catalytically hydrogenated in (1:1) methanol/DMF at pH 4.5 in the presence of Pd catalyst. At the end of the hydrogenation the catalyst is filtered and the filtrate is concentrated in vacuo to give after HPLC purification N-(3-(4-fluorophenyl)propionyl)-D-1-Nal-Ser-NMeTyr-D-Lys(N-epsilon-nicotinyl)-Leu-Lys(N-epsilon-isopropyl)-Pro-azaGlyNH₂ as the trifluoroacetate salt.

EXAMPLE 111

N-(3-(4-Fluorophenyl)propionyl)-D-1-Nal-Ser-NMeTyr(OMe)-D-Lys(N-epsilon-nicotinyl)-Leu-Lys(N-epsilon-isopropyl)-Pro-D-AlaNH₂

The procedure described in Example 81 is used, but substituting Boc-NMeTyr(OMe) for Boc-NMeTyr(O-2,6-diCl-Bzl). After HF treatment, workup, and HPLC purification N-(3-(4-Fluorophenyl)propionyl)-D-1-Nal-Ser-NMeTyr(OMe)-D-Lys(N-epsilon-nicotinyl)-Leu-Lys(N-epsilon-isopropyl)-Pro-D-AlaNH₂ can be obtained as the trifluoroacetate salt.

EXAMPLE 112

The procedure described in Example 111 is used, but substituting with the appropriate amino acids at the position 3 the following compounds can be obtained:

N-(3-(4-fluorophenyl)propionyl)-D-3-(3-benzthienyl)alanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide.

N-(3-(4-fluorophenyl)propionyl)-D-3-(2-thienyl)alanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide.

N-(3-(4-fluorophenyl)propionyl)-D-tryptyl(N-indoleformyl)-seryl-N-alpha-methyl-tyrosyl(O-methyl)-D-lysyl(N-epsilon-nicotinyl)-leucyl-lysyl(N-epsilon-isopropyl)-prolyl-D-alanylamide.

N-(3-(4-fluorophenyl)propionyl)-D-4-chlorophenylalanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide.

N-(3-(4-fluorophenyl)propionyl)-D-3-(2-naphthyl)alanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide.

N-(3-(4-fluorophenyl)propionyl)-D-phenylalanyl-seryl-N-alpha-methyl-tyrosyl(O-methyl)-D-lysyl(N-epsilon-nicotinyl)-leucyl-lysyl(N-epsilon-isopropyl)-prolyl-D-alanylamide.

N-(3-(4-fluorophenyl)propionyl)-D-tyrosyl(O-methyl)seryl -N-alpha-methyl-tyrosyl(O-methyl)-D-lysyl(N-epsilon-nicotinyl)-leucyl-lysyl(N-epsilon-isopropyl)-prolyl-D-alanylamide.

N-(3-(4-fluorophenyl)propionyl)-D-(4-methylphenyl)alanyl -seryl-N-alpha-methyl-tyrosyl(O-methyl)-D-lysyl(N-epsilon-nicotinyl)-leucyl-lysyl(N-epsilon -isopropyl)-prolyl-D-alanylamide.

N-(3-(4-fluorophenyl)propionyl)-D-(3-cyclohexyl)alanyl-seryl -N-alpha-methyl-tyrosyl(0-methyl)-D-lysyl(N-epsilon -nicotinyl)-leucyl-lysyl(N-epsilon-isopropyl)-prolyl-D-alanylamide.

N-(3-(4-fluorophenyl)propionyl)-D-3-(3,4,5-trimethylphenyl)alanyl -seryl-N-alpha-methyl-tyrosyl(O-methyl) -D-lysyl(N-epsilon-nicotinyl)-leucyl-lysyl(N-epsilon-isopropyl)-prolyl-D-alanylamide.

N-(3-(4-fluorophenyl)propionyl)-D-3-(pentamethylphenyl)alanyl -seryl-N-alpha-methyltyrosyl(O-methyl)-D-lysyl(N-epsilon-nicotinyl)-leucyl-lysyl(N-epsilon-isopropyl)-prolyl-D-alanylamide.

N-(3-(4-fluorophenyl)propionyl)-D-tryptyl(N-indolemethyl) -seryl-N-alpha-methyl-tyrosyl(0-methyl)-D-lysyl(N-epsilon-nicotinyl)-leucyl-lysyl(N-epsilon-isopropyl) -prolyl-D-alanylamide.

N-(3-(4-fluorophenyl)propionyl)-D-3-(biphenyl)alanyl-seryl -N-alpha-methyl-tyrosyl(O-methyl)-D-lysyl(N-epsilon-nicotinyl)-leucyl-lysyl(N-epsilon-isopropyl)-prolyl-D-alanylamide.

N-(3-(4-fluorophenyl)propionyl)-D-3-(7-methyl)tryptyl-seryl -N-alpha-methyl-tyrosyl(O-methyl)-D-lysyl(N-epsilon -nicotinyl)-leucyl-lysyl(N-epsilon-isopropyl)-prolyl-D-alanylamide.

N-(3-(4-fluorophenyl)propionyl)-D-3-(4-methyl)tryptyl-seryl -N-alpha-methyl-tyrosyl(O-methyl)-D- lysyl(N-epsilon -nicotinyl)-leucyl-lysyl(N-epsilon-isopropyl)-prolyl-D-alanylamide.

N-(3-(4-fluorophenyl)propionyl)-D-3-(1-adamantyl)alanyl-seryl -N-alpha-methyl-tyrosyl(O-methyl)-D-lysyl(N-epsilon -nicotinyl)-leucyl-lysyl(N-epsilon-isopropyl)-prolyl-D-alanylamide.

EXAMPLE 113

The procedure described in Example 81 is used, but substituting Boc-Ser(O-Bzl) with the appropriate amino acids. After HF treatment, workup, and HPLC purification the following compounds can be obtained:

N-(3-(4-fluorophenyl)propionyl)-D-3-(1-naphthyl)alanyl-threonyl -N-alpha-methyl-tyrosyl-D-lysyl(N-epsilon-nicotinyl) -leucyl-lysyl(N-epsilon-isopropyl)-prolyl-D-alanylamide.

N-(3-(4-fluorophenyl)propionyl)-D-3-(1-naphthyl)alanyl-alanyl -N-alpha-methyl-tyrosyl-D-lysyl(N-epsilon-nicotinyl) -leucyl-lysyl(N-epsilon-isopropyl)-prolyl-D-alanylamide.

N (3-(4-fluorophenyl)propionyl)-D-3-(1-naphthyl)alanyl-(alpha -amino-beta-guanidino)propionyl-N-alpha-methyl-tyrosyl -D-lysyl(N-epsilon-nicotinyl)-leucyl-lysyl(N-epsilon-isopropyl)-prolyl-D-alanylamide.

N-(3-(4-fluorophenyl)propionyl)-D-3-(1-naphthyl)alanyl-(alpha -amino-beta-amino)propionyl-N-alpha-methyl-tyrosyl -D-lysyl(N-epsilon-nicotinyl)-leucyl-lysyl(N-epsilon-isopropyl)-prolyl-D-alanylamide.

N-(3-(4-fluorophenyl)propionyl)-D-3-(1-naphthyl)alanyl-glutaminyl -N-alpha-methyl-tyrosyl-D-lysyl(N-epsilon-nicotinyl) -leucyl-lysyl(N-epsilon-isopropyl)-prolyl-D-alanylamide.

N-(3-(4-fluorophenyl)propionyl)-D-3-(1-naphthyl)alanylseryl(O -benzyl)-N-alpha-methyl-tyrosyl-D-lysyl(N-epsilon-nicotinyl)-leucyl-lysyl(N-epsilon-isopropyl)-prolyl-D-alanylamide.

N-(3-(4-fluorophenyl)propionyl)-D-3-(1-naphthyl)alanylseryl(O -t-butyl)-N-alpha-methyl-tyrosyl-D-lysyl(N-epsilon -nicotinyl)-leucyl-lysyl(N-epsilon-isopropyl)-prolyl-D-alanylamide.

EXAMPLE 114

The procedure described in Example 81 is used, but substituting Boc-N-Me-Tyr(O-2,6-diCl-Bzl) with the appropriate N-alpha-methyl amino acids at position 5. After HF treatment, workup, and HPLC purification the following compounds can be obtained:

N-(3-(4-fluorophenyl)propionyl)-D-3-(1-naphthyl)alanyl-seryl -N-alpha-methyl-4-chlorophenylalanyl-D-lysyl(N-epsilon -nicotinyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-4-fluorophenylalanyl-D-lysyl(N-epsilon -nicotinyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-3-cyclohexylalanyl-D-lysyl(N-epsilon -nicotinyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl(O-ethyl)-D-lysyl(N-epsilon-nicotinyl) -leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-histidinyl-D-lysyl(N-epsilon-nicotinyl) -leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-arginyl-D-lysyl(N-epsilon-nicotinyl) -leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-arginyl(N,N-guanidine-diethyl)-D-lysyl (N-epsilon-nicotinyl)-leucyl-lysyl(N-epsilon-isopropyl)-prolyl-D-alanylamide.

N-(3-(4-fluorophenyl)propionyl)-D-3-(1-naphthyl)alanyl-seryl-N-alpha-methyl-citrullinyl-D-lysyl(N-epsilon-nicotinyl -leucyl-lysyl(N-epsilon-isopropyl)-prolyl-D-alanylamide.

N-(3-(4-fluorophenyl)propionyl)-D-3-(1-naphthyl)alanyl-seryl-N-alpha-methyl-(4-aminophenyl)alanyl-D-lysyl (N-epsilon-nicotinyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-(4-nitrophenyl)alanyl-D-lysyl(N-epsilon -nicotinyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-(4-aminoacetylphenyl)alanyl-D-lysyl (N-epsilon-nicotinyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-lysyl(N-epsilon-nicotinyl)-D-lysyl (N-epsilon-nicotinyl)-leucyl-lysyl(N-epsilon-isopropyl)-prolyl-D-alanylamide.

EXAMPLE 115

The procedure described in Example 81 is used, but substituting with the appropriate amino acids at position 3. After HF treatment, workup, and HPLC purification the following compounds can be obtained:

N-(3-(4-fluorophenyl)propionyl)-D-tryptyl(N-indoleformyl)-seryl-N-alpha-methyl-tyrosyl-D-lysyl(N-epsilon-nicotinyl) -leucyl-lysyl(N-epsilon-isopropyl)-prolyl-D-alanylamide.

N-(3-(4-fluorophenyl)propionyl)-D-3-(2-thienyl)alanyl-seryl -N-alpha-methyl-tyrosyl-D-lysyl(N-epsilon-nicotinyl) -leucyl-lysyl(N-epsilon-isopropyl)-prolyl-D-alanylamide.

N-(3-(4-fluorophenyl)propionyl)-D-tryptyl(N-indolemethyl) -seryl-N-alpha-methyl-tyrosyl-D-lysyl(N-epsilon-nicotinyl)-leucyl-lysyl(N-epsilon-isopropyl)-prolyl-D-alanylamide.

N-(3-(4-fluorophenyl)propionyl)-D-(2-methyl)tryptyl-seryl-N-alpha-methyl-tyrosyl-D-lysyl(N-epsilon-nicotinyl) -leucyl-lysyl(N-epsilon-isopropyl)-prolyl-D-alanylamide.

N-(3-(4-fluorophenyl)propionyl)-D-(7-methyl)tryptyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(4-fluorophenyl)propionyl)-D-(4-methyl)tryptyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(4-fluorophenyl)propionyl)-D-(5-fluoro)tryptyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(4-fluorophenyl)propionyl)-D-(6-fluoro)tryptyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(4-fluorophenyl)propionyl)-D-3-(4-chlorophenyl)alanyl -seryl-N-alpha-methyl-tyrosyl-D-lysyl(N- epsilon-nicotinyl)-leucyl-lysyl(N-epsilon-isopropyl)-prolyl-D-alanylamide.

N-(3-(4-fluorophenyl)propionyl)-D-3-(2-naphthyl)alanyl-seryl-N-alpha-methyl-tyrosyl-D-lysyl(N-epsilon-nicotinyl)-leucyl-lysyl(N-epsilon-isopropyl)-prolyl-D-alanylamide.

N-(3-(4-fluorophenyl)propionyl)-D-phenylalanyl-seryl-N-alpha-methyl-tyrosyl -D-lysyl(N-epsilon-nicotinyl)-leucyl-lysyl(N-epsilon-isopropyl)-prolyl-D-alanylamide.

N-(3-(4-fluorophenyl)propionyl)-D-tyrosyl(O-methyl)-seryl -N-alpha-methyl-tyrosyl-D-lysyl(N-epsilon-nicotinyl)-leucyl-lysyl(N-epsilon-isopropyl)-prolyl-D-alanylamide.

N-(3-(4-fluorophenyl)propionyl)-D-3-(4-methylphenyl)alanyl-seryl-N-alpha-methyl-tyrosyl-D-lysyl (N-epsilon-nicotinyl)-leucyl-lysyl(N-epsilon-isopropyl)-prolyl-D-alanylamide.

N-(3-(4-fluorophenyl)propionyl)-D-3-(3,4,5-trimethylphenyl)alanyl-seryl-N-alpha-methyl-tyrosyl-D-lysyl (N-epsilon-nicotinyl)-leucyl-lysyl(N-epsilon-isopropyl)-prolyl-D-alanylamide.

N-(3-(4-fluorophenyl)propionyl)-D-3-(pentamethylphenyl)alanyl-seryl-N-alpha-methyl-tyrosyl-D -lysyl(N-epsilon-nicotinyl)-leucyl-lysyl(N-epsilon-isopropyl)-prolyl-D-alanylamide.

N-(3-(4-fluorophenyl)propionyl)-D-3-(biphenyl)alanyl-seryl-N-alpha-methyl-tyrosyl-D-lysyl(N-epsilon-nicotinyl) -leucyl-lysyl(N-epsilon-isopropyl)-prolyl-D-alanylamide.

N-(3-(4-fluorophenyl)propionyl)-D-3-(1-adamantyl)alanyl-seryl-N-alpha-methyl-tyrosyl-D-lysyl(N-epsilon-nicotinyl) -leucyl-lysyl(N-epsilon-isopropyl)-prolyl-D-alanylamide.

EXAMPLE 116

The procedure described in Example 81 is used, but substituting nicotinic acid with the appropriate carboxylic acids. After HF treatment, workup, and HPLC purification the following compounds can be obtained:

N-(3-(4-fluorophenyl)propionyl)-D-3-(1-naphthyl)alanyl-seryl-N-alpha-methyl-tyrosyl-D-lysyl(N-epsilon -3-indolecarbonyl)-leucyl-lysyl(N-epsilon-isopropyl)-prolyl-D-alanylamide.

N-(3-(4-fluorophenyl)propionyl)-D-3-(1-naphthyl)alanyl-seryl-N-alpha-methyl-tyrosyl-D-lysyl(N-epsilon -2-indolecarbonyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-3-quinolinecarbonyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-2-pyridinecarbonyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-(3-pyridine)acetyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-(4-methoxyphenyl)acetyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-3-methoxybenzoyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl-N'-oxide)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-2-methylnicotinyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-6-methylnicotinyl)-leucyl-lysyl(N-epsilon-isopropyl)-prolyl-D-alanylamide.

EXAMPLE 117

The procedure described in Example 116 is used, but substituting Boc-D-Orn(N-delta-FMOC) for Boc-D-Lys(N-epsilon-FMOC). After HF treatment, workup, and HPLC purification the following compounds can be obtained:

N-(3-(4-fluorophenyl)propionyl)-D-3-(1-naphthyl)alanyl-seryl -N-alpha-methyl-tyrosyl-D-ornithyl(N-delta-nicotinyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-ornithyl(N-delta-3-indolecarbonyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-ornithyl(N-delta-2-indolecarbonyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-ornithyl(N-delta-3-quinolinecarbonyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-ornithyl(N-delta-2-pyridinecarbonyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-ornithyl(N-delta-(3-pyridine)acetyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-ornithyl(N-delta-(4-methoxyphenyl)acetyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-ornithyl(N-delta-3-methoxybenzoyl)-leucyl-lysyl(N-epsilon-isopropyl)-prolyl-D-alanylamide.

N-(3-(4-fluorophenyl)propionyl)-D-3-(1-naphthyl)alanyl-seryl-N-alpha-methyl-tyrosyl-D-ornithyl(N-delta-nicotinyl -N'-oxide)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-ornithyl(N-delta-2-methylnicotinyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-ornithyl(N-delta-6-methylnicotinyl)-leucyl-lysyl(N-epsilon-isopropyl)-prolyl-D-alanylamide.

EXAMPLE 118

N-(3-(4-Fluorophenyl)propionyl)-D-1-Nal-Ser-NMeTyr-D-Lys (N-epsilon-hydrazinecarbonyl)-Leu-Lys(N-epsilon-isopropyl)-Pro-D-AlaNH$_2$ The procedure described in Example 82 was used, but substituting anhydrous hydrazine for morpholine and running the reaction overnight. After HF treatment, workup, and HPLC purification N-(3-(4-Fluorophenyl)propionyl)-D-1-Nal-Ser-NMeTyr-D-Lys(N-epsilon -hyrdazinecarbonyl)-Leu-Lys(N-epsilon-isopropyl)-Pro-D-AlaNH$_2$ can be obtained as the trifluoroacetate salt.

EXAMPLE 119

N-(3-(4-Fluorophenyl)propionyl)-D-1-Nal-Ser-NMeTyr-D-Lys (N-epsilon-(N'-acetyl-alpha-azaglycyl))-Leu-Lys(N-epsilon-isopropyl)-Pro-D-AlaNH$_2$ The procedure described in Example 118 is used, but substituting acetic hydrazide for anhydrous hydrazine. After HF treatment, workup, and HPLC purification N-(3-(4-Fluorophenyl)propionyl)-D-1-Nal-Ser-NMeTyr-D-Lys(N-epsilon -(N'-acetyl-alpha-azaglycyl))-Leu-Lys(N-epsilon-isopropyl)-Pro-D-AlaNH$_2$ can be obtained as the trifluoroacetate salt.

EXAMPLE 120

N-(3-(4-Fluorophenyl)propionyl)-D-1-Nal-Ser-NMeTyr-D-Lys (N-epsilon-3-amino-pyridinecarbonyl)-Leu-Lys(N-epsilon-isopropyl)-Pro-D-AlaNH$_2$ The procedure described in Example 119 used, but substituting 3-aminopyridine for acetic hydrazide. After HF treatment, workup, and HPLC purification N-(3-(4-Fluorophenyl)propionyl)-D-1-Nal-Ser-NMeTyr-D-Lys(N-epsilon -3-amino-pyridinecarbonyl)-Leu-Lys(N-epsilon-isopropyl)-Pro-D-AlaNH$_2$ can be obtained as the trifluoroacetate salt.

EXAMPLE 121

The procedure described in Example 85 is used, but substituting the appropriate primary or secondary amines for morpholine. After HF treatment, workup, and HPLC purification the following compounds can be obtained:

N-(3-(4-fluorophenyl)propionyl)-D-3-(1-naphthyl)alanyl-seryl -N-alpha-methyl-tyrosyl-D-lysyl(N-epsilon-N'-acetylpiperazinecarbonyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-pyrolidinocarbonyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-piperidinocarbonyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-diethylaminocarbonyl)-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-(4-methoxyanilinocarbonyl)-leucyl-lysyl(N-epsilon-isopropyl)-prolyl-D-alanylamide.

EXAMPLE 122

The procedure described in Example 80 is used, but substituting the appropriate amino acids at position 7 for Boc-Leu. After HF treatment, workup, and HPLC purification the following compounds can be obtained:

N-(3-(4-fluorophenyl)propionyl)-D-3-(1-naphthyl)alanyl-seryl -N-alpha-methyl-tyrosyl-D-lysyl(N-epsilon-nicotinyl)-(3-cyclohexyl)alanyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-seryl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-threonyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-norleucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-phenylalanyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-methionyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-tryptyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-seryl(O-t-butyl)-lysyl(N-epsilon-isopropyl)-prolyl-D-alanylamide.

EXAMPLE 123

The procedure described in Example 80 is used, but substituting the appropriate N-methyl amino acids for Boc-Leu and adding 0.1% DMAP to the solution of Boc-D-Lys(N-epsilon-FMOC). After HF treatment, workup, and HPLC purification the following compounds can be obtained:

N-(3-(4-fluorophenyl)propionyl)-D-3-(1-naphthyl)alanyl-seryl -N-alpha-methyl-tyrosyl-D-lysyl(N-epsilon-nicotinyl)-N-alpha-methyl-leucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-N-alpha-methyl-(3-cyclohexyl)alanyl-lysyl(N-epsilon -isopropyl)-prolyl-D-alanylamide.

N-(3-(4-fluorophenyl)propionyl)-D-3-(1-naphthyl)alanyl-seryl-N-alpha-methyl-tyrosyl-D-lysyl(N-epsilon-nicotinyl) -N-alpha-methyl-norleucyl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl) -N-alpha-methyl-seryl-lysyl(N-epsilon-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl) -N-alpha-methyl-seryl(O-t-butyl)-lysyl(N-epsilon-isopropyl)-prolyl-D-alanylamide.

EXAMPLE 124

The procedure described in Example 80 was used, but substituting the appropriate amino acids at position 8 for Boc-Lys(N,N-epsilon-isopropyl,Cbz). After HF treatment, workup, and HPLC purification the following compounds can be obtained:

N-(3-(4-fluorophenyl)propionyl)-D-3-(1-naphthyl)alanyl-seryl -N-alpha-methyl-tyrosyl-D-lysyl(N-epsilon-nicotinyl)-leucyl-ornithyl(N-delta-isopropyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-leucyl-lysyl(N-epsilon-cyclohexyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-leucyl-lysyl(N-epsilon-propyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-leucyl-lysyl(N-epsilon-ethyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-leucyl-lysyl(N-epsilon-cyclopentyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-leucyl-lysyl(N-epsilon-cycloheptyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-leucyl-lysyl(N-epsilon-methyl)-prolyl-D-alanylamide.

N-(3-(4-fluorophenyl)propionyl)-D-3-(1-naphthyl)alanyl-seryl -N-alpha-methyl-tyrosyl-D-lysyl(N-epsilon-nicotinyl)-leucyl-lysyl(N,N-epsilon-dimethyl)-prolyl-D-alanylamide.

EXAMPLE 125

N-(3-(4-Fluorophenyl)propionyl)-D-1-Nal-Ser-NMeTyr-D-Lys (N-epsilon-nicotinyl)-Leu-Hcit-Pro-D-AlaNH$_2$ The procedure described in Example 79 is used, but substituting in compound 173 Boc-D-1-Nal for Boc-D-Trp$^3$(N-indole-formyl), Boc-D-Lys(N-epsilon-nicotinyl) for Boc-D-Lys(N,N-epsilon-isopropyl,Cbz), and Boc-Hcit for Boc-Arg(Tos). After HF treatment, workup, and HPLC purification N-(3-(4-fluorophenyl)-propionyl)-D-1-Nal-Ser-NMeTyr-D-Lys(N-epsilon-nicotinyl)-Leu-Hcit-Pro-D-AlaNH$_2$ can be obtained as the trifluoroacetate salt.

EXAMPLE 126

N-(3-(4-Fluorophenyl)propionyl)-D-1-Nal-Ser-NMeTyr-D-Lys(N-epsilon-nicotinyl)-Leu-Cit-Pro-D-AlaNH$_2$ The procedure described in Example 125 is used, but substituting Boc-Cit for Boc-Hcit. After HF treatment, workup, and HPLC purification N-(3-(4-fluorophenyl)-propionyl)-D-1-Nal-Ser-NMeTyr-D-Lys(N-epsilon-nicotinyl)-Leu-Cit-Pro-D-AlaNH$_2$ can can be obtained as the trifluoroacetate salt.

EXAMPLE 127

N-(3-(4-Fluorophenyl)propionyl)-D-1-Nal-Ser-NMeTyr-D-Lys (N-epsilon-nicotinyl)-Leu-Arg(N$^g$-diethyl)-Pro-D-AlaNH$_2$ The procedure described in Example 79 is used, but substituting in compound 174 Boc-Arg(N$^g$, N$^g$-diethyl,-Tos) for Boc-Arg(Tos). After HF treatment, workup, and HPLC purification N-(3-(4-fluorophenyl)propionyl)-D-1-Nal-Ser-NMeTyr-D-Lys(N-epsilon-nicotinyl)-Leu-Arg(N$^g$-diethyl) -Pro-D-AlaNH2 can be obtained as the trifluoroacetate salt.

EXAMPLE 128

N-(3-(4-Fluorophenyl)propionyl)-D-1-Nal-Ser-NMeTyr-D-Arg(N$^g$-diethyl)-Leu-Arg(N$^g$-diethyl)-Pro-D-AlaNH$_2$ The procedure described in Example 127 is used, but substituting Boc-D-Arg(N$^g$,N$^g$-diethyl,Tos) for Boc-D-Lys(N-epsilon-nicotinyl). After HF treatment, workup, and HPLC purification N-(3-(4-fluorophenyl)propionyl)-D-1-Nal-Ser-NMeTyr-D-Arg(N$^g$-diethyl)-Leu-Arg(N$^g$-diethyl)-Pro-D-AlaNH$_2$ can be obtained as the trifluoroacetate salt.

EXAMPLE 129

N-(3-(4-Fluorophenyl)propionyl)-D-1-Nal-Ser-NMeTyr-D-Lys(N-epsilon-nicotinyl)-Leu-Arg(N$^g$-amino)-Pro-D-AlaNH$_2$ The procedure described in Example 79 for compound 174 is used, but substituting Boc-Orn(N-delta-FMOC) for Boc-Arg(Tos). Upon completion of the synthesis the resin N-(3-(4-fluorophenyl)propionyl)-D-1-Nal-Ser(O-Bzl)-NMeTyr(O-2,6-diCl-Bzl)-D-Lys(N-epsilon-nicotinyl)-Leu-Orn(N-delta-FMOC)-Pro-D-AlaNH-Resin is treated with 30% piperidine/DMF overnight to remove the FMOC group. After washing (3×) with methylene chloride the resin is treated with excess 2-methyl-2-thiopseudosemicarbazide iodide in (1:1) DMF/methylene chloride (20mL), drying overnight over P$_2$O$_5$, treatment with HF/anisole, workup and HPLC purification N-(3-(4-fluorophenyl)propionyl)-D-1-Nal -Ser-NMeTyr-D-Lys(N-epsilon-nicotinyl)-Leu-Arg(N$^g$-amino)-Pro-D-AlaNH$_2$ can be obtained as the trifluoroacetate.

EXAMPLE 130

N-(3-(4-Fluorophenyl)propionyl)-D-1-Nal-Ser-NMeTyr-D-Lys (N-epsilon-nicotinyl)-Leu-Hcit(N$^u$-amino)-Pro-D-AlaNH$_2$ The procedure described in Example 129 is used, but substituting Boc-Lys(N-epsilon-FMOC) for Boc-Orn(N-delta-FMOC). Upon completion of the synthesis the resin N-(3-(4-fluorophenyl)propionyl)-D-1-Nal-Ser-(O-Bzl)-NMeTyr(O-2,6-diCl-Bzl)-D-Lys(N-epsilon-nicotinyl)-Leu-Lys(N-epsilon-FMOC)-Pro-D-AlaNH-Resin is treated with 30% piperidine/DMF overnight to remove the FMOC group. After washing (3×) with methylene chloride the resin is treated with excess of carbonyldiimidazole in DMF for 10 minutes, then washed again (3×) with methylene chloride and reacted overnight with anhydrous hydrazine (3 mL) in (1:1) DMF/methylene chloride (15 mL). The resin is washed, dried over P2O5 overnight, treated with HF/anisole, worked up, and purified by HPLC to give N-(3-(4-fluorophenyl)propionyl)-D-1-Nal-Ser-NMeTyr-D-Lys(N-epsilon-nicotinyl)-Leu-Hcit(Nu-amino)-Pro-D-AlaNH$_2$ as the trifluoroacetate salt.

EXAMPLE 131

N-(3-(4-Fluorophenyl)propionyl)-D-1-Nal-Ser-NMeTyr-D-Lys (N-epsilon-nicotinyl)-Leu-Harg(N$^g$-methyl-N'$^g$-cyano)-Pro-D-AlaNH$_2$ The procedure described in Example 130 is used to give N-(3-(4-fluorophenyl)propionyl)-D-1-Nal-Ser(O-Bzl)-NMeTyr(O-2,6-diCl-Bzl)-D-Lys(N-epsilon-nicotinyl)-Leu-Lys(N-epsilon-FMOC)-Pro-D-AlaNH-Resin. The resin is treated with 30% piperidine/DMF overnight to remove the FMOC group. After washing (3x) with methylene chloride the resin is treated with excess of S-methyl-N-cyano-N'-methylcarbamimidothioate in (1:1) DMF/methylene chloride. The resin is washed, dried over P$_2$O$_5$ overnight, treated with HF/anisole, worked up, and purified by HPLC to give N-(3-(4-fluorophenyl)propionyl)-D-1-Nal-Ser-NMeTyr-D-Lys(N-epsilon-nicotinyl)-Leu-Harg(N$^g$-methyl-N'$^g$-cyano)-Pro-D-AlaNH$_2$ as the trifluoroacetate salt.

EXAMPLE 132

N-(3-(4-Fluorophenyl)propionyl)-D-1-Nal-Ser-NMeTyr-D-Lys (N-epsilon-nicotinyl)-Leu-Lys(N-epsilon-diisopropyl)-Pro-D-AlaNH$_2$ The procedure described in Example 80 is used, but substituting Boc-D-Lys(N-epsilon-nicotinyl) for position 6 and Boc-Lys(N,N-epsilon-isopropyl,FMOC) for position 8. Upon the completion of the synthesis the resin, N-(3-(4-Fluorophenyl)propionyl)-D-1-Nal-Ser-(O-Bzl)-NMeTyr (O-2,6-diCl-Bzl)-D-Lys(N-epsilon-nicotinyl)-Leu-Lys (N,N-epsilon-isopropyl,FMOC)-Pro-D-AlaNH-Resin, is treated with 30% piperidine/DMF overnight to remove the FMOC group. After washing (3×) with methylene chloride the resin is treated with an excess of sodium cyanoborohydride in (3:1:0.1) methylene chloride/acetone/acetic acid for 4 hours. The resin is washed (3×) with methylene chloride, (2×) with methanol, dried over P$_2$O$_5$ overnight, treated with HF/anisole, worked up, and purified by HPLC to give N-(3-(4-fluorophenyl)propionyl)-D-1-Nal-Ser-NMeTyr-D-Lys(N-epsilon-nicotinyl)-Leu-Lys(N-epsilon-diisopropyl)-Pro-D-AlaNH$_2$ as the trifluoroacetate salt.

EXAMPLE 133

N-(3-(4-Fluorophenyl)propionyl)-D-1-Nal-Ser-NMeTyr-D-Lys (N-epsilon-nicotinyl)-Leu-Orn(N-delta-diisopropyl)-Pro-D-AlaNH$_2$ The procedure described in Example 132 is used, but substituting Boc-Orn(N,N-delta-isopropyl,FMOC) for Boc-Lys(N,N-epsilon-isopropyl,FMOC). After HF treatment, workup, and HPLC purification N-(3-(4-Fluorophenyl)propionyl)-D-1-Nal-Ser-NMeTyr-D-Lys(N-epsilon-nicotinyl)-Leu-Orn(N-delta-diisopropyl)-Pro-D-AlaNH$_2$ can be obtained as the trifluoroacetate salt.

EXAMPLE 134

N-(3-(4-Fluorophenyl)propionyl)-D-1-Nal-Ser-NMeTyr-D-Lys(N-epsilon-nicotinyl)-Leu-Lys(N-epsilon-N'-methylpiperazinecarbonyl)-Pro-D-AlaNH$_2$ The procedure described in Example 132 is used, but substituting Boc-Lys(N-epsilon-FMOC) for Boc-Lys(N,N-epsilon-isopropyl,FMOC). Upon the completion of the synthesis the resin N-(3-(4-fluorophenyl)propionyl)-D-1-Nal-Ser(O-Bzl)-NMeTyr(O-2,6-diCl-Bzl)-D-Lys(N-epsilon-nicotinyl)-Leu-Lys(N-epsilon-FMOC)-Pro-D-AlaNH-Resin is treated with 30% piperidine/DMF overnight to remove the FMOC group. After washing (3×) with methylene chloride the resin is treated with a large excess of carbonyldiimidazole in DMF for 10 minutes, washed again, and subsequently treated with a large excess of N-methylpiperazine in (1:1) DMF/methylene chloride overnight. The resin is washed (3×) with methylene chloride, dried over P$_2$O$_5$ overnight, treated with HF/anisole, worked up, and purified by HPLC to give N-(3-(4-fluorophenyl)propionyl)-D-1-Nal-Ser-NMeTyr-D-Lys(N-epsilon-nicotinyl)-Leu-Lys(N-epsilon-N'-methylpiperazinecarbonyl)-Pro-D-AlaNH$_2$ as the trifluoroacetate salt.

EXAMPLE 135

N-(3-(4-Fluorophenyl)propionyl)-D-1-Nal-Ser-NMeTyr-D-Lys (N-epsilon-nicotinyl)-Leu-Lys(N-epsilon-morpholinecarbonyl)-Pro-D-AlaNH$_2$ The procedure described in Example 134 is used, but substituting morpholine for N-methyl-piperazine. After HF treatment, workup, and HPLC purification N-(3-(4-fluorophenyl)propionyl)-D-1-Nal-Ser-NMeTyr-D-Lys(N-epsilon-nicotinylcarbonyl)-Leu-Lys(N-epsilon-morpholine)-Pro-D-AlaNH$_2$ can be obtained as the trifluoroacetate salt.

EXAMPLE 136

N-(3-(4-Fluorophenyl)propionyl)-D-1-Nal-Ser-NMeArg-D-4-(4-methoxybenzoyl)-Homoala-Leu-Arg-Pro-D-AlaNH$_2$ The procedure described in Example 80 is used but substituting in compound 206 Boc-NMeArg(Tos) for Boc-Tyr(O-2-Br-Cbz), Boc-D-4-(4-methoxybenzoyl)-Homoala for Boc-D-Lys(N-epsilon-4-methoxybenzoyl), Boc-Arg(Tos) for Boc-Lys(N,N-epsilon-isopropyl,Cbz) and adding 0.1% DMAP to the Boc-Ser-(O-Bzl) solution. After HF treatment, workup, and HPLC purification N-(3-(4-fluorophenyl)propionyl)-D-1-Nal-Ser-NMeArg-D-4-(4-methoxybenzoyl)-Homoala-Leu-Arg-Pro-D-AlaNH$_2$ can be obtained as the trifluoroacetate salt.

EXAMPLE 137

N-(3-(4-Fluorophenyl)propionyl)-D-1-Nal-Ser-NMeTyr-D-Lys(N-epsilon-nicotinyl)-Leu-NMeArg-Pro-D-AlaNH$_2$ The procedure described in Example 79 is used, but substituting in compound 174 Boc-NMeArg(Tos) for Boc-Arg(Tos) and adding 0.1% DMAP to the solution Boc-Leu. After HF treatment, workup, and HPLC purification N-(3-(4-fluorophenyl)propionyl)-D-1-Nal-Ser-NMeTyr-D-Lys(N-epsilon-nicotinyl)-Leu- NMeArg-Pro-D-AlaNH2 can be obtained as the trifluoroacetate salt.

EXAMPLE 138

N-(3-(4-Fluorophenyl)propionyl)-D-1-Nal-NMeSer-Tyr-D-Lys-Leu-Arg-Pro-D-AlaNH$_2$ The procedure described in Example 79 is used, but substituting in compound 169 Boc-NMeSer(O-Bzl) for Boc-Ser(O-Bzl), Boc-Tyr(O-2-Br-Cbz) for Boc-NMeTyr(O-2,6-diCl-Bzl) and adding 0.1% DMAP to the solution Boc-D-1-Nal. After HF treatment, workup, and HPLC purification N-(3-(4-fluorophenyl)propionyl)-D-1-Nal-NMeSer-Tyr-D-Lys-Leu-Arg-Pro-D-AlaNH$_2$ can be obtained as the trifluoroacetate salt.

EXAMPLE 139

N-(para-Fluorocinnamoyl)-D-1-Nal-Ser-NMeTyr-D-Lys(N-epsilon-nicotinyl)-Leu-Lys(N-epsilon-isopropyl)-Pro-D-AlaNH$_2$ The procedure described in Example 81 is used, but substituting para-fluorocinnamic acid for 3-(4-fluorophenyl)propionic acid. After HF treatment, workup, and HPLC purification N-(para-fluorocinnamoyl)-D-1-Nal-Ser-NMeTyr-D-Lys(N-epsilon-nicotinyl)-Leu-Lys(N-epsilon-isopropyl)-Pro-D-AlaNH$_2$ can be obtained as the trifluoroacetate salt.

EXAMPLE 140

The procedure described in Example 81 is used, but substituting the appropriate carboxylic acids for 3-(4-fluorophenyl)propionic acid. After HF treatment, workup, and HPLC purification the following compounds can be obtained:

N-(3-(4-chlorophenyl)propionyl)-D-3-(1-naphthyl)alanyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(3-fluorophenyl)propionyl)-D-3-(1-naphthyl)alanyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(2-fluorophenyl)propionyl)-D-3-(1-naphthyl)alanyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(3,4-difluorophenyl)propionyl)-D-3-(1-naphthyl)alanyl -seryl-N-alpha-methyl-tyrosyl-D-lysyl(N-epsilon-nicotinyl)-leucyl-lysyl(N-epsilon-isopropyl)-prolyl-D-alanylamide.

N-(3-(2,4-difluorophenyl)propionyl)-D-3-(1-naphthyl)alanyl -seryl-N-alpha-methyl-tyrosyl-D-lysyl(N-epsilon-nicotinyl)-leucyl-lysyl(N-epsilon-isopropyl)-prolyl-D-alanylamide.

N-(3-(2,3-difluorophenyl)propionyl)-D-3-(1-naphthyl)alanyl -seryl-N-alpha-methyl-tyrosyl-D-lysyl(N-epsilon-nicotinyl)-leucyl-lysyl(N-epsilon-isopropyl)-prolyl-D-alanylamide.

N-(3-(pentafluorophenyl)propionyl)-D-3-(1-naphthyl)alanyl -seryl-N-alpha-methyl-tyrosyl-D-lysyl(N-epsilon-nicotinyl)-leucyl-lysyl(N-epsilon-isopropyl)-prolyl-D-alanylamide.

N-(3-(4-bromophenyl)propionyl)-D-3-(1-naphthyl)alanyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(4-trifluoromethylphenyl)propionyl)-D-3-(1-naphthyl)alanyl -seryl-N-alpha-methyl-tyrosyl-D-lysyl(N-epsilon-nicotinyl)-leucyl-lysyl(N-epsilon-isopropyl)-prolyl-D-alanylamide.

N-(3-(4-methylphenyl)propionyl)-D-3-(1-naphthyl)alanyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(4-nitrophenyl)propionyl)-D-3-(1-naphthyl)alanyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(4-cyanophenyl)propionyl)-D-3-(1-naphthyl)alanyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(4-methoxyphenyl)propionyl)-D-3-(1-naphthyl)alanyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(4-hydroxyphenyl)propionyl)-D-3-(1-naphthyl)alanyl-seryl -N-alpha-methyl-tyrosyl-D-lysyl(N-epsilon-nicotinyl)-leucyl-lysyl(N-epsilon-isopropyl)-prolyl-D-alanylamide.

N-(3-(4-aminophenyl)propionyl)-D-3-(1-naphthyl)alanyl-seryl -N-alpha-methyl-tyrosyl-D-lysyl(N-epsilon-nicotinyl)-leucyl-lysyl(N-epsilon-isopropyl)-Prolyl-D-alanylamide.

N-(3-(4-(N-acetylamino) 1-naphthyl)alanyl-seryl-N-alpha-methyl-tyrosyl-D-lysyl(N-epsilon -nicotinyl)-leucyl-lysyl(N-epsilon-isopropyl)-prolyl-D-alanylamide.

EXAMPLE 141

N-(3-(4-Fluorophenyl)propionyl)-D-1-Nal-N-alpha-azaGly-NMeTyr -D-Lys(N-epsilon-nicotinyl)-Leu-Lys(N-epsilon-isopropyl)-Pro-D-AlaNH$_2$ The procedure described in Example 81 is used for synthesizing the (5-10) peptide Boc-NMeTyr(O-2,6-diCl-Bzl) -D-Lys(N-epsilon-nicotinyl)-Leu-Lys(N,N-epsilonisopropyl,Cbz)-Pro-D-AlaNH-Resin. This resin is deblocked for 20 minutes, washed (3×) with base wash and methylene chloride, then reacted with a large excess of carbonyldiimidazole in DMF for 10 minutes. After washing (3×) with methylene chloride the resin is reacted with a large excess of t-butylcarbazate in DMF overnight. After washing (3×) with methylene chloride the resin is deblocked for 20 minutes, washed (3×) with base wash and methylene chloride and then coupled to Boc-D-1-Nal and 3-(4-fluorophenyl)propionic acid using the protocol previously described. After HF treatment, workup, and HPLC purification N-(3-(4-fluorophenyl)propionyl)-D-1-Nal-N-alpha-azaGly-NMeTyr-D-Lys (N-epsilon-nicotinyl)-Leu-Lys(N-epsilon-isopropyl)-Pro-D-AlaNH$_2$ can be obtained as the trifluoroacetate salt.

EXAMPLE 142

N-Acetyl-alpha-aza-4-Cl-Phe-D-1-Nal-Ser-NMeTyr-D-Lys(N-epsilon-nicotinyl)-Leu-Lys(N-epsilon-isopropyl)-Pro-D-AlaNH$_2$ The procedure described in Example 81 is used for synthesizing the (3-10) peptide Boc-D-1-Nal-Ser(O-Bzl)NMeTyr(O-2,6-diCl-Bzl)-D-Lys(N-epsilon-nicotinyl)-Leu-Lys(N,N -epsilon-isopropyl,Cbz)-Pro-D-AlaNH-Resin. This resin is deblocked for 20 minutes, washed (3×) with base wash and methylene chloride, then reacted with a large excess of carbonyldiimidazole in DMF for 10 minutes. After washing (3×) with methylene chloride the resin is reacted with a large excess of N-acetyl-N'-(4-chlorobenzyl)hydrazine in DMF. After washing with methylene chloride (3×) and drying over $P_2O_5$ overnight, the resin is treated with HF/anisole at 0° C. for 1 hour. After workup and HPLC purification N-Acetyl-alpha-aza-4-Cl-Phe-D-1-Nal-Ser-NMeTyr-D-Lys(N-epsilon-isopropyl)-Pro-D-AlaNH$_2$ ca obtained as the trifluoroacetate salt.

EXAMPLE 143

N-(3-(4-Fluorophenyl)propionyl)-D-1-Nal-Ser-NMeTyr-D-Lys (N-epsilon-nicotinyl)-Leu-Lys(N-epsilon-isopropyl)-cis-beta-amino-cyclopentanecarbonyl-D-AlaNH$_2$ and N-(3-(4-Fluorophenyl)propionyl)-D-1-Nal-Ser-NMeTyr-D-Lys (N-epsilon-nicotinyl)-Leu-Lys(N-epsilon-isopropyl)-trans-beta-amino-cyclopentanecarbonyl-D-AlaNH$_2$ The procedure described in Example 81 is used but substituting separately Boc-cis-beta-amino-cyclopentanecarboxylic acid and Boc-trans-beta-amino-cyclopentanecarboxylic acid for Boc-Pro. After HF treatment, workup, and HPLC purification N-(3-(4-fluorophenyl)propionyl)-D-1-Nal-Ser-NMeTyr-D-Lys(N-epsilon-nicotinyl) -Leu-Lys(N-epsilon-isopropyl)-cis-beta-amino-cyclopentanecarbonyl-D-AlaNH$_2$ and N-(3-(4-fluorophenyl)propionyl)-D-1-Nal-Ser-NMeTyr-D-Lys(N-epsilon -nicotinyl)-Leu-Lys(N-epsilon-isopropyl)-trans-beta-amino-cyclopentanecarbonyl-D-AlaNH$_2$ can be obtained as the trifluoroacetate salts.

ASSAY PROCEDURES

The biological activity of the compounds of the invention is determined by the following assays:

(a) Receptor Binding. A radioligand receptor binding assay is performed in a similar way to that described in the literature (J. Marion et al., Mol. Pharmacol. 19 399 (1981)). [D-Leu$^6$-des Gly$^{10}$]-LHRH ethyl amide was radioiodinated by the chloramine-T method and used as the radioligand. Pituitary membranes containing LHRH receptors are prepared in batches from quick-frozen rat pituitaries obtained from Hilltop Labs. The radioligand (50 pM), receptors, and compounds to be tested are coincubated for 2 hours at 4° C. Bound ligand is separated from free ligand via centrifugation and aspiration. Compounds are tested at six half-log concentration increments, and the negative log of the equilibrium dissociation constant ($pK_I$) is calculated from the concentration which displaces 50% of specifically bound radioligand.

(b) In vitro LH Release. This assay has been adopted from the literature (H. A. Jinnah and P. M. Conn, Endocrinology 118 2599 (1986)). Rat pituitaries are removed from immature female rats, minced, and dissociated with collagenase/hyaluronidase. They are allowed to attach to 48-well microtiter plates for 48–72 hours, then are exposed to test compounds for 3 hours at 37° C. The medium is assayed for released LH by RIA (radioimmunoassay). This assay is used to determine quantitatively the potencies of LHRH agonists from the negative log of the concentration which produces half maximal release of LH ($pD_2$).

For assaying LHRH antagonists, exogenous superagonist [D-Leu$^6$-Pro$^9$NHEt]LHRH is added. The suppression of LH release by the antagonist is dose related. The assay determines the potencies of the LHRH antagonists from the negative log of the concentration which produces half-maximum suppression of LH ($pA_2$).

(c) In vivo LH Inhibiton. The compound to be tested is administered at 30 ug/kg subcutaneously by bolus injection to male castrate rats and blood samples are collected periodically over 24 hours. The AUC (area under the curve) of the LH suppression data as a function of time is calculated using the formula log ($LH_t/LH_i$) wherein $LH_t$ is the LH concentration in the blood at time t and $LH_i$ is the initial baseline LH concentration in the blood. The AUC values are negative numbers.

(d) In vivo LH Release. The compound to be tested is administered to castrated rats intraveneously and the serum LH concentration at various time points is measured by RIA. The time integrated LH response is calculated and the dose producing half-maximal LH release ($ED_{50}$) is reported.

The in vitro and in vivo biological activities of representative compounds are shown below.

| Compound # | Receptor Binding $pK_I$ | LH Release $pD_2$ | LH Inhibition $pA_2$ | $ED_{50}$ ug/kg i.v. |
|---|---|---|---|---|
| 1 | 7.17 | 6.85 | | |
| 2 | 7.7 | | 8.8–7.0 | |
| 3 | 7.6 | | 6.6 | |
| 4 | 7.64 | 7.93 | | |
| 5 | 7.3 | | 6.69 | |
| 6 | 6.12 | 6.0 | | |
| 7 | 6.48 | | 5.46 | |
| 8 | 8.65 | | 8.18 | |
| 9 | 9.28 | | 8.74 | |
| 10 | 8.20 | | 7.10 | |
| 11 | 8.43 | | 7.80 | |
| 12 | 8.91 | | 8.52 | |
| 13 | 8.72 | | 7.89 | |
| 14 | 7.80 | | 5.46 | |
| 15 | 8.11 | | 6.24 | |
| 16 | 8.85 | | 7.22 | |
| 17 | 8.18 | | 7.83 | |
| 18 | 8.58 | | 8.20 | |
| 19 | 7.43 | | 8.44 | |
| 20 | 9.55 | | 9.25 | |
| 21 | 6.69 | | 6.72 | |
| 22 | 5.87 | | 5.56 | |
| 23 | 6.71 | 6.93 | | |
| 24 | 8.43 | 7.35 | | 6350 |
| 25 | 6.91 | | 6.72 | |
| 26 | 8.77 | | 7.60 | |
| 27 | 8.86 | | 8.07 | |
| 28 | 9.34 | | 8.50 | |
| 29 | 8.01 | | 7.83 | |
| 30 | 8.46 | | 7.98 | |
| 31 | 7.78 | | 6.06 | |
| 32 | 7.44 | | 6.08 | |
| 33 | 7.86 | | 7.56 | |
| 34 | 7.38 | | 6.45 | |
| 35 | 6.69 | | 6.11 | |
| 36 | 7.77 | | 6.83 | |
| 37 | 7.69 | 8.31 | | 168 |
| 38 | 7.54 | 6.43 | | |
| 39 | 6.93 | 7.33 | | |
| 40 | 5.36 | | | |
| 41 | 5.76 | 4.96 | | |
| 42 | 5.82 | | | |
| 43 | 6.19 | | | |
| 44 | 8.40 | 7.97 | | |
| 45 | 8.22 | | 6.87 | |
| 46 | 7.96 | | 6.61 | |
| 47 | 8.37 | | 7.85 | |
| 49 | 7.26 | | 6.37 | |
| 50 | 6.78 | | 4.90 | |
| 51 | 6.88 | | 4.77 | |
| 52 | 7.66 | | | |

-continued

| Compound # | Receptor Binding pk$_I$ | LH Release pD$_2$ | LH Inhibition pA$_2$ | ED$_{50}$ ug/kg i.v. |
|---|---|---|---|---|
| 53 | 7.56 | | 5.90 | |
| 54 | 7.69 | | 5.25 | |
| 55 | 7.82 | 5.93 | | |
| 56 | 9.19 | | 8.62 | |
| 57 | 9.67 | | 7.58 | |
| 58 | 7.65 | | | |
| 59 | 11.08 | | 9.2 | |
| 60 | 8.28 | | 7.93 | |
| 61 | 9.37 | | 7.44 | |
| 62 | 7.98 | | 7.10 | |
| 63 | 7.30 | | 6.30 | |
| 64 | 6.36 | | 6.70 | |
| 65 | 9.57 | | 7.50 | |
| 66 | 8.75 | | 6.50 | |
| 67 | 9.24 | | 8.20 | |
| 68 | 7.66 | | 6.70 | |
| 69 | 8.98 | | 6.80 | |
| 70 | 9.84 | | 9.70 | |
| 71 | 8.50 | | 7.30 | |
| 72 | 9.78 | | 7.50 | |
| 73 | 7.15 | | 6.63 | |
| 74 | 7.58 | | 7.00 | |
| 75 | 8.15 | | 7.20 | |
| 76 | 7.36 | | 7.02 | |
| 77 | 8.40 | | 7.27 | |
| 78 | 7.97 | | 7.10 | |
| 79 | 8.71 | | 8.10 | |
| 80 | 7.30 | | 6.53 | |
| 81 | 9.23 | | 9.04 | |
| 82 | 9.53 | | 8.24 | |
| 83 | 9.91 | | 8.81 | |
| 84 | 8.85 | | 7.64 | |
| 85 | 10.13 | | 9.80 | |
| 86 | 10.76 | | 10.08 | |
| 87 | 9.89 | | 9.02 | |
| 88 | 10.24 | | 9.35 | |
| 89 | 8.88 | | 9.05 | |
| 90 | 10.50 | | 10.85 | |
| 91 | 10.54 | | 10.41 | |
| 92 | 10.50 | | 7.90 | |
| 93 | 10.80 | | 9.00 | |
| 94 | 9.51 | | 10.50 | |
| 95 | 10.11 | | 8.62 | |
| 96 | 9.57 | | 9.02 | |
| 97 | 10.48 | | 9.23 | |
| 98 | 10.28 | | 9.90 | |
| 99 | 10.08 | | 7.81 | |
| 100 | 8.54 | | 7.35 | |
| 101 | 7.90 | | 7.52 | |
| 102 | 7.76 | | 7.42 | |
| 103 | 10.10 | | 8.88 | |
| 104 | 9.08 | | 8.26 | |
| 105 | 9.25 | | 7.35 | |
| 106 | 9.07 | | 8.58 | |
| 107 | 9.59 | | 8.24 | |
| 108 | 9.74 | | 8.01 | |
| 109 | 9.50 | | 7.80 | |
| 110 | 10.00 | | 9.32 | |
| 111 | 8.56 | | 7.65 | |
| 112 | 9.50 | | 8.15 | |
| 113 | 9.51 | | 8.63 | |
| 114 | 11.24 | | 9.06 | |
| 115 | 8.65 | | 7.94 | |
| 116 | 8.30 | | 7.40 | |
| 117 | 8.73 | | 7.95 | |
| 118 | 8.65 | | 7.94 | |
| 119 | 9.46 | | 7.68 | |
| 120 | 10.49 | | 11.15 | |
| 121 | 10.02 | | 9.94 | |
| 122 | 11.02 | | 10.36 | |
| 123 | 9.48 | | 10.65 | |
| 124 | 9.46 | | 8.84 | |
| 125 | 9.60 | | 8.70 | |
| 126 | 7.43 | | 8.56 | |
| 127 | 9.70 | | 8.37 | |
| 128 | 9.35 | | 8.52 | |
| 129 | 8.73 | | 8.02 | |
| 130 | 9.56 | | 9.00 | |
| 131 | 9.20 | | 8.44 | |

-continued

| Compound # | Receptor Binding pk$_I$ | LH Release pD$_2$ | LH Inhibition pA$_2$ | ED$_{50}$ ug/kg i.v. |
|---|---|---|---|---|
| 132 | 10.05 | | 9.18 | |
| 133 | 8.84 | | 9.10 | |
| 134 | 9.40 | | 8.91 | |
| 135 | 9.34 | | 8.32 | |
| 136 | 9.61 | | 8.53 | |
| 137 | 9.58 | | 8.54 | |
| 138 | 9.00 | | 8.51 | |
| LHRH | 8.90 | 9.27 | | 859 |

| Compound # | Receptor Binding pk$_I$ | LH Inhibition pA$_2$ | AUC (24 hr. after 30 ug/kg) |
|---|---|---|---|
| 139 | 7.76 | 7.42 | |
| 140 | 10.05 | 10.60 | −195 |
| 141 | 10.59 | 99.8 | |
| 142 | 10.14 | 9.84 | −237 |
| 143 | 10.31 | 10.60 | |
| 144 | 10.59 | 11.15 | |
| 145 | 10.60 | 11.30 | −247 |
| 146 | 8.90 | 7.68 | |
| 147 | 10.70 | 8.62 | |
| 148 | 10.26 | 8.00 | |
| 149 | 10.53 | 10.80 | −161 |
| 150 | 10.99 | 10.60 | |
| 151 | 10.55 | 10.45 | |
| 152 | 10.67 | 11.05 | −144 |
| 153 | 10.62 | 10.06 | −115 |
| 154 | 10.50 | 10.80 | −328 |
| 155 | 10.31 | 11.00 | −148 |
| 156 | 10.16 | 11.40 | |
| 157 | 10.32 | 11.25 | |
| 158 | 10.76 | 11.20 | |
| 159 | 10.25 | 11.50 | |
| 160 | 9.96 | 11.00 | |
| 161 | 10.82 | 10.60 | −101 |
| 162 | 10.98 | 10.80 | −119 |
| 163 | 10.60 | 10.50 | −361 |
| 164 | 10.27 | 10.90 | −364 |
| 165 | 10.58 | 8.73 | |
| 166 | 11.31 | 10.00 | −208 |
| 167 | 9.34 | 8.89 | |
| 168 | 9.89 | 9.94 | |
| 169 | 11.18 | 11.35 | −1142 |
| 170 | 10.69 | 9.61 | |
| 171 | 10.17 | 9.82 | |
| 172 | 8.92 | 8.30 | |
| 173 | 11.24 | 10.60 | −241 |
| 174 | 10.88 | 11.25 | −938 |
| 175 | 11.20 | 10.25 | −394 |
| 176 | 8.54 | 8.84 | |
| 177 | 11.23 | 11.30 | −938 |
| 178 | 11.02 | 11.50 | −371 |
| 179 | 11.34 | 11.67 | −781 |
| 180 | 11.26 | 10.70 | |
| 181 | 11.40 | 11.20 | −363 |
| 182 | 10.55 | 9.32 | |
| 183 | 10.58 | 9.36 | |
| 184 | 11.20 | 10.90 | −442 |
| 185 | 10.81 | 11.55 | −879 |
| 186 | 10.47 | 10.75 | −378 |
| 187 | 10.65 | 10.80 | −239 |
| 188 | 11.48 | 10.60 | |
| 189 | 11.26 | 11.70 | −442 |
| 190 | 10.80 | 11.25 | |
| 191 | 11.02 | 10.70 | |
| 192 | 11.17 | 11.60 | |
| 194 | 9.72 | 9.19 | |
| 195 | 10.63 | 10.75 | −158 |
| 196 | 10.63 | 10.50 | |
| 197 | 10.95 | 11.40 | −688 |
| 198 | 11.03 | 11.30 | −769 |
| 199 | 11.08 | 11.25 | −924 |
| 200 | 11.36 | 10.48 | |
| 201 | 10.69 | 11.25 | −302 |
| 202 | 9.86 | 10.10 | |

-continued

| Compound # | Receptor Binding pkᵢ | LH Inhibition pA₂ | AUC (24 hr. after 30 ug/kg) |
|---|---|---|---|
| 203 | 10.68 | 10.30 | |
| 204 | 10.67 | 11.35 | |
| 205 | 10.52 | 11.45 | |
| 206 | 11.69 | 11.33 | −412 |
| 207 | 11.54 | 11.40 | −412 |
| 208 | 10.90 | 11.45 | −269 |
| 209 | 11.62 | 11.43 | −343 |
| 210 | 11.05 | 11.43 | |
| 211 | 10.82 | 11.50 | −449 |
| 212 | 10.47 | 10.45 | |
| 213 | 10.83 | 11.15 | |
| 214 | 9.85 | 8.37 | |
| 215 | 9.47 | 8.78 | |
| 217 | 8.72 | 8.20 | |
| 218 | 9.08 | 8.27 | |
| 219 | 9.16 | 8.11 | |
| 220 | 9.77 | 9.68 | |
| 221 | 9.69 | 9.35 | |
| 223 | 10.57 | 8.91 | |
| 228 | 10.68 | 8.00 | |
| 229 | 9.68 | 8.48 | |
| 230 | 9.96 | 8.04 | |
| 234 | 9.40 | 9.53 | |
| 236 | 9.15 | 8.14 | |
| 237 | 10.45 | 9.14 | |
| 238 | 9.60 | 9.18 | |
| 239 | 9.08 | 8.57 | |
| 252 | 10.88 | 10.95 | |
| 253 | 11.03 | 11.45 | |
| 254 | 10.92 | 10.70 | |
| 255 | 10.82 | 11.30 | |

Figure 2:
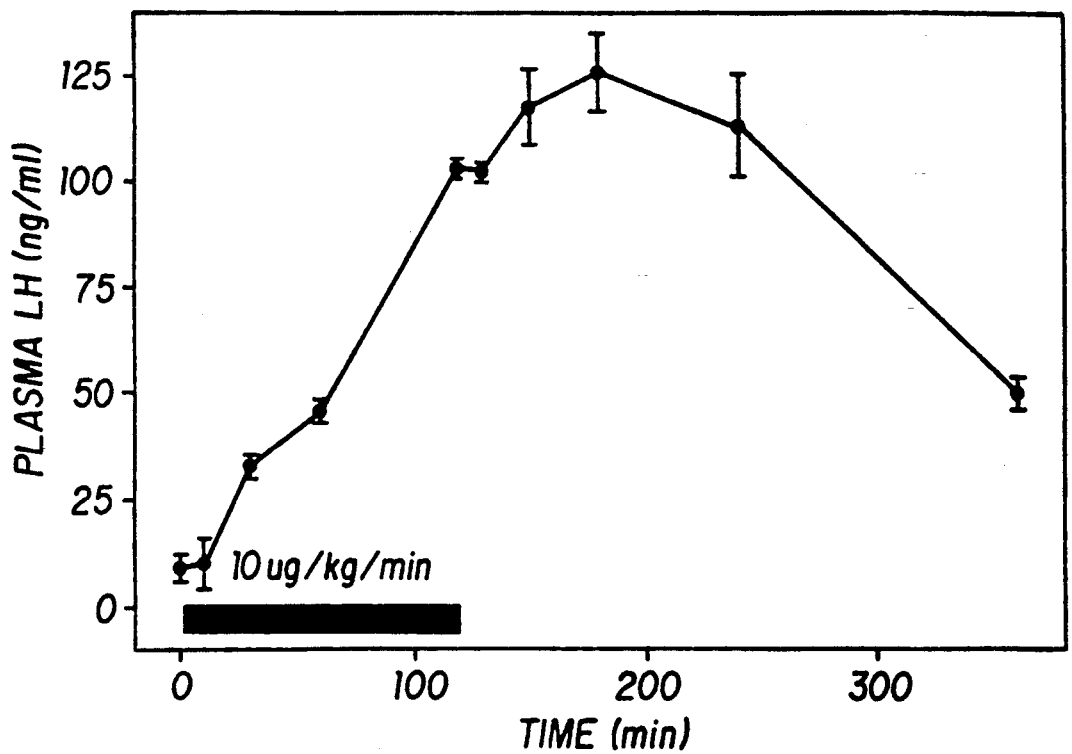
FIG. 2 is a plot of the level of LH in mature castrate male rats during and after i.v. infusion (beginning at time 0) at 10 ug/kg/min of LHRH agonist compound 24. The infusion lasted 120 minutes.

FIGS. 1 and 2 illustrate the effect on plasma LH levels in mature castrate male rats during and after i.v. infusion of compounds 20 and 24, respectively.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

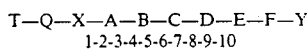
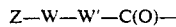

T—Q—X—A—B—C—D—E—F—Y
1-2-3-4-5-6-7-8-9-10 or a pharmaceutically acceptable salt thereof wherein
T is an acyl residue of the formula:

Z—W—W'—C(O)— wherein
Z is
  hydrogen;
  cycloalkyl of from three to seven carbon atoms;
  1-adamantyl;
  naphthyl;
  5,6-dihydro-5,5-dimethyl-2-oxo-3-phenyl-1-2H-pyrazinyl;
  phenyl;
  phenyl substituted with
  alkyl of from one to six carbon atoms,
  trihalomethyl,
  alkoxy of from one to six carbon atoms,
  thioalkoxy of from one to six carbon atoms,
  halogen,
  hydroxy,
  nitro,
  amino,
  alkylamino,
  dialkylamino, or
  alkanoylamino;
  pentafluorophenyl;
  pentamethylphenyl;
  a heterocyclic group selected from the group consisting of
  quinolyl;
  indolyl;
  furyl;
  benzo(b)furyl;
  thienyl;
  benzo(b)thienyl;
  imidazolyl;
  thiazolyl;
  benzoxazolyl;
  pyridyl;
  pyrimidinyl;
  morpholinyl;
  piperazinyl;
  pyrrolidinyl;
  piperidinyl;
  pyrazolyl;
  isoquinolyl; and
  imidazolyl;
W is absent or is an alkylene group of from one to six carbon atoms or alkenylene group of from two to six carbon atoms;
W' is absent or is selected from O, S, and $NH_2$;
Q is absent
X is an amino acyl residue optionally substituted on the α-amino nitrogen atom with $C_1$–$C_3$ alkyl selected from
  D-3-(benzo(b)thien-3-yl)alanyl;
  D-3-(thien-2-yl)alanyl;
  D-3-(4-chlorophenyl)alanyl;
  D-3-(cyclohexyl)alanyl;
  D-3-(4-methylphenyl)alanyl;
  D-3-(3,4,5-trimethylphenyl)alanyl;
  D-3-(naphth-1-yl)alanyl;
  D-N-a-methyl-3-(naphth-1-yl)alanyl;
  L-N-a-methyl-3-(naphth-1-yl)alanyl;
  D-3-(naphth-1-yl)alanyl;
  D-3-(naphth-2-yl)alanyl;
  D-phenylalanyl;
  D-3-pyrid-3-yl)alanyl;
  L-3-(pyrid-3-yl)alanyl;
  D-3-(quinol-3-yl)alanyl;
  D-3-(thiazol-5-yl)alanyl;
  D-tryptophyl;
  L-tryptophyol;
  D-5-fluorotryptophyl;
  D-tryptophyl(N-indoleformyl);
  N-methyl-D-tryptophyl;
  D-tyrosyl;
  O-methyl-D-tyrosyl; and
  D-prolyl;
A is an amino acyl residue optionally substituted on the α-amino nitrogen atom with $C_1$–$C_3$ alkyl selected from
  L-seryl;
  N-a-methyl-L-seryl;
  O-benzyl-L-seryl;
  L-prolyl;
  3-hydroxy-L-prolyl; and
  2,3-diaminopropionyl;

B is an amino acyl residue optionally substituted on the α-amino nitrogen atom with $C_1$–$C_3$ alkyl selected from
L-tyrosyl;
N-a-methyl-L-tyrosyl;
N-a-methyl-L-histidyl;
N-a-methyl-3-(cyclohexyl)-L-alanine;
L-3-(4-chlorophenyl)alanyl;
L-3-(cyclohexyl)alanyl;
O-methyl-L-tyrosyl;
L-phenylalanyl;
L-histidyl; and
a group having the structure

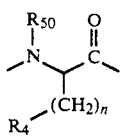

wherein n is 1 to 4; $R_{50}$ is hydrogen, methyl, ethyl, propyl or isopropyl; and $R_4$ is

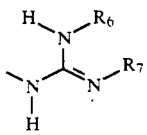

where $R_6$ and $R_7$ are independently selected from hydrogen and alkyl of from one to six carbon atoms;
C is a D-amino acyl residue optionally substituted on the α-amino nitrogen atom with $C_1$–$C_3$ alkyl selected from
D-arginyl;
D-citrullyl;
D-histidyl;
D-homocitrullyl;
D-leucyl;
D-lysyl;
D-ornithyl;
D-a-N-nictotinyl)ornithyl;
D-seryl;
D-tryptophyl;
D-tyrosyl;
e-N-(nicotonyl)D-lysyl;
e-N-(quinolyl)-D-lysyl;
e-N-(pyrazinyl)-D-lysyl;
e-N-(4-methoxybenzoyl)lysyl;
e-N-((4-methoxyphenyl)acetyl)-D-lysyl;
e-N-((morpholinyl)carbonyl)lysyl;
e-N-((4-methylpiperazin-1-yl)carbonyl)lysyl;
D-3-(benzo(b)thien-3-yl)alanyl;
D-3-(4-chlorophenyl)alanyl;
D-3-naphth-2-yl)alanyl;
D-3-(pyridyl)alanyl;
D-3-(quinolyl)alanyl;
D-3-(thiazolyl)alanyl;
O-(a-L-rhammnosyl)-D-seryl; and
a group having the structure

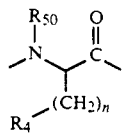

wherein n is 1 to 4; $R_{50}$ is hydrogen, methyl, ethyl, propyl or isopropyl; and $R_4$ is

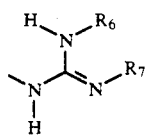

where $R_6$ and $R_7$ are independently selected from hydrogen and alkyl of from one to six carbon atoms;
D is an amino acyl residue optionally substituted on the α-amino nitrogen atom with $C_1$–$C_3$ alkyl selected from
L-leucyl;
L-seryl;
3-(cyclohexyl)alanyl;
L-valyl; and
L-isoleucyl;
E is an amino acyl residue optionally substituted on the α-amino nitrogen atom with $C_1$–$C_3$ alkyl selected from
L-arginyl;
e-N-isopropyl-L-ornithyl;
e-N-(cyclohexyl)-L-lysyl;
e-N-isopropyl-L-lysyl;
L-lysyl;
L-histidyl; and
a group having the structure

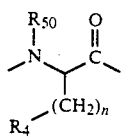

wherein n is 1 to 4; $R_{50}$ is hydrogen, methyl, ethyl, propyl or isopropyl; and $R_4$ is

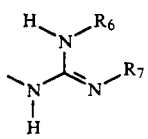

where $R_6$ and $R_7$ are independently selected from hydrogen and alkyl of from one to six carbon atoms;
F is an amino acyl residue optionally substituted on the α-amino nitrogen atom with $C_1$–$C_3$ alkyl selected from
L-prolyl;
N-ethyl-L-prolineamide;
N-a-methyl-L-alanyl; and
L-thioprolyl;
Y is an amino acyl residue optionally substituted on the α-amino nitrogen atom with $C_1$–$C_3$ alkyl selected from D-alaninamide;
glycylamide;
D-serinamide;
aza-glycylamide;
sarcosylamide; and
N-a-methyl-L-alaninamide;
with the proviso that when F is N-ethyl-prolinamide, Y is absent.

2. The compound of claim 1 wherein
T is
   acetyl,
   cyclopentlycarbonyl,
   phenylacetyl,
   3-phenylpropionyl,
   2-naphthylpropionyl,
   3-m-fluorophenyl)propionyl,
   3-(p-fluorophenyl)propionyl,
   3-(o-fluorophenyl)propionyl,
   3-(m,p-difluorophenyl)propionyl,
   3-(o,p-difluorophenyl)propionyl,
   3-(p-chlorophenyl)propionyl,
   1-naphthylacetyl,
   3-(p-fluorophenyl)acetyl,
   morpholinocarbonyl,
   2-naphthylethylaminocarbonyl,
   cyclohexylaminocarbonyl,
   phenylethylaminocarbonyl,
   ethylaminocarbonyl,
   5,6-dihydro-5,5-dimethyl-2-oxo-3-phenyl-1-(2H)-pyrazineacetyl,
   3-indolepropionyl,
   3-indoleacetyl,
   nictinyl, or
   3-indolecarbonyl;
X is
   D- or L-tryptyl,
   D- or L-N-methyltryptyl,
   D-5-(fluoro)tryptyl,
   D-N-methyl-(5-fluoro)tryptyl,
   D-3-(1-naphthyl)alanyl,
   D-3-(2-naphthyl)alanyl,
   D-phenylalanyl,
   D-N-methylphenylalanyl,
   D-N-methyl-3-(1-naphthyl)alanyl,
   D-tyrosyl,
   D-N-methyl-O-methyltyrosyl,
   D-)-methyltyrosyl,
   D-O-ethyltyrosyl,
   D-3-(4-chlorophenyl)alanyl,
   D-N-methyl-3-(2-thienyl)alanyl,
   D-prolyl,
   D-3-ethylprolyl,
   D-N-methyl-3-(1-naphthyl)alanyl,
   D-or L-3-(3-pyridyl)alanyl, or
   D-N-methyl-3-(4-chlorophenyl)alanyl;
A is
   L-seryl,
   N-methyl-L-seryl,
   O-benzylseryl,
   N-methylalanyl,
   L-prolyl,
   3-hydroxyl-L-prolyl, or 2,3-diaminopropionyl;
B is
   L-tyrosyl,
   N-methyltyrosyl,
   L-phenylalanyl
   N-methyl-L-phenylalanyl,
   O-methyl-L-tyrosyl,
   N-methyl-O-methyl-L-tyrosyl, or
   O-ethyl-L-tyrosyl;
C is
   D-leucyl,
   D-tryptyl,
   D-tyrosyl,
   D-4-chlorophenylalanyl,
   D-3-(2-naphthyl)alanyl,
   D-arginyl,
   D-lysyl-(N-epsilon-nicotinyl),
   D-lysyl-(N-epsilon-quinolylcarbonyl);
D is
   L-leucyl,
   N-methyl-L-leucyl, isoleucyl,
   L-seryl,
   3-cyclohexylalanyl, or
   N-methyl-3-cyclohexylalanyl;
E is
   L-arginyl,
   L-lysyl,
   L-lysyl-(N-epsilon-isopropyl), or
   N-methyl-L-arginyl;
F is
   L-prolyl, or
   N-methyl--L-alanyl;
Y is
   glycineamide,
   D-alanylamide,
   ethylamide, or
   azaglycineamide.

3. A compound selected from the group consisting of:
(3-10)(N-3(4-fluorophenyl)propionyl-D-2-Thia$^3$-N-Me-Tyr$^5$-D-Lys$^6$(Nic)-D-Ala$^{10}$) LHRH;
(3-10)(N-3-(4-fluorophenyl)propionyl-D-Trp$^{3,6}$-(N-indoleformyl)-D-Ala$^{10}$)LHRH;
(3-10)(N-3-(4-fluorophenyl)propionyl-D-Trp$^{3,6}$-N-Me-Tyr$^5$-D-Ala$^{10}$)LHRH;
(3-10)(N-3-(4-fluorophenyl)propionyl-D-3-Pal$^3$-N-Me-Tyr$^5$-D-Lys$^6$(Nic)-D-Ala$^{10}$)LHRH;
(3-10)(N-3-(4-fluorophenyl)propionyl-D-2-Thia$^3$-N-Me-Tyr$^5$-D-Lys$^6$-D-Ala$^{10}$)LHRH;
(3-10)(N-3-(4-fluorophenyl)propionyl-D-3-Trp$^3$-N-Me-Tyr$^5$-D-Lys$^6$(Nic)-D-Ala$^{10}$)LHRH;
(3-10)(N-(3-(4-Fluorophenyl)propionyl-D-Bal$^3$-NMeTyr$^5$-D-Lys$^6$(N-epsilon-nicotinyl)-Lys$^8$( N-epsilon-isopropyl)-D-Ala$^{10}$)LHRH;
(3-10)(N-(3-(4-FLuorophenyl)propionyl)-D-Trp$^3$-NMeTyr$^5$-D-Lys$^6$(N-epsilon-nicotinyl)-Lys$^8$( N-epsilon-isopropyl)-D-Ala$^{10}$)LHRH;
(3-10)(N-(3-(4-Fluorophenyl)propionyl)-D-1-Nal$^3$-NMeTyr$^5$-D-3-Pal$^6$-Lys$^8$(N-epsilon -isopropyl)-D-Ala$^{10}$)LHRH;
(3-10)(N-(3-(4-Fluorophenyl)propionyl)-D-1-Nal$^3$-NMeTyr$^5$-D-Lys$^6$(N-epsilon-nicotinyl)-Lys$^8$ (N-epsilon-isopropyl)-Sar$^{10}$)LHRH;
(3-10)(N-(3-(4-Fluorophenyl)propionyl)-D-1-Nal$^3$-NMeTyr$^5$-D-Lys$^6$(N-epsilon-nicotinyl)-Lys $^8$(N-epsilon-isopropyl)-Azagly$^{10}$)LHRH;
(3-10)(N-(3-(4-Fluorophenyl)propionyl)-D-1-Nal$^3$-NMeTyr-D-Lys$^6$(N-epsilon-nicotinyl)-Lys$^8$( N-epsilon-isopropyl)-D-Ser$^{10}$)LHRH;
(3-10)(N-(3-(4-Fluorophenyl)propionyl)-D-1-Nal$^3$-NMeTyr(OCH$_3$)-D-Lys(N-epsilon-nicotinyl)-Lys$^3$-( N-epsilon-isopropyl)-D-Ala$^{10}$)LHRH;
(3-10)(N-(3-(4-Fluorophenyl)propionyl)-D-1-Nal$^3$-NMeTyr$^5$-D-Ser$^6$(O-alpha-L-Rha)-Lys$^8$( N-epsilon-isopropyl)-D-Ala$^{10}$)LHRH;

(3-10)(N-(3-(4-Fluorophenyl)propionyl)-D-1-Nal³-NMeArg⁵-D-4-(4-methoxybenzoyl)-Homoala⁶-D-Ala¹⁰)LHRH;

(3-10)(N-(-3-(4-Fluorophenyl)propionyl)-D-1-Nal³-NMeTyr⁵-D-Arg⁶(NG-diEt)-Arg⁸(NG-diEt)-D-Ala¹⁰)LHRH;

(3-10)(N-(3-(4-Fluorophenyl)propionyl)-D-1-Nal³-NMeTyr⁵-D-Cit⁶-D-Ala¹⁰)LHRH;

(3-10)(N-(3-(4-fluorophenyl)propionyl)-D-1-Nal³-D-Cit⁶-D-Ala¹⁰)LHRH;

(3-10)(N-(3-(4-Fluorophenyl)propionyl)-D-1-Nal³-NMeTyr⁵-D-Lys⁶(N-epsilon-2-carbonylpyrazine)-Lys⁸(N-epsilon-isopropyl)-D-Ala¹⁰)LHRH;

(3-10)(N-(3-(4-Fluorophenyl)propionyl)-D-1-Nal³-NMeTyr⁵-D-Lys⁶(N-epsilon-4-methoxybenzoyl)-Lys⁸(N-epsilon-isopropyl)-D-Ala¹⁰)LHRH;

(3-10)(N-(3-(4-Fluorophenyl)propionyl)-D-1-Nal³-NMeTyr⁵-D-Lys⁶(N-epsilon-nicotinyl)-Cha⁷-Lys(N-epsilon-isopropyl)-D-Ala¹⁰)LHRH;

(3-10)(N-(3-(4-Fluorophenyl)propionyl)-D-1-Nal³-NMeTyr⁵-D-Lys⁶(N-epsilon-nicotinyl)-NMeLeu⁷-Lys⁸(N-epsilon-isopropyl)-D-Ala¹⁰)LHRH;

(3-10)(N-(3-(4-Fluorophenyl)propionyl)-D-1-Nal³-NMeTyr⁵-D-Lys⁶(N-epsilon-nicotinyl)-Lys⁸ (N-epsilon-cyclohexyl)-D-Ala¹⁰)LHRH; and (3-10)(N-3-(4-Fluorophenyl)propionyl)-D-1-Nal³-NMeTyr⁵-D-Lys⁶(N-epsilon-nicotinyl)-Orn⁸ (N-delta-isopropyl)-D-Ala¹⁰)LHRH.

4. N-(4-fluorophenylpropionyl)-D-Nal-Ser-NMeTyr-D-Lys(Nic)-Leu-Lys(Isp)-Pro-D-Ala-NH₂; or a pharmaceutically acceptable salt thereof.

5. A compound having the name N-3-(4-fluorophenyl)propionyl-D-1-Nal-Ser-NMeTyr-D-Lys(Nic)-Leu-Lys(Isp)-Pro-Azagly-NH₂ or a pharmaceutically acceptable salt thereof.

6. A method for suppressing levels of sex hormones in male or female mammals comprising administering to a host in need of such treatment a therapeutically effective amount of an LHRH antagonist compound of claim 1.

7. A pharmaceutical composition for suppressing levels of sex hormones in male or female mammals, comprising a pharmaceutical carrier and a therapeutically effective amount of an LHRH antagonist compound of claim 1.

8. A method for suppressing levels of sex hormones in male or female mammals comprising administering to a mammal in need of such treatment a therapeutically effective amount of a compound of claim 1 in combination with a therapeutically effective amount of an antiandrogenic agent.

* * * * *